United States Patent
Duke et al.

(10) Patent No.: US 11,446,102 B2
(45) Date of Patent: *Sep. 20, 2022

(54) HAND CONTROLLER APPARATUS INCLUDING ERGONOMIC FEATURES FOR A ROBOTIC SURGERY SYSTEM

(71) Applicant: Titan Medical Inc., Toronto (CA)

(72) Inventors: Jonathan Bradley Duke, Louisville, CO (US); Chad Clayton Walters, Apex, NC (US); Olivier Franck Currat, Louisville, CO (US); Eric Collins, Louisville, CO (US); William Jacob Ward, Apex, NC (US); Mark Curtis Rector, Raleigh, NC (US); Brandon Michael Kelly, Raleigh, NC (US); Michael Darter Collins, Holly Springs, NC (US); Zachary Kevin Durand, Waxhaw, NC (US)

(73) Assignee: Titan Medical Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/643,357

(22) Filed: Dec. 8, 2021

(65) Prior Publication Data

US 2022/0096181 A1 Mar. 31, 2022

Related U.S. Application Data

(63) Continuation of application No. 17/468,186, filed on Sep. 7, 2021, which is a continuation of application (Continued)

(51) Int. Cl.
*A61B 34/00* (2016.01)
*A61B 34/30* (2016.01)

(52) U.S. Cl.
CPC .............. *A61B 34/30* (2016.02); *A61B 34/25* (2016.02); *A61B 34/74* (2016.02); *A61B 34/76* (2016.02);
(Continued)

(58) Field of Classification Search
CPC ...................................... A61B 34/30
(Continued)

(56) References Cited

U.S. PATENT DOCUMENTS

| 4,980,626 A | 12/1990 | Hess |
| 5,290,386 A | 3/1994 | Trudeau |

(Continued)

FOREIGN PATENT DOCUMENTS

| CN | 102973321 A | 3/2013 |
| CN | 103687701 A | 3/2014 |

(Continued)

OTHER PUBLICATIONS

Titan Medical Videos, posted at titanmedicalinc.com, no posting date, retrieved Nov. 22, 2021. online, URL: https://titanmedicalinc.com/videos/ (Year: 2021), 4 pages.

(Continued)

*Primary Examiner* — Nicole F Lavert
(74) *Attorney, Agent, or Firm* — Knobbe, Martens, Olson & Bear LLP

(57) ABSTRACT

A hand controller apparatus for controlling a tool in a robotic surgery system has a body with a proximal end and a distally located interface end that can be coupled to an input apparatus for controlling a surgical tool. The hand controller apparatus includes a control lever attached to a pivot joint proximate a side surface of the body and extending along the body and away from the proximal end, the control lever being laterally moveable relative to the side surface of the body about the pivot joint. The control lever includes a tail (Continued)

region adjacent to the pivot joint and a paddle region connected to the tail region and extending toward the distally located interface end. The tail region includes an inner surface facing the body and an outer surface opposing the inner surface, and at least part of the outer surface of the tail region is outwardly curved.

20 Claims, 35 Drawing Sheets

Related U.S. Application Data

No. 16/174,602, filed on Oct. 30, 2018, now Pat. No. 11,116,591.

(52) U.S. Cl.
CPC ......... *A61B 34/77* (2016.02); *A61B 2034/252* (2016.02); *A61B 2034/301* (2016.02); *A61B 2034/305* (2016.02); *A61B 2034/744* (2016.02)

(58) Field of Classification Search
USPC ...................................................... 606/130
See application file for complete search history.

(56) References Cited

U.S. PATENT DOCUMENTS

| | | |
|---|---|---|
| 5,482,409 A | 1/1996 | Dunning |
| 5,741,113 A | 4/1998 | Bacchi |
| 6,587,750 B2 | 7/2003 | Gerbi et al. |
| 6,793,653 B2 | 9/2004 | Sanchez et al. |
| 7,074,179 B2 | 7/2006 | Wang et al. |
| 8,241,271 B2 | 8/2012 | Millman et al. |
| 8,521,331 B2 | 8/2013 | Itkowitz |
| 8,638,057 B2 | 1/2014 | Goldberg et al. |
| 9,763,739 B2 | 9/2017 | Schaible et al. |
| D813,203 S | 3/2018 | Hardi |
| D817,300 S | 5/2018 | Bristol |
| D840,360 S | 2/2019 | Scott |
| 10,426,561 B1 | 10/2019 | Kelly et al. |
| D867,309 S | 11/2019 | Detering |
| 10,568,707 B2 | 2/2020 | Schaible et al. |
| D882,529 S | 4/2020 | Scott |
| 10,758,311 B2 | 9/2020 | Kelly et al. |
| D900,042 S | 10/2020 | Scott |
| D910,845 S | 2/2021 | Kwon |
| 2003/0045900 A1 | 3/2003 | Hahnen |
| 2006/0261770 A1 | 11/2006 | Kishi et al. |
| 2009/0058342 A1 | 3/2009 | Nihei |
| 2010/0080669 A1 | 4/2010 | Labonville et al. |
| 2010/0161129 A1 | 6/2010 | Costa et al. |
| 2011/0118748 A1 | 5/2011 | Itkowitz |
| 2013/0211590 A1 | 8/2013 | Diolaiti et al. |
| 2014/0005704 A1 | 1/2014 | Vakharia |
| 2015/0025549 A1 | 1/2015 | Kilroy |
| 2015/0080924 A1 | 3/2015 | Stulen et al. |
| 2016/0066913 A1 | 3/2016 | Swayze et al. |
| 2017/0225337 A1 | 8/2017 | Schaible et al. |
| 2017/0361225 A1 | 12/2017 | Goslin et al. |
| 2017/0367777 A1 | 12/2017 | Kralicky et al. |
| 2018/0168758 A1 | 6/2018 | Lutzow et al. |
| 2018/0271607 A1 | 9/2018 | Kralicky et al. |
| 2020/0129249 A1 | 4/2020 | Kelly |

FOREIGN PATENT DOCUMENTS

| | | | | |
|---|---|---|---|---|
| WO | WO 2013/018934 A1 | 2/2013 | | |
| WO | WO 2015/163943 A1 | 10/2015 | | |
| WO | WO 2016/201544 A1 | 12/2016 | | |
| WO | WO-2016201544 A1 * | 12/2016 | ............ | A61B 18/12 |
| WO | WO 2017/177547 A1 | 10/2017 | | |
| WO | WO 2017/210501 A1 | 12/2017 | | |
| WO | WO 2018/013197 A1 | 1/2018 | | |
| WO | WO 2018/217435 A1 | 11/2018 | | |

OTHER PUBLICATIONS

Analog Devices, "Integrated AMR Angle Sensor and Signal Conditioner," Data Sheet ADA4571, Rev. 0, 2014, 21 pages.
Azoteq (PTY) Ltd, "IQS550/572/525-B000—Capacitive Trackpad/Touchscreen Controller," IQS5xx-B000 Trackpad Datasheet, Revision 2.0, Nov. 2016, 79 pages.
Examination Report issued in European Application No. 16810648.2 dated Apr. 7, 2020.
Extended European Search Report received in Application No. EP 16810648.2, dated Jun. 20, 2018 in 8 pages.
Integrated Device Technology, Inc., "IDT Inductive Position Sensors," 2017, 13 pages.
Integrated Device Technology, Inc., "Inductive Position Sensor IC," ZMID5201/02/03 Datasheet, Jun. 22, 2018, 33 pages.
Integrated Device Technology, Inc., "ZMID520x Evaluation Kit User Manual," Dec. 10, 2017, 39 pages.
Integrated Device Technology, Inc., "ZMID520x Inductive Position Sensor Family," Product Overview, 2018, 2 pages.
Integrated Device Technology, Inc., "ZMID520xMARC13001 Arc Application Module User Manual," Dec. 12, 2017, 15 pages.
International Search Report and Written Opinion dated Feb. 7, 2020 in International Application No. PCT/US2019/058170, in 8 pages.
International Search Report in PCT Application No. PCT/CA2016/000112 dated Jul. 21, 2016 in three pages.
Intuitive Surgical, "da Vinci SP," downloaded on Oct. 9, 2018 from https://www.intuitivesurgcal.com/sp/, in 5 pages.
Kasemsadeh, "LDC1612/LDC1614 Linear Position Sensing," Application Report SNOA931, Texas Instruments, Apr. 2015, 14 pages.
Liu, Ergonomics, pp. 34-38, Liaoning Art Publisher, Jul. 2005.
Microchip Technology Inc., "AT42QT1011 Data Sheet," 2017, 31 pages.
MPS, "14-Bit, Digital, Contactless Angle Sensor with ABZ Incremental & PWM Outputs," MagAlpha MA730, Rev. 1.01, Oct. 13, 2017, 27 pages.
Search Report dated Nov. 25, 2019 in Chinese Application No. 201680041417X, in 2 pages.
SMSC, "8 Channel Capacitive Touch Sensor with 8 LED Drivers," CAP1188 Datasheet, Revision 1.32, Jan. 5, 2012, 93 pages.
Texas Instruments, "DRV2605L 2- to 5.2-V Haptic Driver for LRA and ERM with Effect Library and Smart-Loop Architecture," May 2014, Revised Mar. 2018, 70 pages.
Texas Instruments, "LDC1612, LDC1614 Multi-Channel 28-Bit Inductance to Digital Converter (LDC) for Inductive Sensing," Dec. 2014, Revised Mar. 2018, 65 pages.
Third Office Action dated Sep. 28, 2020 in Chinese Application No. 01680041417.X, in 17 pages.
Written Opinion received in PCT Application No. PCT/CA2016/000112 dated Jul. 21, 2016 in four pages.
Zhu, Ergonomics, pp. 186-190, Xidian University Publisher, Jan. 2006.

* cited by examiner

INSTRUMENT CLUTCH
TURN ON
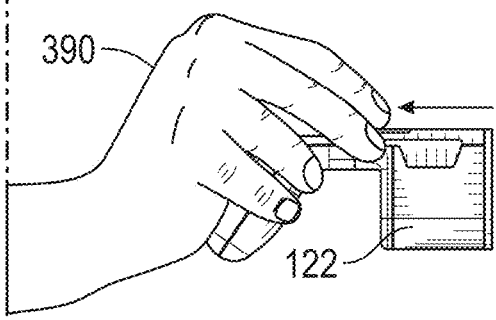 Swipe Backward 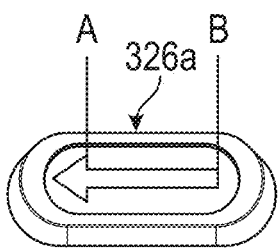
+
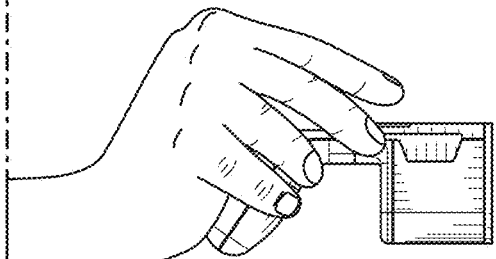 Release 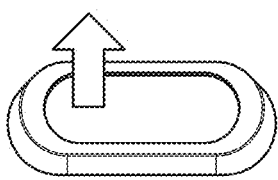
FIG. 21A
TURN OFF
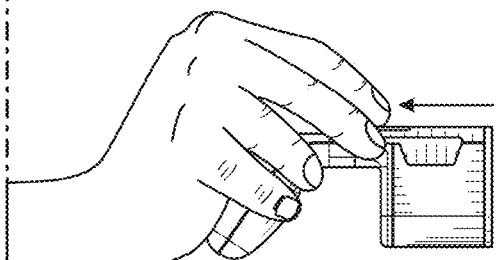 Swipe Backward 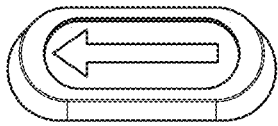
+
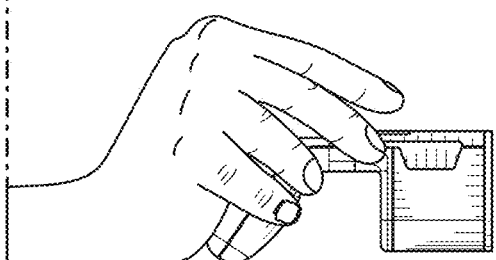 Release 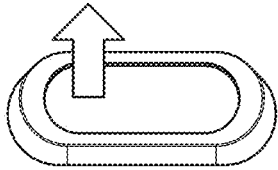
FIG. 21B

US 11,446,102 B2

HAND CONTROLLER APPARATUS INCLUDING ERGONOMIC FEATURES FOR A ROBOTIC SURGERY SYSTEM

INCORPORATION BY REFERENCE TO ANY PRIORITY APPLICATIONS

U.S. application Ser. No. 17/468,186 filed on Sep. 7, 2021 and U.S. application Ser. No. 16/174,602 filed Oct. 30, 2018, now U.S. Pat. No. 11,116,591, for which a domestic priority claim is identified in the Application Data Sheet as filed with the present application are hereby incorporated by reference under 37 CFR 1.57.

TECHNICAL FIELD

This disclosure relates generally to robotic surgery systems and more particularly to a hand controller apparatus for receiving operator input for controlling the robotic surgery system to perform surgical procedures.

DESCRIPTION OF RELATED ART

Robotic surgery systems generally include an operator interface that receives operator input from a surgeon and causes corresponding movements of surgical tools within a body cavity of a patient to perform a surgical procedure. For example, the operator may grasp and move a hand grip while the operator interface senses movements of the hand grip. The operator interface and hand grip may operate to sense inputs responsive to movement of the operator's hand in several different degrees of freedom, thus providing inputs for causing the surgical tool to mimic movements of the operator's hand. Additional movements such as opening and closing of jaws of an end effector associated with the surgical tool may also be initiated in response to additional operator inputs received at the operator interface.

SUMMARY

In some cases, a hand controller apparatus for controlling a tool in a robotic surgery can include a body including a proximal end and a distally located interface end configured to be coupled to an input apparatus configured to control a surgical tool. The hand controller apparatus can also include a control lever attached to a pivot joint proximate a side surface of the body and extending along the body and away from the proximal end, the control lever being laterally moveable relative to the side surface of the body about the pivot joint. The hand controller apparatus can also include and a lateral movement detector configured to magnetically or inductively detect a lateral movement of the control lever. Detection of the lateral movement can cause the input apparatus to control movement of the surgical tool based on the detected lateral movement of the control lever.

The hand controller apparatus of any of preceding paragraphs and/or any of hand controller apparatuses described below can include one or more of the following features. The lateral movement detector can be positioned in the body or in the control lever. The control lever can include a wiper disposed inside the body and extending from the pivot joint toward the proximal end and a paddle disposed outside the body and extending at an angle from the pivot joint toward the distally located interface end. The wiper can be configured to move in a direction opposite to a lateral movement of the paddle. The lateral movement detector can include a magnetic angular sensor configured to detect an angle formed between the paddle and the side surface of the body.

The hand controller apparatus of any of preceding paragraphs and/or any of hand controller apparatuses described below can include one or more of the following features. The hand controller apparatus can further include a magnet attached to the wiper and configured to move along with the wiper. The magnetic angular sensor can be configured to detect the angle based on movement of the magnet. At least a portion of the wiper can include a magnetic material. The magnetic angular sensor can be configured to detect the angle based on movement of the portion of the wiper. The lateral movement detector can include an inductive sensor including a curved coil and configured to detect a curved movement of the wiper based on an electrical current induced at the curved coil by the movement of the wiper. The wiper can be formed at least partially of a metal.

The hand controller apparatus of any of preceding paragraphs and/or any of hand controller apparatuses described below can include one or more of the following features. The control lever can include a paddle disposed outside the body and extending from the pivot joint toward the distally located interface end. The lateral movement detector can include an inductive sensor configured to detect a non-linear movement of a metallic portion disposed in or integrally formed with the paddle. The inductive sensor can include a substantially trapezoidal shaped coil. The inductive sensor can include a coil that can be curved toward the metallic portion. The metallic portion can include a substantially trapezoidal shape. The inductive sensor can include a substantially elliptical shaped coil. A portion of the elliptical shaped coil is curved toward the metallic portion.

The hand controller apparatus of any of preceding paragraphs and/or any of hand controller apparatuses described below can include one or more of the following features. A portion of the metallic portion is curved toward the substantially elliptical shaped coil. The control lever can include a paddle disposed outside the body and extending from the pivot joint toward the distally located interface end. The lateral movement detector can include a proximity sensor configured to detect a position of the paddle with respect to the side surface of the body. The hand controller apparatus can further include a presence detector configured to detect a presence of a hand of an operator on the body. The presence detector can include a capacitive proximity sensor coated on an inner wall of the body. The hand controller apparatus can further include a palm grip disposed on or in the proximal end, the palm grip including a generally downwardly curved and rounded shape configured to support a portion of an operator's palm.

In some cases, a robotic surgery system can include an instrument station including an insertion device configured to support a surgical tool. The robotic surgery system can also include a workstation in configured to be in data communication with the instrument station. The workstation can include a hand controller apparatus configured to control movement of the tool. The hand controller apparatus can include a body including a proximal end and a distally located interface end coupled to the input device. The hand controller apparatus can also include a control lever attached to a pivot joint proximate a side surface of the body and extending along the body and away from the proximal end, the control lever being laterally moveable relative to the side surface of the body about the pivot joint. The hand controller apparatus can also include a lateral movement detector configured to magnetically or inductively detect a lateral movement of the control lever. The input device can be configured to control movement of the tool based on the detected lateral movement of the control lever.

The robotic surgery system of any of preceding paragraphs and/or any of robotic surgery systems described below can include one or more of the following features. The control lever can include a wiper disposed inside the body and extending from the pivot joint toward the proximal end and a paddle disposed outside the body and extending at an angle from the pivot joint toward the distally located interface end. The wiper can be configured to move in a direction opposite to a lateral movement of the paddle. The lateral movement detector can include a magnetic angular sensor configured to detect an angle formed between the paddle and the side surface of the body. The lateral movement detector can include an inductive sensor including a curved coil and configured to detect a curved movement of the wiper based on an electrical current induced at the curved coil by the movement of the wiper. The wiper can be formed at least partially of a metal. The control lever can include a paddle disposed outside the body and extending from the pivot joint toward the distally located interface end. The lateral movement detector can include an inductive sensor configured to detect a non-linear movement of a metallic portion disposed in or integrally formed with the paddle.

In some cases, a method of operating a hand controller apparatus for controlling a tool in a robotic surgery system can include detecting lateral movement of a control lever of the hand controller apparatus between a closed position and an open position, the control lever rotatably attached to a body of the hand controller apparatus and configured to control opening and closing of a surgical tool. The method can also include magnetically or inductively detecting a change in an angle of the control lever relative to the body of the hand controller apparatus when the control lever is moved between the closed position and the open position. The method can also include causing opening and closing of the surgical tool based on the detected change in the angle.

The method of operating a hand controller apparatus of any of preceding paragraphs and/or any of methods described below can include one or more of the following features. The control lever can include a wiper disposed inside the body and extending from a pivot joint toward a proximal end of the body and a paddle disposed outside the body and extending from the pivot joint toward a distally located interface end, the paddle configured to move between the open and close positions. A magnetic portion can be disposed in or integrally formed with the wiper. The wiper and the magnetic portion can laterally move between a first position and a second position about the pivot joint in a direction opposite to a lateral movement of the paddle, the first and second positions respectively corresponding to the open and close positions of the paddle. Magnetically or inductively detecting the change in the angle can include determining an angular position of the magnetic portion between the first position and the second position in response to a lateral movement of the wiper and detecting the change in the angle based on the determined angular position of the magnetic target.

The method of operating a hand controller apparatus of any of preceding paragraphs and/or any of methods described below can include one or more of the following features. Determining the angular position can be performed with a magnetic angular detector disposed below the wiper. The control lever can include a wiper disposed inside the body and extending from a pivot joint toward a proximal end of the body and a paddle disposed outside the body and extending from the pivot joint toward a distally located interface end, the paddle configured to move between the open and close positions. A metallic portion can be disposed in or integrally formed with the wiper. Controlling the wiper and the metallic portion can partially rotate over a curved inductive coil between a first position and a second position about the pivot joint in a direction opposite to a lateral movement of the paddle. The first and second positions can respectively correspond to the open and close positions of the paddle. Magnetically or inductively detecting the change in the angle can include detecting induced electrical current at the curved inductive coil caused by a rotation of the wiper, demodulating the detected electrical current to produce a signal representing a position of the metallic portion and detecting the change in the angle based on the produced signal.

The method of operating a hand controller apparatus of any of preceding paragraphs and/or any of methods described below can include one or more of the following features. The control lever can include a paddle disposed outside the body and extending from a pivot joint, wherein a metallic portion can be disposed in or integrally formed with the paddle. The paddle and the metallic portion can move over an inductive coil between the open and close positions, the inductive coil facing the metallic portion. Magnetically or inductively detecting the change in the angle can include detecting induced electrical current at the inductive coil in response to a movement of the metallic portion, demodulating the detected electrical current to produce a signal representing a position of the metallic portion and detecting the change in the angle based on the produced signal. The inductive coil can have a substantially trapezoidal shape or a substantially elliptical shape.

In some cases, a method of operating a robotic surgery system that comprises a workstation including a hand controller apparatus and an instrument station including a surgical tool can include detecting lateral movement of a control lever of the hand controller apparatus between a closed position and an open position, the movement of the control level changing an angle between the control lever and a body of the hand controller apparatus. The method can also include magnetically or inductively detecting the change in the angle in response to the control lever moving between the closed position and the open position. The method can also include controlling an opening and closing movement of the tool based on the detected angle.

In some cases, a hand controller apparatus for controlling a tool in a robotic surgery system can include a body configured to be moved to generate a first operator input to cause a tool to move corresponding to the movement of the body. The hand controller apparatus can also include an input control interface formed on a surface of the body and configured to sense one or more of a plurality of second operator inputs associated with a plurality of tool functions, the plurality of second operator inputs being different from the first operator input. The hand controller apparatus can also include a processor configured to control the tool to perform one or more of the plurality of tool functions in response to the sensed one or more second operator inputs.

The hand controller apparatus of any of preceding paragraphs and/or any of hand controller apparatuses described below can include one or more of the following features. The tool can include a surgical instrument and at least one function of the plurality of tool functions comprises a surgery routine. The surgery routine can include controlling the surgical instrument to perform at least one of: suturing, cutting, grasping or moving in a predetermined direction. The tool can include a camera configured to image a surgical site, and wherein at least one function of the plurality of tool functions comprises at least one of: causing a lens of the camera to be washed, causing the camera to zoom in and/or out, causing the camera to pan, or causing the camera to tilt. The hand controller apparatus can further include a memory storing the plurality of tool functions corresponding with the plurality of second operator inputs.

The hand controller apparatus of any of preceding paragraphs and/or any of hand controller apparatuses described below can include one or more of the following features. The input control interface can be configured to sense at least one input of: swiping from a first side of the input control interface to a second side of the input control interface different from the first side, tapping, swiping and holding, tapping and holding, multiple tapping, or multiple tapping and holding. The processor can be configured to control the tool to perform one or more of the plurality of tool functions in response to the sensed at least one input. The input control interface can include a trackpad or a capacitive touch surface configured to sense the one or more second operator inputs. The one or more second operation inputs can include swiping from a first side of the trackpad to a second side of the trackpad different from the first side.

The hand controller apparatus of any of preceding paragraphs and/or any of hand controller apparatuses described below can include one or more of the following features. The processor can be configured to cause the tool to become locked in a current surgery position in response to the sensed swiping from the first side of the trackpad to the second side of the trackpad. The tool can include a pair of jaws, and wherein the processor is configured to control the pair of jaws of the tool to be fixed in the current surgery position while the body is being repositioned. The body can include a housing on an end thereof, the housing including a generally downwardly curved and rounded shape configured to receive and support a portion of an operator's palm. The hand controller apparatus can further include at least one control lever attached to the body at a pivot joint and extending along the body, the at least one control lever being laterally moveable about the pivot joint, and wherein the at least one control lever is configured to control one or more of the plurality of tool functions.

In some cases, a method of operating a hand controller apparatus for controlling a tool in a robotic surgery system can include generating a first operator input based on movement of a body of the hand controller apparatus, the first input configured to control the tool to move corresponding to the movement of the body. The method can also include sensing, at an input control interface formed on a surface of the body, one or more of a plurality of second operator inputs corresponding to a plurality of tool functions, the plurality of second operator inputs different from the first operator input. The method can also include, by a processor, controlling the tool to perform one or more of the plurality of tool functions in response to the sensed one or more second operator inputs.

The method of operating a hand controller apparatus of any of preceding paragraphs and/or any of methods described below can include one or more of the following features. The tool can be a surgical instrument. Controlling the tool can include controlling the surgical instrument to perform at least one of the following: suturing, cutting, grasping or moving in a predetermined direction. The tool can include a camera configured to image a surgical site. Controlling the tool can include at least one of: causing a lens of the camera to be washed, causing the camera to zoom in and/or out, causing the camera to pan, or causing the camera to tilt. The method can further include storing the plurality of tool functions corresponding with the plurality of second operator inputs in a memory.

The method of operating a hand controller apparatus of any of preceding paragraphs and/or any of methods described below can include one or more of the following features. Sensing the one or more of second operator inputs can include sensing at least one of the following inputs: swiping from a first side of the input control interface to a second side of the input control interface different from the first side, tapping, swiping and holding, tapping and holding, multiple tapping, or multiple tapping and holding. The input control interface can include a trackpad or a capacitive touch surface.

In some cases, a hand controller apparatus for controlling one or more tools in a robotic surgery system can include a body configured to be moved to generate a first operator input to control a surgical instrument of the one or more tools to move corresponding to the movement of the body. The hand controller apparatus can also include an input control interface formed on a surface of the body and configured to sense a second operator input different from the first operator input. The hand controller apparatus can also include a processor configured to control at least first and second functions of first and second tools of the one or more tools in response to the received second operator input, the first function and the second function performed mutually exclusively of each other, the first and second functions being different from each other, and the first and second tools being different from each other.

The hand controller apparatus of any of preceding paragraphs and/or any of hand controller apparatuses described below can include one or more of the following features. The processor can be configured to control the first function of the first tool in response to a first type of the second operator input while disabling the second function of the second tool, and control the second function of the second tool in response to a second type of the second operator input while disabling the first function of the first tool. The input control interface can include a trackpad or a capacitive touch surface configured to sense at least one of: swiping from a first side of the trackpad to a second side of the trackpad different from the first side, tapping, swiping and holding, tapping and holding, multiple tapping, or multiple tapping and holding.

The hand controller apparatus of any of preceding paragraphs and/or any of hand controller apparatuses described below can include one or more of the following features. The trackpad can be configured to sense at least one of the following inputs: swiping from a first side of the trackpad to a second side of the trackpad different from the first side, tapping, swiping and holding, tapping and holding, multiple tapping, or multiple tapping and holding. The processor can be configured to perform different functions based on the sensed second operator input. The capacitive touch surface can include at least one capacitive input configured to sense a single-click or a multiple-click, and wherein the processor is configured to perform different functions based on the single-click or multiple-click.

The hand controller apparatus of any of preceding paragraphs and/or any of hand controller apparatuses described below can include one or more of the following features. The first tool can a camera configured to image a surgical site, the first function being enabling and/or disabling the camera. The second tool can include an instrument clutch configured to reposition the body, the second function being enabling and/or disabling the instrument clutch. The track pad can be configured to sense swiping from a first side of the trackpad to a second side of the trackpad different from the first side and holding the second side of the trackpad. The processor can be configured to, in response to the sensed swiping and holding, disable an association of the body with the surgical instrument and enable association of the body with the camera.

The hand controller apparatus of any of preceding paragraphs and/or any of hand controller apparatuses described below can include one or more of the following features. The track pad can be further configured to sense a release of the second side, and wherein the processor is further configured to, in response to the sensed release, disable the association of the body with the camera and enable the association of the body with the surgical instrument. The track pad can be further configured to sense a first swiping from a first side of the trackpad to a second side of the trackpad different from the first side and first releasing of the trackpad, and wherein the processor is further configured to, in response to the sensed first swiping and first releasing, disable an association of the body with the surgical instrument, and permit repositioning of the body without moving the surgical instrument.

The hand controller apparatus of any of preceding paragraphs and/or any of hand controller apparatuses described below can include one or more of the following features. The track pad can be further configured to sense a second swiping from the first side of the track pad to the second side of the track pad and a second releasing of the trackpad, and wherein the processor is configured to, in response to the sensed second swiping and second releasing, enable the association of the body with the surgical instrument.

In some cases, a method of operating a hand controller apparatus for controlling one or more tools in a robotic surgery system can include generating a first operator input based on a movement of a body of the hand controller apparatus, the first operator input configured to control movement of a surgical instrument of the one or more tools. The method can also include sensing, at an input control interface formed on a surface of the body, a second operator input different from the first operator input. The method can also include, by a processor, controlling at least first and second functions of first and second tools of the one or more tools in response to the received second operator input by performing the first function and the second function mutually exclusively of each other, the first and second functions being different from each other, and the first and second tools being different from each other.

The method of operating a hand controller apparatus of any of preceding paragraphs and/or any of methods described below can include one or more of the following features. Controlling the at least first and second functions can include controlling the first function of the first tool in response to a first type of the second operator input while disabling the second function of the second tool and controlling the second function of the second tool in response to a second type of the second operator input while disabling the first function of the first tool.

In some cases, a hand controller apparatus for controlling a tool in a robotic surgery system can include a body including a proximal end and a distally located interface end configured to be coupled to an input apparatus configured to control a surgical tool. The hand controller apparatus can also include a feedback device supported by the body and configured to provide feedback to a user in response to a change in a function of the hand controller apparatus from a first mode to a second mode, the second mode different from the first mode. The function can include at least one: controlling a camera that images a surgical site, instrument clutching to reposition the hand controller apparatus, a pre-set surgery routine, or an operation to control the surgical tool. The change from the first mode to the second mode can be configured to occur within the same function.

The hand controller apparatus of any of preceding paragraphs and/or any of hand controller apparatuses described below can include one or more of the following features. When the function includes controlling the camera, the first mode can include enabling control of the camera, and the second mode can include disabling control of the camera. When the function comprises instrument clutching, the first mode can include enabling instrument clutching and the second mode can include disabling instrument clutching.

In some cases, a hand controller apparatus for controlling a tool in a robotic surgery system can include a body including a proximal end and a distally located interface end configured to be coupled to an input apparatus configured to control a surgical instrument. The hand controller apparatus can also include a feedback device positioned in or on the body and configured to provide feedback to a user in response to a change in a function of the hand controller apparatus from a first mode to a second mode, the second mode different from the first mode.

The hand controller apparatus of any of preceding paragraphs and/or any of hand controller apparatuses described below can include one or more of the following features. The feedback device can include a haptic feedback device configured to provide a haptic feedback in response to the change in the function. The haptic feedback device can include a haptic actuator and a controller configured to sense the change in the function and actuate the haptic actuator to vibrate in response thereto. The haptic actuator ca be disposed adjacent to the proximal end or the distally located interface end. The hand controller apparatus can further include an input control interface formed on an upper surface of the body and configured to receive an additional user input. The haptic actuator can be disposed adjacent to the input control interface.

The hand controller apparatus of any of preceding paragraphs and/or any of hand controller apparatuses described below can include one or more of the following features. The function can include at least one of: controlling a camera that images a surgical site, instrument clutching to reposition the hand controller apparatus, a pre-set surgery routine, or an operation to control the surgical instrument. When the function includes controlling the camera, the first mode can include enabling control of the camera and the second mode can include disabling control of the camera. When the function includes instrument clutching, the first mode can include enabling instrument clutching and the second mode comprises disabling instrument clutching.

The hand controller apparatus of any of preceding paragraphs and/or any of hand controller apparatuses described below can include one or more of the following features. The change in the function can be generated from repositioning the body or from a secondary input of the robotic surgery system remote from the body. The feedback device can include a visual feedback device configured to provide a visual feedback in response to the change in the function. The feedback device can include an audio feedback device configured to provide an audio feedback in response to the change in the function.

The hand controller apparatus of any of preceding paragraphs and/or any of hand controller apparatuses described below can include one or more of the following features. The feedback device can include a tactile feedback device configured to provide a tactile feedback in response to the change in the function. The tactile feedback can include at least one of the following: a bump, a beak, a grove, a lip, or a texture difference.

The hand controller apparatus of any of preceding paragraphs and/or any of hand controller apparatuses described below can include one or more of the following features. The feedback device can include a force feedback device configured to provide a force feedback in response to the change in the function. The force feedback device can include a self-centering wheel. The feedback device is located in a portion of the body configured to contact a user's palm. The feedback device is configured to provide different feedbacks in response to different changes in the function. The different feedbacks can be configurable by the user.

In some cases, a robotic surgery system can include an instrument station comprising an insertion device configured to support a surgical tool. The robotic surgery system can also include a workstation in data communication with the instrument station. The workstation can include a hand controller apparatus configured to receive an operator input for controlling the tool. The hand controller apparatus can include a body including a proximal end and a distally located interface end configured to be coupled to an input apparatus configured to control the tool. The hand controller apparatus can include a feedback device disposed in or on the body and configured to provide feedback to an operator in response to a change in a function of the hand controller apparatus from a first mode to a second mode, the second mode different from the first mode.

The robotic surgery system of any of preceding paragraphs and/or any of robotic surgery systems described below can include one or more of the following features. The feedback device can include at least one of the following: a haptic feedback device configured to provide a haptic feedback in response to the change in the function, a visual feedback device configured to provide a visual feedback in response to the change in the function, an audio feedback device configured to provide an audio feedback in response to the change in the function, a tactile feedback device configured to provide a tactile feedback in response to the change in the function or a force feedback device configured to provide a force feedback in response to the change in the function.

The robotic surgery system of any of preceding paragraphs and/or any of robotic surgery systems described below can include one or more of the following features. The change in the function can be generated from repositioning the body or from a secondary input of the workstation remote from the hand controller apparatus. The feedback device can be configured to provide different feedbacks in response to different changes in the function. The different feedbacks can be configurable by the operator.

In some cases, a method of operating a hand controller apparatus for controlling a tool in a robotic surgery system can include receiving an operator input. The method can also include determining that the received operator input triggers a change in a function of the hand controller apparatus from a first mode to a second mode, the second mode different from the first mode. The method can also include, with a feedback device supported by a body of the hand controller apparatus, providing operator feedback in response to the change in the function.

The method of operating a hand controller apparatus of any of preceding paragraphs and/or any of methods described below can include one or more of the following features. The function can include at least one of the following: controlling a camera that images a surgical site, instrument clutching to reposition the hand controller apparatus, a pre-set surgery routine, or an operation to control a surgical tool of the robotic surgery system. When the function includes controlling the camera, the first mode can include enabling control of the camera and the second mode can include disabling control of the camera.

The method of operating a hand controller apparatus of any of preceding paragraphs and/or any of methods described below can include one or more of the following features. When the function includes instrument clutching, the first mode can include enabling instrument clutching and the second mode comprises disabling instrument clutching. Providing the operator feedback can include providing different feedbacks in response to different changes in the function.

In some cases, a hand controller apparatus for controlling a tool in a robotic surgery system can include a body including a proximal end and a distally located interface end configured to be coupled to an input apparatus configured to control a surgical tool. The hand controller apparatus can also include a control lever attached to a pivot joint proximate a side surface of the body and extending along the body and away from the proximal end, the control lever being laterally moveable relative to the side surface of the body about the pivot joint. The control lever can include a tail region adjacent to the pivot joint and a paddle region connected to the tail region and extending toward the distally located interface end, wherein the tail region includes an inner surface facing the body and an outer surface opposing the inner surface, and wherein at least part of the outer surface of the tail region is outwardly curved.

The hand controller apparatus of any of preceding paragraphs and/or any of hand controller apparatuses described below can include one or more of the following features. The at least part of the outer surface of the tail region can include a substantially convex shape. The tail region can include a tail end horizontally overlapping the pivot joint. An outer surface of the tail end can be outwardly curved and an outer surface of the remaining portion of the tail region can be substantially flat. The tail region can include a tail end horizontally overlapping the pivot joint. A first portion of an outer surface of the tail end can be outwardly curved and a second portion of the outer surface of the tail end can be substantially flat.

The hand controller apparatus of any of preceding paragraphs and/or any of hand controller apparatuses described below can include one or more of the following features. The at least part of the outer surface of the extension can have a substantially concave shape. The control lever can further include an extension extending downwardly from the paddle region, wherein at least part of the extension is curved toward the body. The hand controller apparatus can further include a cutout formed on or in the side surface of the body and configured to accommodate the control lever therein such that a longitudinal axis of the control lever is substantially parallel to a longitudinal axis of the body.

The hand controller apparatus of any of preceding paragraphs and/or any of hand controller apparatuses described below can include one or more of the following features. The hand controller apparatus can further include a palm grip disposed in or on the proximal end, the palm grip including a generally downwardly curved and rounded shape configured to receive and support a portion of an operator's palm. The hand controller apparatus can further include a neck portion interposed between the pivot joint and the palm grip, wherein a width of the neck portion can be smaller than a width of the palm grip.

The hand controller apparatus of any of preceding paragraphs and/or any of hand controller apparatuses described below can include one or more of the following features. The neck portion can include a protruding side surface. The protruding side surface of the neck portion can have a curvature that is substantially the same as a curvature of the at least part of the outer surface of the tail region. At least one of i) the protruding side surface of the neck portion, or ii) the at least part of the outer surface of the tail region can be configured to enable an operator to rotate the body of the hand controller apparatus about a longitudinal axis of the body with the operator's finger without rotation of the operator's wrist.

The hand controller apparatus of any of preceding paragraphs and/or any of hand controller apparatuses described below can include one or more of the following features. The hand controller apparatus can further include an input control interface formed on an upper surface of the body and configured to sense an operator input. The input control interface can include a first side facing the proximal end and a second side opposing the first side and facing the distally located interface end. The hand controller apparatus can further include a slope region disposed between the first side of the input control interface and the neck portion and downwardly sloped to allow an operator's finger to be rested thereon. The slope region can be curved or linear. The input control interface can include a periphery at least part of which is raised to provide a tactile feedback for a location of the input control interface. The palm grip can be downwardly angled with respect to the neck portion to substantially resemble a natural curvature formed between an average operator's thumb and palm when the palm grip is grasped by the operator's hand.

In some cases, a robotic surgery system can include an instrument station including an insertion device configured to support a surgical tool. The robotic surgery system can also include a workstation in data communication with the instrument station. The workstation can include a hand controller apparatus configured to receive an operator input for controlling the tool. The hand controller apparatus can include a body including a proximal end and a distally located interface end configured to be coupled to an input apparatus configured to control the tool. The hand controller apparatus can also include a control lever attached to a pivot joint proximate a side surface of the body and extending along the body and away from the proximal end, the control lever being laterally moveable relative to the side surface of the body about the pivot joint. The control lever can include a tail region adjacent to the pivot joint and a paddle region extending from the tail region toward the distally located interface end. The tail region includes an inner surface facing the body and an outer surface opposing the inner surface. At least part of the outer surface of the tail region can be outwardly curved.

The robotic surgery system of any of preceding paragraphs and/or of robotic surgery systems described below can include one or more of the following features. The at least part of the outer surface of the tail region can include a substantially convex shape. The control lever can further include an extension extending downwardly from the paddle region. At least part of the downward extension can be curved toward the body. The at least part of outer surface of the tail region can be configured to enable an operator to rotate the hand controller apparatus about a longitudinal axis of the body with the operator's finger without rotation of the operator's wrist.

In some cases, a hand controller apparatus for controlling a tool in a robotic surgery system can include a body including a proximal end and a distally located interface end configured to be coupled to an input apparatus configured to control a surgical instrument. The hand controller apparatus can also include a control lever attached to a pivot joint proximate a side surface of the body and extending along the body and away from the proximal end, the control lever being laterally moveable relative to the side surface of the body about the pivot joint. The hand controller apparatus can also include a palm grip disposed in or on the proximal end, the palm grip including a substantially downwardly curved and rounded shape configured to receive and support a portion of an operator's palm. The hand controller apparatus can also include a neck portion interposed between the pivot joint and the palm grip, wherein a width of the neck portion is smaller than a width of the palm grip.

The hand controller apparatus of any of preceding paragraphs and/or any of hand controller apparatuses described below can include one or more of the following features. At least part of the neck portion may not horizontally overlap the pivot joint. The palm grip can include an upper portion extending from the neck portion toward the proximal end, a middle portion downwardly extending at a first angle from the upper portion, and a lower portion downwardly extending at a second angle from the middle portion. Each of the upper and lower portions can include a width smaller than a width of the middle portion. The upper portion includes a width greater than a width of the neck portion.

The hand controller apparatus of any of preceding paragraphs and/or any of hand controller apparatuses described below can include one or more of the following features. The body can include an upper surface accommodating an input control interface configured to sense an operator input. The upper surface can be slanted toward the side surface of the body, the slanted upper surface configured to support an operator's index finger when the palm grip is grasped by the operator's hand. The pivot joint can be disposed inside the body and positioned closer to a longitudinal axis of the body than a longitudinal axis of the control lever.

The longitudinal apparatus of any of preceding paragraphs and/or any of hand controller apparatuses described below can include one or more of the following features. The control lever can include a wiper disposed inside the body and extending from the pivot joint toward the proximal end and a paddle disposed outside the body and extending at an angle from the pivot joint toward the distally located interface end. The wiper and the paddle can be connected to the pivot joint such that longitudinal axes of the wiper and the paddle are substantially parallel to each other. The longitudinal axes of the wiper and the paddle may not intersect a center of the pivot joint.

In some cases, a hand controller apparatus for controlling a tool in a robotic surgery system can include a body including a proximal end and a distally located interface end configured to be coupled to an input apparatus configured to control a surgical tool. The hand controller apparatus can also include a control lever attached to a pivot joint proximate a side surface of the body and extending along the body and away from the proximal end, the control lever being laterally moveable relative to the side surface of the body about the pivot joint. The pivot joint can be disposed inside the body and positioned closer to a longitudinal axis of the body than a longitudinal axis of the control lever. The longitudinal axis of the control lever may not intersect a center of the pivot joint.

The hand controller apparatus of any of preceding paragraphs and/or any of hand controller apparatuses described below can include one or more of the following features. The longitudinal axis of the control lever can be parallel to the longitudinal axis of the body when the control lever is in a closed position.

BRIEF DESCRIPTION OF THE DRAWINGS

Embodiments of the present disclosure will now be described hereinafter, by way of example only, with reference to the accompanying drawings in which:

FIGS. 21A and 21B illustrate conceptual diagrams showing an instrument clutch operation according to some embodiments;

DETAILED DESCRIPTION

Overview of Robotic Surgery System

Figure 1:
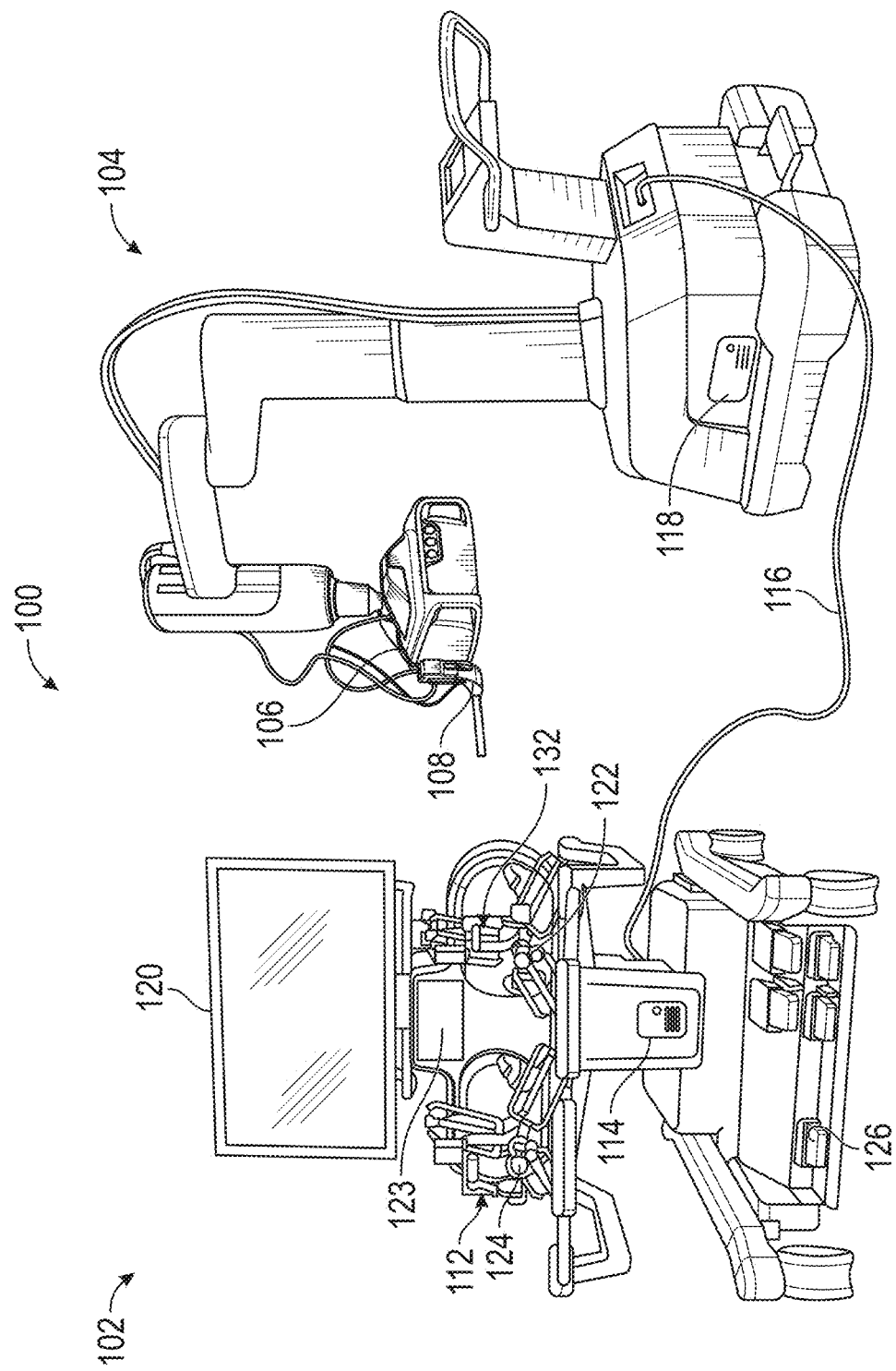
FIG. 1 illustrates a robotic surgery system in accordance with some embodiments.

FIG. 1 illustrates a robotic surgery system 100 in accordance with some embodiments. The robotic surgery system 100 includes a workstation 102 and an instrument station or a patient cart 104. The patient cart 104 includes at least one tool mountable on a moveable instrument mount, central unit or drive unit 106 that houses an instrument drive (not shown) for manipulating the tool. The tool may include an insertion device 108 configured to support at least one surgical instrument (hereinafter to be interchangeably used with an "instrument" or "surgical tool") and a camera (not shown) that images a surgical site. The workstation 102 may also include a tool such as an instrument clutch (that may be implemented by a foot pedal described below). The insertion device 108 can support two or more instruments (not shown). The camera may include a primary camera and at least one secondary camera. The primary camera and the secondary camera may provide different viewing angles, perform different functions and/or produce different images. At least one of the primary camera and the secondary camera may be a two-dimensional (2D) or a three-dimensional (3D) camera. FIG. 1 is merely an example of a robotic surgery system, and certain elements may be removed, other elements added, two or more elements combined or one element can be separated into multiple elements depending on the specification and requirements of the robotic surgery system.

The workstation 102 includes an input device for use by a user (for example, a surgeon; hereinafter to be interchangeably used with an "operator") for controlling the instrument via the instrument drive to perform surgical operations on a patient. The input device may be implemented using a haptic interface device available from Force Dimension, of Switzerland, for example. The input device includes a right input device 132 and a left input device 112 for controlling respective right and left instruments (not shown). The right input device 132 includes a right hand controller 122 (hereinafter to be interchangeably used with a "hand grip" or "handpiece") and the left input device 112 includes a left hand controller 124. The right and left hand controllers 122 and 124 may be mechanically or electrically coupled to the respective input devices 132 and 112. Alternatively, the right and left hand controllers 122 and 124 may be wirelessly coupled to the respective input devices 132 and 112 or may be wireless coupled directly to the workstation 102. In some cases, when there are two instruments at the instrument station 104, the right and left hand controllers 122 and 124 may respectively control the two instruments. In some cases, when there are more than two instruments, the right and left hand controllers 122 and 124 may be used to select two of the multiple instruments that an operator wishes to use. In some cases, when there is only one instrument, one of the right and left hand controllers 122 and 124 may be used to select the single instrument.

The input devices 132 and 112 may generate input signals representing positions of the hand controllers 122 and 124 within an input device workspace (not shown). In some cases where the input devices 132 and 112 are coupled directly and wirelessly to the workstation, they would include the necessary sensors to allow wireless control such as an accelerometer, a gyroscope and/or magnetometer. In other cases, a wireless connection of the input devices 132 and 112 to the workstation 102 may be accomplished by the use of camera systems alone or in combination with the described sensors. The afore described sensors for wireless functionality may also be placed in each handpiece to be used in conjunction with the input devices 132 and 112 to independently verify the input device data. The workstation 102 also includes a workstation processor circuit 114, which is in communication with the input devices 132 and 112 for receiving the input signals.

The workstation 102 also includes a display 120 in communication with the workstation processor circuit 114 for displaying real time images and/or other graphical depictions of a surgical site produced by the camera associated with the instrument. The workstation 102 may include right and left graphical depictions (not shown) displayed on the display 120 respectively for the right and left side instruments (not shown). The graphical depictions may be displayed at a peripheral region of the display 120 to prevent obscuring a live view of the surgical workspace also displayed on the display. The display 120 may further be operable to provide other visual feedback and/or instructions to the user. A second auxiliary display 123 may be utilized to display auxiliary surgical information to the user (surgeon), displaying, for example, patient medical charts and pre-operation images. In some cases, the auxiliary display 123 may be a touch display and may also be configured to display graphics representing additional inputs for controlling the workstation 102 and/or the patient cart 104. The workstation 102 further includes a footswitch or foot pedal 126, which is actuatable by the user to provide input signals to the workstation processor circuit 114. In one case, the signal provided to the workstation processor circuit 114 may inhibit movement of the instrument while the footswitch 126 is depressed.

The patient cart 104 includes an instrument processor circuit 118 for controlling the central unit 106, insertion device 108, one or more instruments and/or one or more cameras. In such case, the instrument processor circuit 118 is in communication with the workstation processor circuit 114 via an interface cable 116 for transmitting signals between the workstation processor circuit 114 and the instrument processor circuit 118. In some cases, communication between the workstation processor circuit 114 and the processor circuit 118 may be wireless or via a computer network, and the workstation 102 may even be located remotely from the instrument station 104. Input signals are generated by the right and left input devices 132 and 112 in response to movement of the hand controllers 122 and 124 by the user within the input device workspace and the instrument is spatially positioned in a surgical workspace in response to the input signals.

Figure 2:
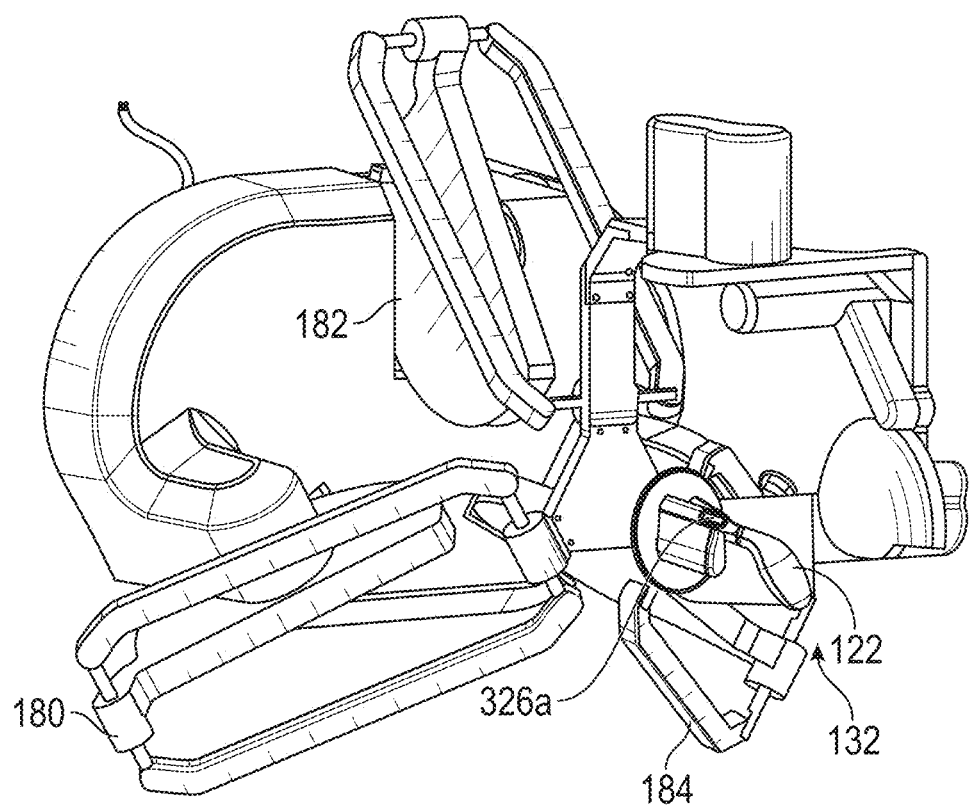
FIG. 2 illustrates a perspective view of a right side input device of the workstation shown in FIG. 1.

FIG. 2 illustrates a perspective view of the right side input device 132 of the workstation 102 shown in FIG. 1. Since the structure and operations of the right and left input devices 132 and 112 are substantially the same, the description will be provided only for the right side input device 132.

Furthermore, FIG. 2 illustrates only an example of an input device, input devices having other structures and shapes may also be used, as long as they receive a user's inputs for controlling the operation of the instrument. Referring to FIG. 2, the input device 132 includes three moveable arms 180, 182, and 184. The hand controller 122 may be coupled via a gimbal mount 186 to the moveable arms 180, 182, and 184. The input device 132 may include sensors (not shown) that sense the position of each of the arms 180, 182, and 184 and rotation of the hand controller 122 and produces signals representing a current position of the hand controller 122. In such case, the position signals are transmitted as input signals to the workstation processor circuit 114. The hand controller 122 may include a user actuatable button or input control interface 326a (see, for example, FIG. 3B), which may produce additional input signals for transmission to the workstation processor circuit 114.

Additional details of the robotic surgery system 100 including the hand controllers 122 and 124 are described in U.S. Patent Publication No. 2018/0168758, which is assigned to the assignee of the present application and the disclosure of which is incorporated by reference in its entirety.

Overview of Handpiece

Figure 3A:
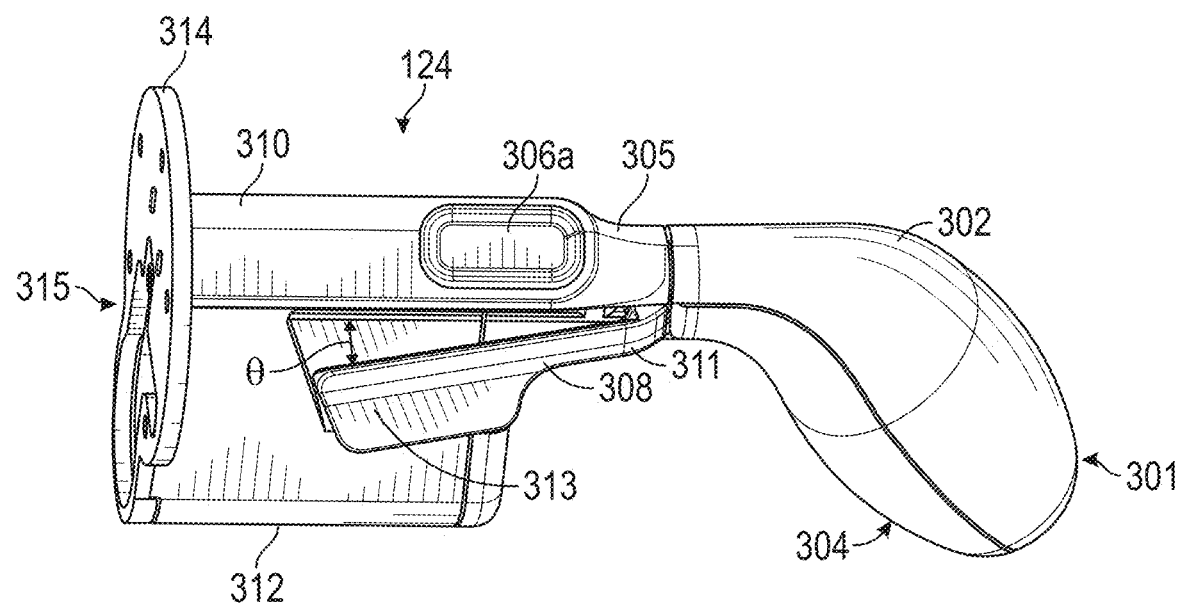
FIG. 3A illustrates a perspective view of a left side hand controller in an open position according to some embodiments.
Figure 3B:
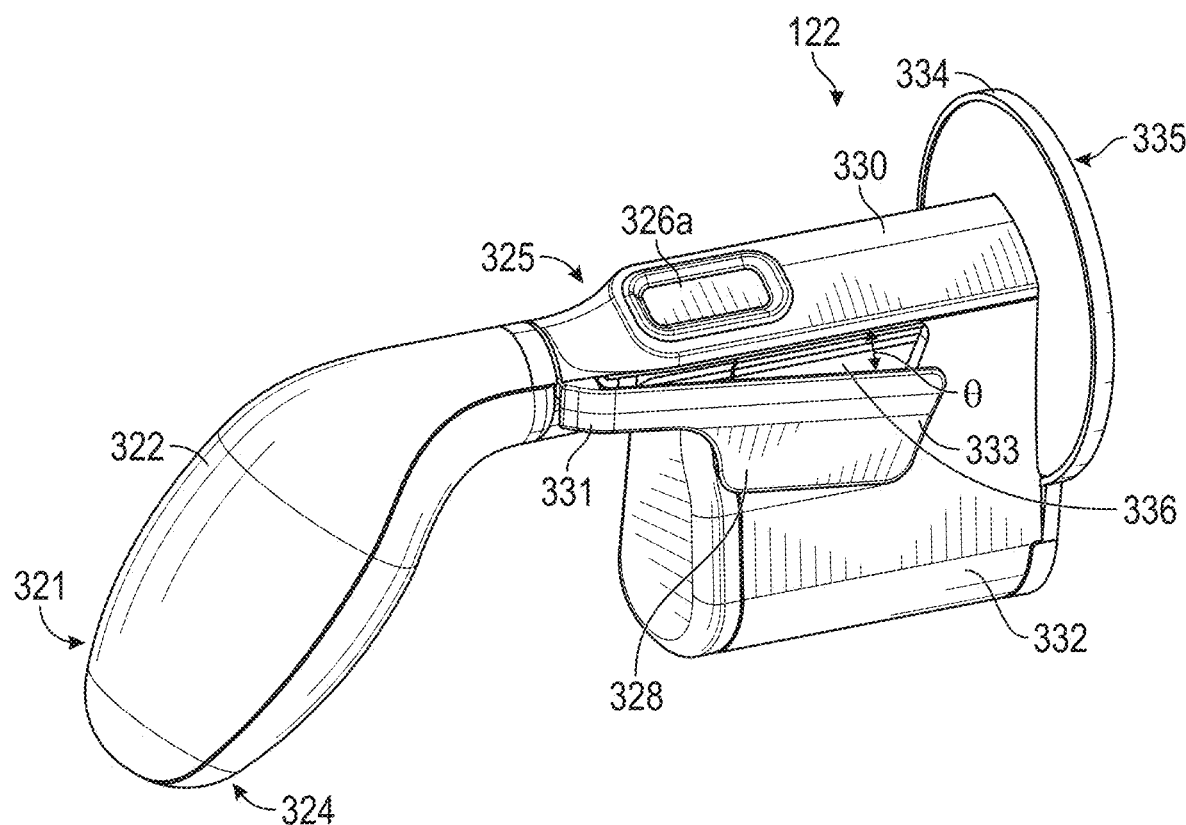
FIG. 3B illustrates a perspective view of a right side hand controller in an open position according to some embodiments.
Figure 4A:
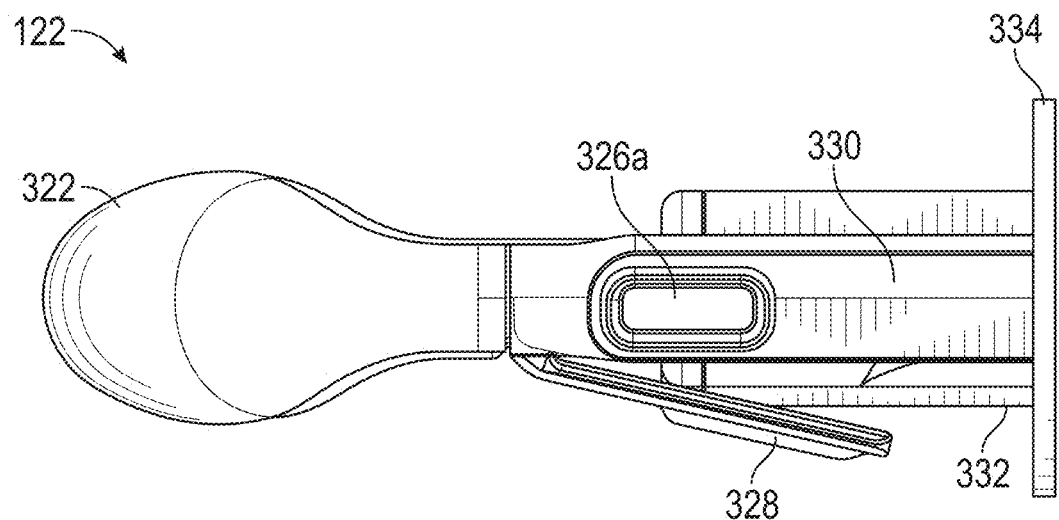
FIG. 4A illustrates a plan view of the hand controller of FIG. 3B according to some embodiments.
Figure 4B:
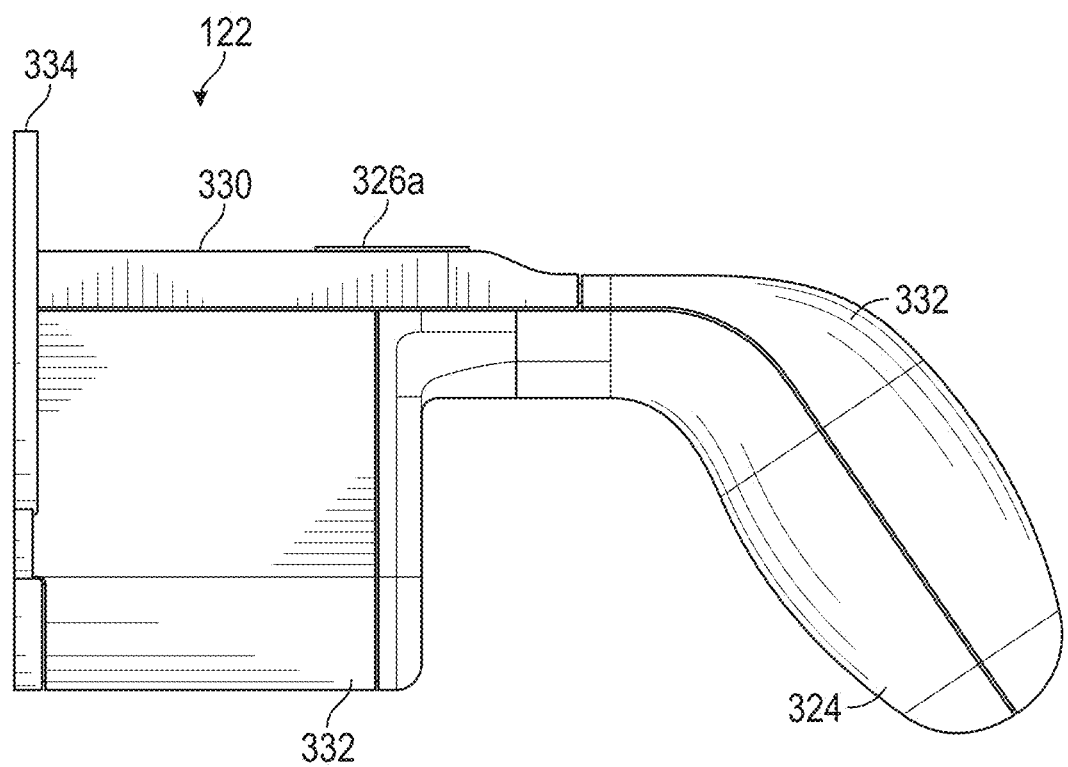
FIG. 4B illustrates a left side view of the hand controller of FIG. 3B according to some embodiments.
Figure 5:
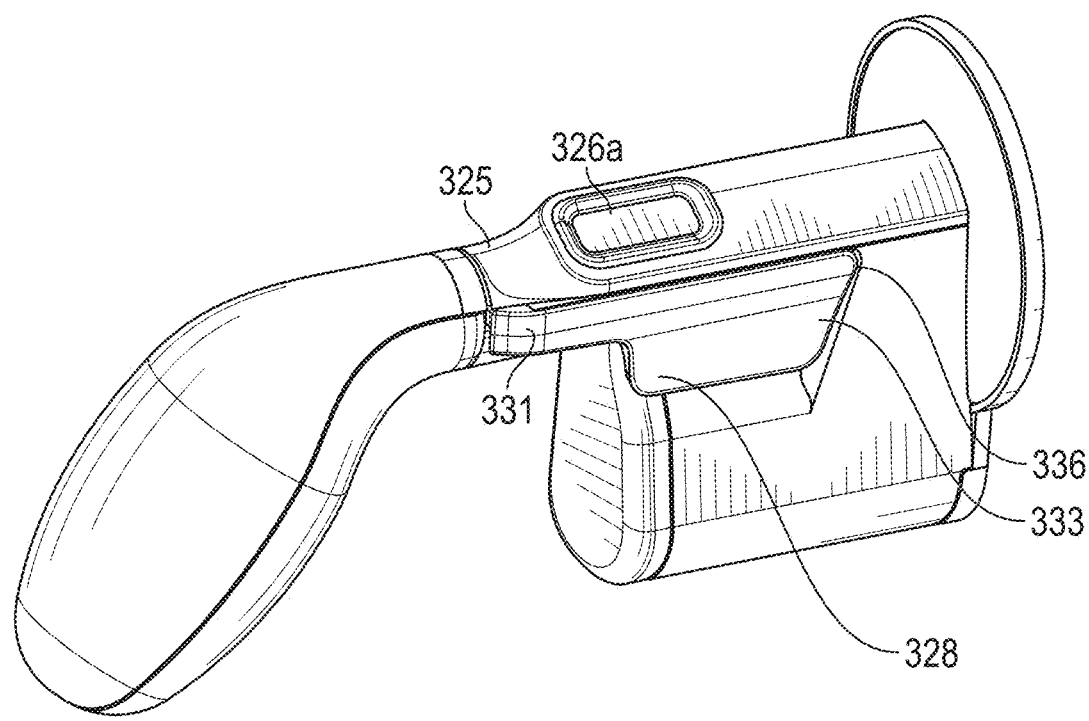
FIG. 5 illustrates a perspective view of a right side hand controller in a closed position according to some embodiments.

FIG. 3A illustrates a perspective view of a left side handpiece 124 in an open position according to some embodiments. FIG. 3B illustrates a perspective view of a right side handpiece 122 in an open position according to some embodiments. FIG. 4A illustrates a plan view of the handpiece 124 of FIG. 3B according to some embodiments. FIG. 4B illustrates a left side view of the handpiece 124 of FIG. 3B according to some embodiments. FIG. 5 illustrates a perspective view of a right side handpiece 122 in a closed position according to some embodiments. The handpieces 124 and 122 shown in FIGS. 3A to 5 can be used respectively as hand controllers for the input devices 112 and 132 shown in FIG. 1.

Each of the handpieces 124 and 122 shown in FIGS. 3A and 3B includes a single pincher 308/328 (hereinafter to be interchangeably used with "pincer," "paddle" or "control lever"). Each of the single paddle handpieces 124 and 122 may control the movement of one or a pair of jaws of a corresponding surgical instrument. The movement can include opening and/or closing of the one or more jaws. Thus, providing the single paddle handpieces 124 and 122 may be beneficial, as manufacturing costs can be reduced and their manufacturing procedure can be simplified. However, each handpiece may also include two pinchers (see, for example, FIG. 9). Furthermore, although FIG. 3A shows that the pincher 308 of the left side handpiece 124 is disposed on the left side of the body 305, the pincher 308 may be disposed on the right side of the body 305 (see, for example, FIG. 6A). Moreover, although FIG. 3B shows that the pincher 328 of the right side handpiece 122 is disposed on the right side of the body 325, the pincher 328 may be disposed on the left side of the body 325 (not shown).

Referring to FIG. 3A, the left side handpiece 124 includes a proximal end 301, an upper handpiece housing 302, a lower handpiece housing 304, a handpiece body 305, an input control interface 306a, a pincher 308 having a pivot point, a tail end 311 and a paddle end 313, an upper housing 310, a lower housing 312, a front plate (or connector) 314 and a distally located interface end 315. The proximal end 301 and the distally located interface end 315 may be part of the handpiece body 305.

Referring to FIG. 3B, the right side handpiece 122 includes a proximal end 321, an upper handpiece housing 322, a lower handpiece housing 324, a handpiece body 325, an input control interface 326a, a pincher 328 having a pivot joint 372 (see, for example, FIG. 11A), a tail end 331 and a paddle end 333, an upper housing 330, a lower housing 332 and a front plate 334, and a distally located interface end 335. The proximal end 321 and the distally located interface end 335 may be part of the handpiece body 325.

The handpiece 122 may be configured for operation by a right hand of the operator and the handpiece 124 may be configured for operation by a left hand. The left handpiece 124 may be configured as a mirror image of the right handpiece 122 as shown in FIGS. 3A and 3B, but may be differently configured depending on the nature of the task. For example, only one of the right and left handpieces 122 and 124 may include an input control interface. In such case, actuation on the single input control interface may perform input control for both of the handpieces 122 and 124. Furthermore, depending on the embodiment, at least one of the right and left handpieces 122 and 124 may include a plurality of input control interfaces. In some cases, the plurality of input control interfaces may have the same shape, function and/or structure. In some cases, the plurality of input control interfaces may have different shapes, functions and/or structures. Since the structure and operations of the right and left handpieces 122 and 124 are substantially the same, the description will be provided only for the right side handpiece 122.

The proximal end 321 of the right handpiece 122 may be shaped to be grasped by a right hand of an operator. Here, the proximal end 321 may include the handpiece housing 322 and 324. The proximal end 321 may also be referred to as a handle or a palm rest. The proximal end 321 may have a generally downwardly curved and rounded shape operable to receive and support a portion of the operator's palm when the body 325 is grasped in the hand of the operator. Although the upper and lower housings 322 and 324 appear to be as long as the remaining portion of the body 325, the present disclosure is not limited thereto. That is, the upper and lower housings 322 and 324 may be longer or shorter than the remaining portion of the body 325. The distally located interface end 335 may be configured for coupling to the input apparatus 132 for controlling the surgical tool associated with the robotic surgery system 100. At least a portion of the front plate 334 may be positioned in the distally located interface end 335.

Figure 11A:
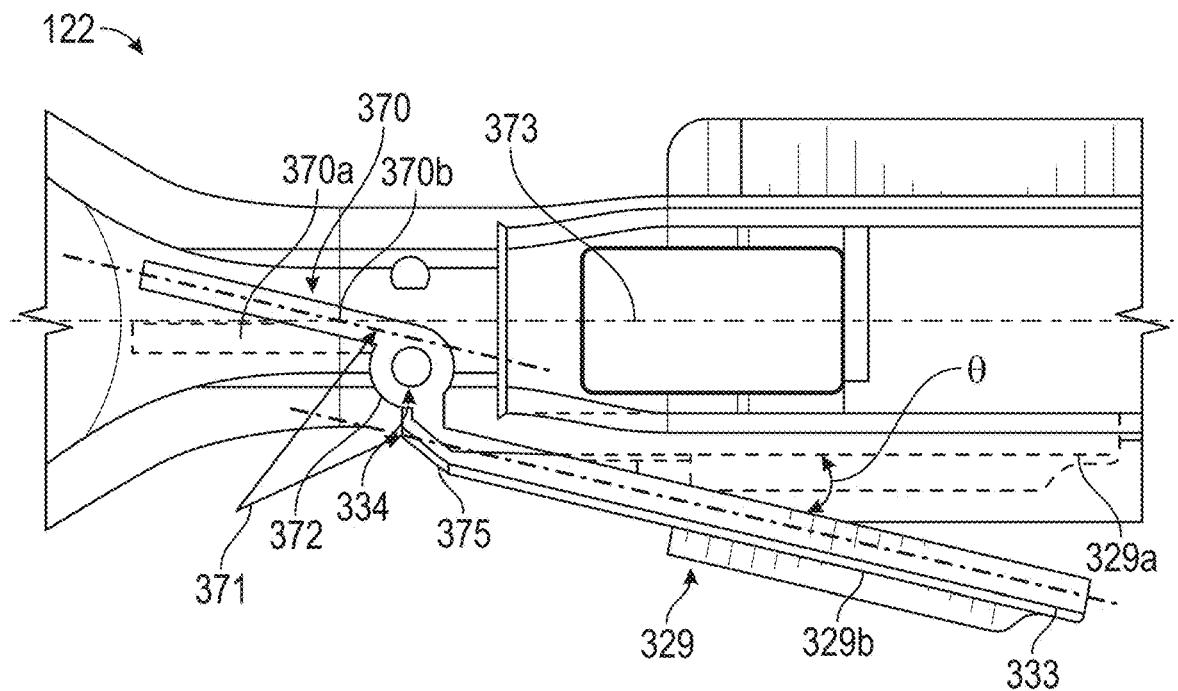
FIG. 11A illustrates a closed-up plan view of a hand controller pincher showing angular magnetic detection according to some embodiments.

The pincher 328 may be attached to the body 325 at the pivot joint 372 (see, for example, FIG. 11A). The pincher 328 may extend from the tail end 331 to the paddle end 333 along the body 325 to be away from the proximal end 321. FIG. 3B shows that the pincher 328 is in an open position. The open position means that the pincher 328 is opened by laterally moving away from the body 325 in a direction (for example, a clockwise direction) so that the pincher 328 forms an angle of θ (hereinafter referred to as a "pincher angle" or "pincer angle") with respect to a side surface of the body 325. For the left side handpiece 124, the pincher 313 is opened by laterally moving away from the body 305 in an opposite direction (for example, a counterclockwise direction) so that the pincher 308 has a pincer angle (θ) with respect to the body 305. In some cases, the pincer angle (θ) can be in the range of 0° to about 15°. In some cases, the pincer angle (θ) can be in the range of 0° to about 12.5°. By adjusting the pincer angle, the position or movement of the instrument can be adjusted in a highly accurate manner. In some cases, the maximum pincer angle (θ) can be greater or smaller than about 15°.

In some cases, the pincher 328 can be elastically moved between the open position and the closed position. In such cases, the pincher 328 may be configured to have the open position as an original or default position. The pincher 328 can restore to the original position via an elastic element such as a compression spring, when it is released by a user (see reference numeral 348 in FIG. 11B). When an operator desires to fix the position of the pincher 328 in a partially open position, the operator may be required to hold the pincher 328 in the specific open position with his or her finger. In some cases, a magnet or an electromagnet may be used in place of or in addition to the compression spring to fix the pincher 328 in a particular position and/or to provide a rebounding or resistive force to cause the pincher 328 return to an open position upon being actuated/closed. Furthermore, the movement of the pincher 328 may be controlled by a processor so that the pincher 328 is fixed in a partially open position without the operator's finger holding the pincher 329 at the position. In such cases, the pincher 328 may be caused to remain in a particular position by varying the amount of electromagnetic force being delivered. Varying the electromagnetic force being delivered may also be used to provide a resistive or feedback force on the pincher 328 on the operator's finger placed on the pincher 328 or as the operator tries to actuate the pincher 328. In some cases, the pincher 328 can be non-elastically (for example, mechanically) moved between the open position and the closed position by pressing the tail end 331 of the pincher 328 or by pulling the paddle end 333 away from a side surface of the body 325 for example, in a clockwise direction. In such cases, the pincher 328 may be fixed in a partially open position without the operator's finger holding the pincher 328 at that position.

When the pincher 328 is laterally moved in the workstation 102, the processor circuit 114 generates and transmits a control signal to the patient cart 104 such that one or both of the jaws of the instrument are simultaneously opened or closed accordingly based on the control signal. For example, if the pincer angle (θ) is small, the one or more jaws of the instrument are opened in a correspondingly small amount. Furthermore, if the pincer angle (θ) is large, the one or more jaws of the instrument are opened in a correspondingly large amount.

The pincher 328 may be accommodated in a cutout 336 in a closed position where the pincer angle is generally 0° (see, for example, FIG. 5). The cutout 336 may include a recess, an indentation or a groove. The pincher 328 may be received in the cutout 336 such that a surface of the pincher 328 facing the body 325 is generally contiguous with side surfaces of the body 325 when the pincher 328 is in the closed position. In some cases, the handpiece 122 may not include a cutout portion, and the paddle end 333 of the pincher 328 contacts the body 325 in a closed position where the pincer angle is generally 0°.

The input control interface 326a may be positioned on an upper surface of the body 325. An operator may perform a primary control of repositioning the input devices or actuating actuators to control end-effectors (for example, one or more jaws) of the instruments. An additional control or secondary control (other than the primary control) may be performed using the input control interface 326a. For example, the input control interface 326a may be used to receive additional user inputs such as camera control or instrument clutch, that may be difficult for an operator to provide a user input with the handpieces or foot pedal particularly while the operator is moving the handpieces. The additional user inputs may also include controlling tool functions (to be described later), controlling paddle movements, and/or selecting particular instruments when there are more than two surgical instruments. The input control interface 326a may be generally horizontally aligned with at least a portion of the pincher 328. The input control 326a may be a PCB slider having an actuator surface or an input control interface (to be described below in greater detail). The input control interface 326a may be slightly inclined toward a side of the body 325 where an operator's index finger would be located when the operator grasps the handpiece. A detailed structure of a handpiece having an inclined input control interface is described in U.S. Patent Publication No. 2018/0168758, which is incorporated by reference in its entirety.

Operation of Handpiece

Figure 6A:
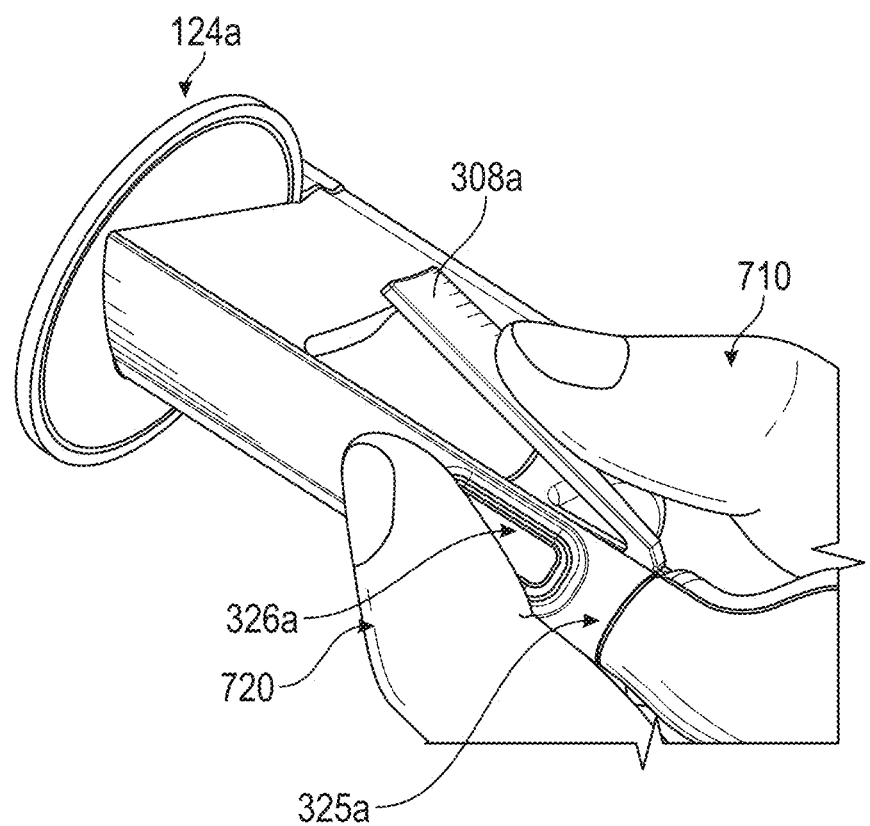
FIG. 6A illustrates a perspective view of a left side hand controller grasped by a user's left hand according to some embodiments.
Figure 6B:
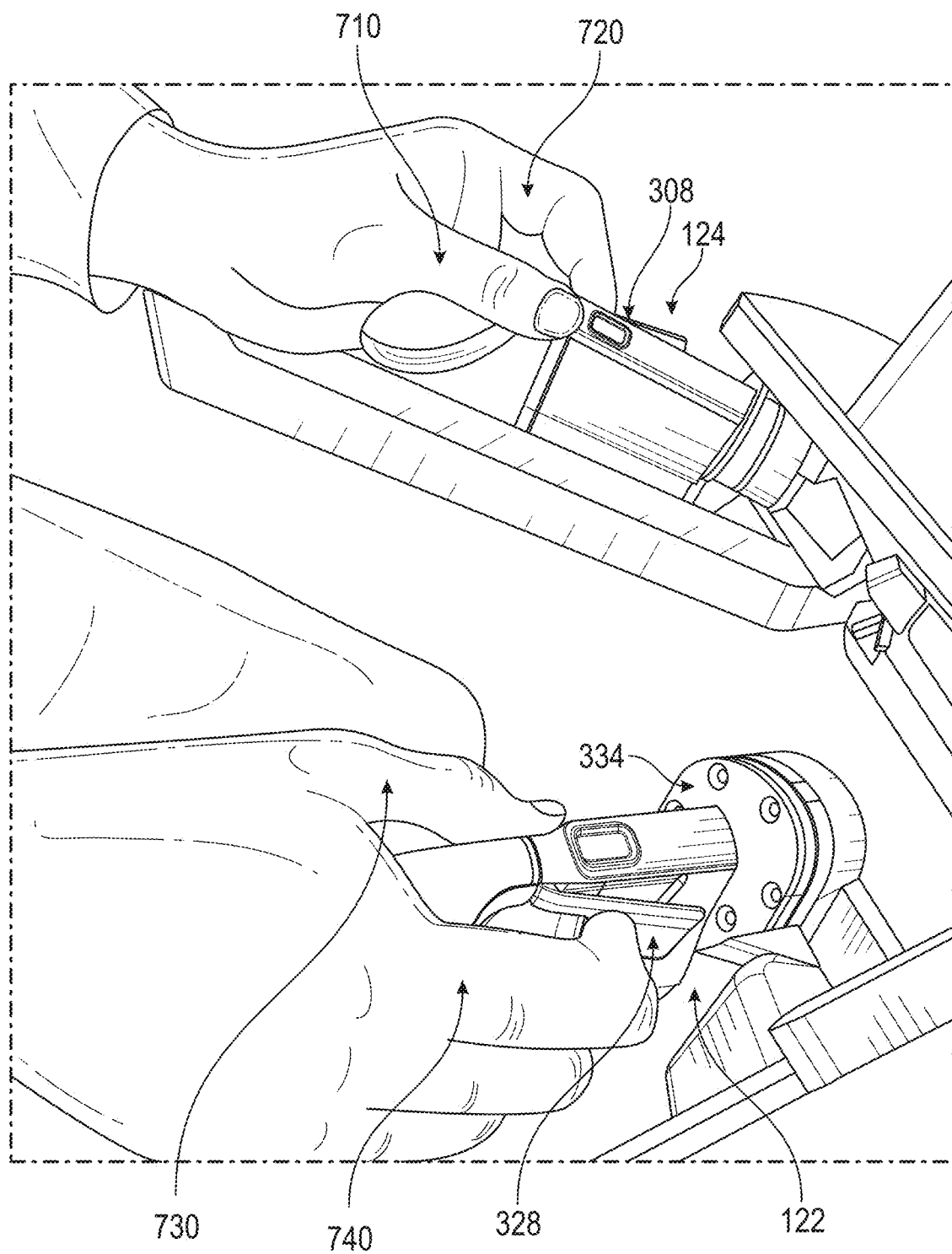
FIG. 6B illustrates a perspective view of left and right side hand controllers grasped by a user's hands according to some embodiments.

FIG. 6A illustrates a perspective view of a left side handpiece 124a grasped by a user's left hand according to some embodiments. FIG. 6B illustrates a perspective view of left and right side handpieces 124 and 122 grasped by a user's hands according to some embodiments.

Referring to FIG. 6A, a pincher 308a of the handpiece 124a is disposed on the right side of a body 325a. In such case, a user's left thumb 710 can be positioned on the pincher 308a of the handpiece 124a to close or open the pincher 308a. Furthermore, the remaining four fingers may be positioned on the left side of the body 325a. A user's index finger 720 may be positioned on the top surface of the body 325a to actuate the input control interface 326a.

Referring to FIG. 6B, the left side handpiece 124 is grasped by a user's left hand, whereas the right side handpiece 122 is grasped by a user's right hand. The operator's left index finger 720 is shown operating the left pincher 308 (partially shown) whereas the operator's thumb 710 is shown grasping the body 325 of the handpiece 124. Furthermore, the operator's right index finger 740 is shown operating the right pincher 328 whereas the operator's thumb 730 is shown grasping the body 325 of the handpiece 122. The operator can open and close the left and right pinchers 308 and 328 by making pincher movements (for example, by pressing the respective paddle ends 313 and 333) with the index fingers respectively.

The left handpiece 124 may be rotated by a user's left hand. Furthermore, the right handpiece 122 may be rotated by a user's right hand about the center of the front plate 334. For the left hand piece 124, a user's thumb 710 and a portion of a user's palm may grasp or support the handpiece 124, whereas one of the index finger 720, middle, ring and pinky fingers can be used to operate the pincher (not shown), for example, via a fingertip. Similarly, for the right hand piece 122, a user's thumb 730 and palm may grasp or support the handpiece 122, whereas one of the index finger 740, middle, ring and pinky fingers can be used to operate the pincher 328 (not shown), for example, via a fingertip. The pincher 308 of the left handpiece 124 and the pincher 328 of the right handpiece 122 may be sized such that when grasped by the hand of an average operator, the fingertips on the respective pinchers are positioned to receive distal phalanges of the operator's finger 720/740 and thumb 710/730.

The single control lever 328 of the right handpiece 122 may produce a control signal for the right input device 132 configured to simultaneously move one or a pair of jaws of a corresponding surgical tool. Furthermore, the single control lever 308 of the left handpiece 124 may produce a control signal for the left input device 112 configured to simultaneously move one or a pair of jaws of a corresponding surgical tool.

Additional Handpiece Examples

Figure 7:
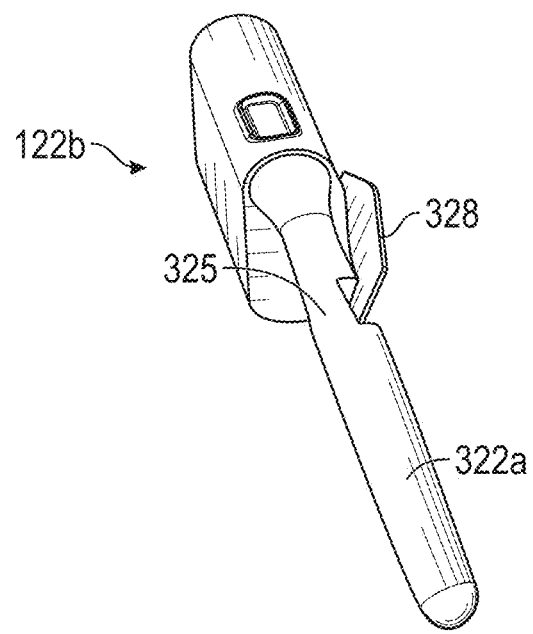
FIG. 7 illustrates a perspective view of a right side hand controller in an open position according to some embodiments.

FIG. 7 illustrates a perspective view of a right side handpiece 122b in an open position according to some embodiments. The handpiece 122b of FIG. 7 has a different shape compared to the previous handpiece examples. For example, the handpiece 122b has a relatively long and substantially linear housing 322a. Furthermore, the handpiece 122b has a pincher 328 disposed near the top of a body 325. The handpiece 122b has a paddle with a relatively narrower width (measured in a longitudinal direction of the handpiece).

Figure 8:
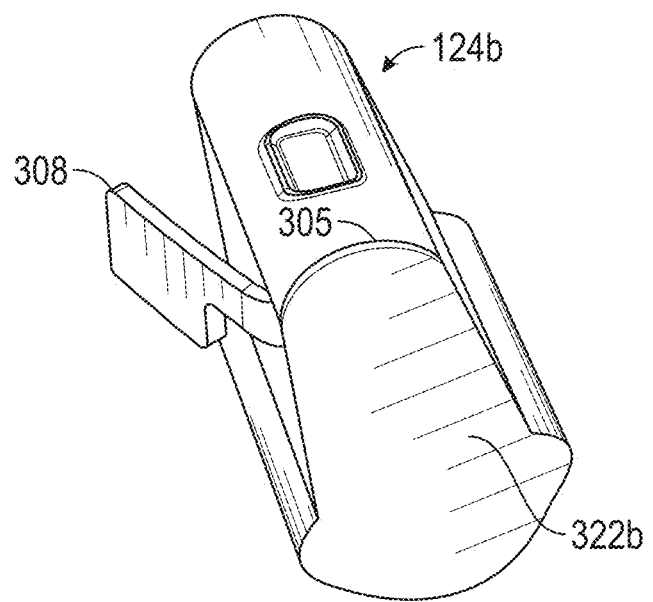
FIG. 8 illustrates a perspective view of a left side hand controller in an open position according to some embodiments.

FIG. 8 illustrates a perspective view of a left side hand controller 124b in an open position according to some embodiments. The handpiece 124b of FIG. 8 has a different shape compared to the previous handpiece examples. For example, a portion of the body 305 and a portion of a housing 322b are cut. Thus, the housing 322b is relatively short. The housing 322b is also generally linear.

Figure 9:
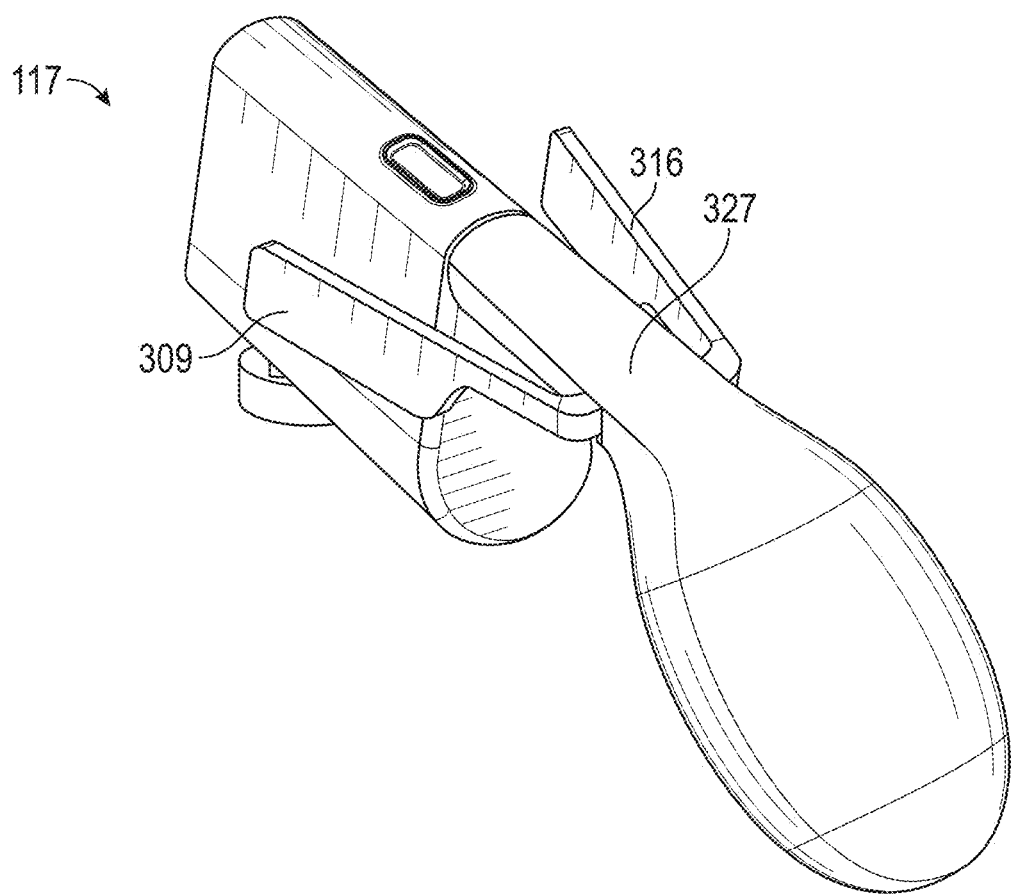
FIG. 9 illustrates a perspective view of a hand controller having two pinchers in an open position according to some embodiments.

FIG. 9 illustrates a perspective view of another handpiece 117 in an open position according to some embodiments. The hand controller 117 includes two pinchers 309 and 316 respectively disposed on the left and right sides of the body 327. In such case, as the pinchers 309 and 316 are opened and closed, one or a pair of jaws of the instrument are opened and closed. A detailed operation of a two pincher handpiece is described in U.S. Patent Publication No. 2018/0168758, which is incorporated by reference in its entirety.

It is appreciated that the handpieces shown in FIG. 3A to FIG. 9 are merely examples and the present disclosure is not limited thereto. For example, it is possible to provide many other handpieces including one or more of the following variations: different body shapes, different pincher shapes or dimensions, different numbers of pinchers, different positions, shapes or numbers of input control interfaces, and/or different positions of other handpiece elements may also be possible.

Assembly of Handpiece

Figure 10:
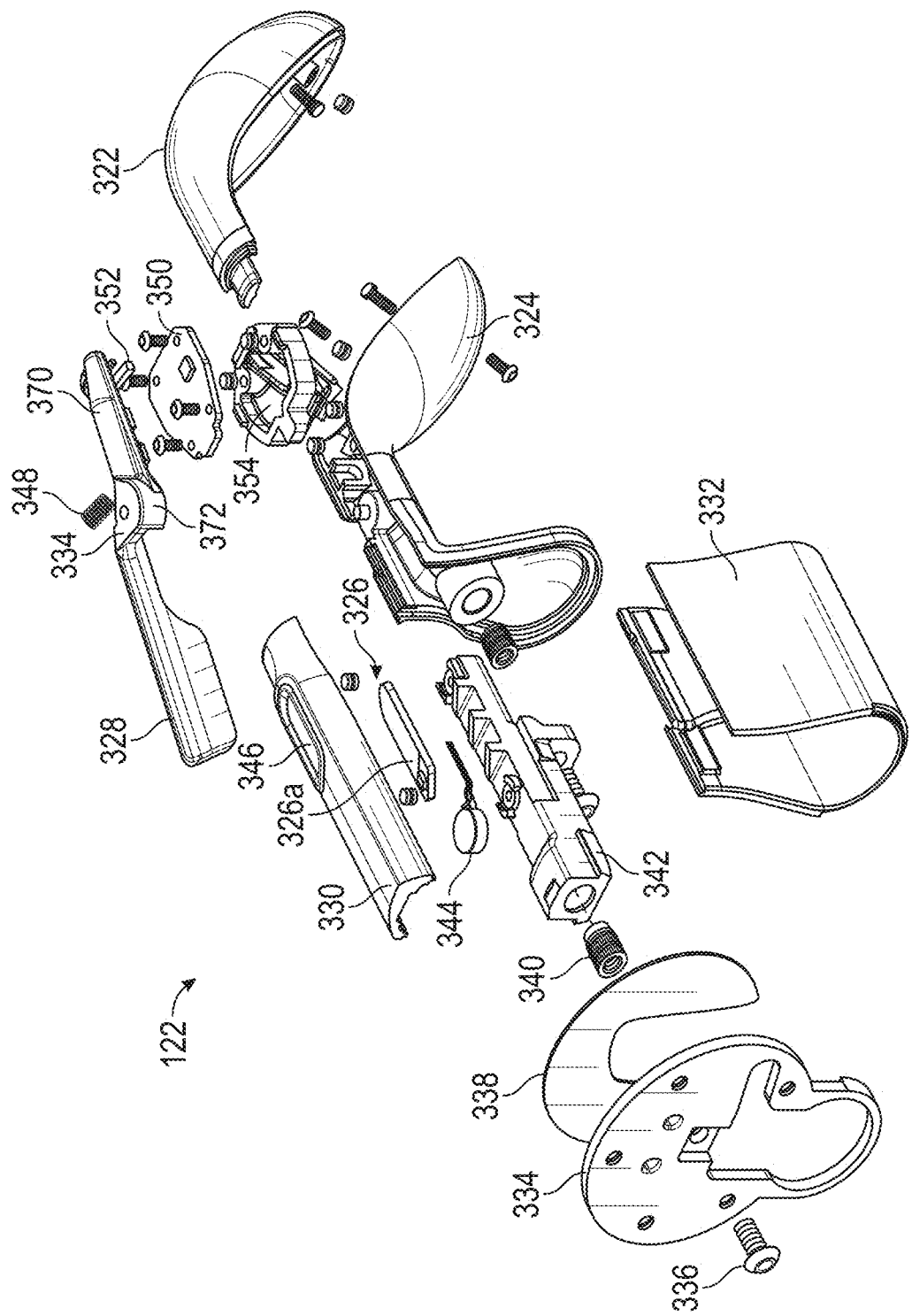
FIG. 10 illustrates an assembly view of the hand controller of FIG. 3B according to some embodiments.

FIG. 10 illustrates an assembly view of the handpiece 122 of FIG. 3B according to some embodiments. FIG. 10 is merely an example assembly view of the handpiece 122, and certain elements may be removed, other elements added, two or more elements combined or one element can be separated into multiple elements depending on the specification and requirements of the handpiece. Referring to FIG. 10, the upper and lower handpiece housings 322 and 324 accommodate a first PCB 350, a first PCB carrier 354, a wiper (or extension or inner paddle) 370, a bar magnet (hereinafter to be interchangeably used with a "magnet," "magnetic portion," or a "magnetic target") 352, a compression spring 348 and a pivot joint 372. The upper and lower housings 330 and 332 accommodate a center mount 342, a vibration motor (or a haptic actuator) 344 and a second PCB 326. The upper housing 330 has an opening 346 that accommodates and exposes a top surface of the second PCB 326. The front plate 334 and a front plate label 338 are connected to the center mount 342 via a screw 336 and a threaded insert 340.

The first PCB 350 may include a pincer angle detector and/or a presence detector (to be described in greater detail below). The first PCB 350 may also include a handpiece feedback control device (to be described later). The first PCB holder 354 accommodates the first PCB 350. The bar magnet and/or the compression spring 348 can also be used to detect a pincer angle in connection with the pincer angle detector as described herein. The pincher 328 may be rotatably fixed to an interior portion of the upper and lower handpiece housings 322 and 324 via a pin (not shown) inserted into a pin hole 334 of the pivot joint 372. For example, the pincher 328 may rotate laterally from a side portion of the body 325 about the pivot joint 372.

The second PCB 326 may include an IC for driving a trackpad or a capacitive touch surface 326a for user input and gesture control (to be described in greater detail below). The trackpad or capacitive touch surface may be positioned on the top surface of the second PCB 326. The second PCB 326 may also include one or more of the pincer angle detector, the presence detector or the handpiece feedback control device. The vibration motor 344 may be mounted on the center mount 342. However, the vibration motor 344 may be located in other positions inside the handpiece 122. The vibration motor 344 can be used for providing a haptic feedback to an operator (to be described in greater detail below).

Paddle Actuation Sensing/Pincer Angle Detection

As described herein, the pincher or paddle moves between a closed position and an open position. The open position includes a partially open position and a completely open position. The paddle would form a pincer angle with respect to a side surface of the handpiece body facing the paddle. In some cases, the pincer angle is the minimum at the closed position and the maximum at the completely open position. In operation, the pincer angle would be between the minimum and maximum at a partially open position. As the paddle moves from a closed position to a partially or completely open position, the one or more jaws of the surgical instrument also move to correspond to the movement of the paddle. Furthermore, as the paddle moves from the open position to the closed position, the one or more jaws of the surgical instrument also move to correspond to the movement of the paddle. Thus, it is advantageous to sense or detect an accurate position of the paddle or a pincer angle in order to more precisely control the movement of the surgical instrument.

Pincer angle detection or paddle actuation sensing can be done in various ways. In some cases, pincer angle can be detected by magnetically or inductively sending a movement of a metallic portion or target disposed in the wiper or paddle. For example, a magnetic angular detector, an inductive/eddy current detector or proximity sensor can be used for pincer angle detection. However, other detection methods can also be used as long as they can detect a position of the paddle or a pincer angle with respect to the body, or distance between the paddle and the body. Although the pincer angle detection or paddle actuation sensing is described in connection with one paddle handpiece, it can be applied to a handpiece having two paddles. In such cases, since the two paddles of the handpiece would move symmetrically, pincer angle detection for only one of the paddles may be sufficient to control the movement of the surgical instrument.

1. Magnetic Angular Detector for Detecting Wiper Movement

This method detects an angular movement of a magnetic portion or target that moves, when a pincher laterally moves with respect to a side surface of the handpiece body. In some cases, the magnetic target can be attached to and move along with the wiper, when the pincher laterally moves with respect to the side surface of the body. In some cases, at least a portion of the wiper can be a magnetic target. For example, a part or the entirety of the wiper can be formed of a magnetic material. In such cases, no separate magnet is required. Magnetic angle detection may provide several advantages over magnetic strength detection, primarily because angle does not drift with time or temperature (unlike strength).

Figure 11B:
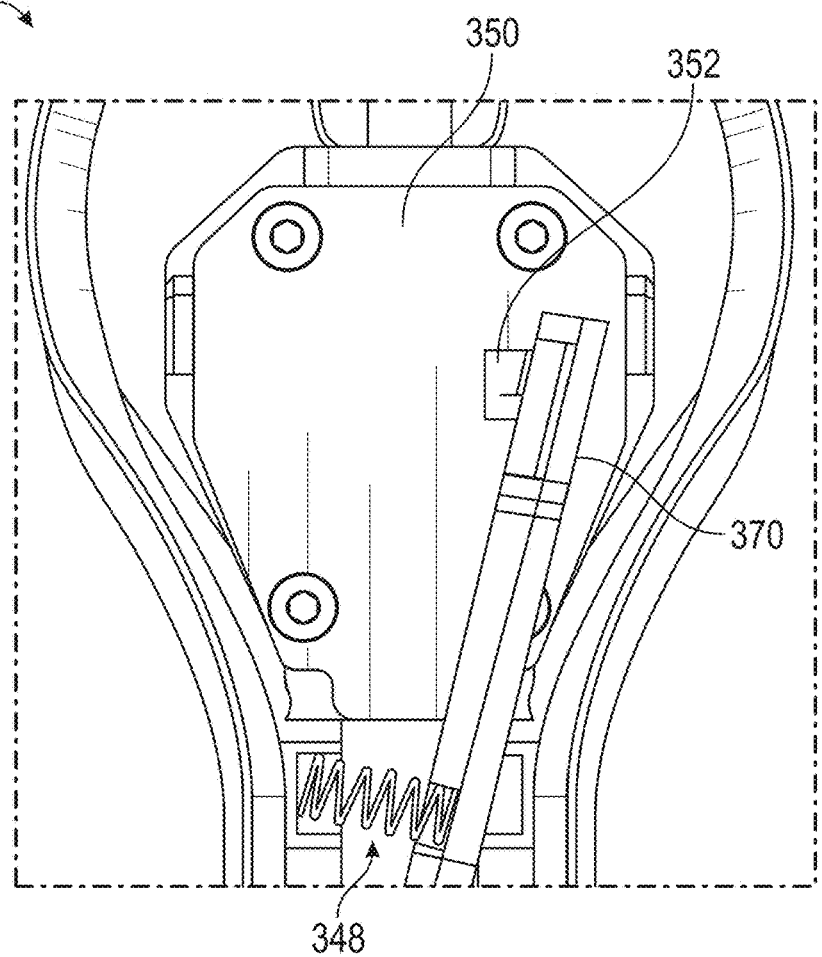
FIG. 11B illustrates a closed-up plan view of a hand controller wiper and a magnetic angular detector according to some embodiments.

FIG. 11A illustrates a close-up plan view of the pincher 328 showing magnetic angular detection according to some embodiments. FIG. 11B illustrates a close-up plan view of the wiper 370 and a magnetic angular detector according to some embodiments. The pincher 328 includes a paddle 329 disposed outside the body 325 and a wiper 370 disposed inside the body 325. Referring to FIG. 11A, the paddle 329 laterally moves between a closed position 329a and an open position 329b so that the paddle 329 forms a pincer angle (θ) with respect to a surface of the handpiece body facing the paddle 329. As the paddle 329 laterally moves between the closed position 329a and the open position 329b, the wiper 370 moves in an opposite direction between a substantially parallel position 370a and an angled position 370b as shown in FIG. 11A. When the paddle 329 and the wiper 370 move in opposite directions, the two pincher elements 329 and 370 maintain a substantially parallel and spaced-apart relationship with respect to each other as indicated by two parallel dotted lines 371 in FIG. 11A. In some cases, the paddle 329 and the wiper 370 may not be substantially parallel but would maintain a spaced-apart relationship. The paddle 329 and the wiper 370 may elastically move between the open position and the closed position via the compression spring 348 disposed inside the handpiece body or by other appropriate means, for example as described above.

In the closed position, the pincer angle (θ) may be generally zero, as the paddle 329 would contact the side surface of the handpiece body 325. In the completely open position, the pincer angle (θ) may be about 12.5° to about 15°. Thus, the paddle 329 may move between the pincer angles in the range of 0° to 15°. However, the maximum pincer angle can be less than or greater than about 15° depending on the embodiment. The wiper 370 may generally form the same angle between the two positions 370a and 370b as the pincer angle, as the wiper 370 and the paddle 329 are fixed relative to each other.

In some embodiments, the magnet or magnetic target 352 may be attached to the wiper 370. In such cases, the wiper 370 may or may not be formed of a metallic material, as long as the magnet 352 can be attached to the wiper 370, for example, via adhesive. In some cases, the wiper 370 may be formed at least partially of a magnetic material. For example, a portion of the wiper 370 may be a magnet or the entirety of the wiper 370 can be a magnet. In such cases, no separate magnetic target needs to be attached to the wiper 370.

The first PCB 350 may include a magnetic angular detector configured to detect an angular movement of the magnetic target 352 that rotates or laterally moves along with the wiper 370 about the pivot joint 372 (ergonomic features of the pivot joint and paddle design to be described at the "Handpiece Ergonomic Features" section later). In some cases, the magnetic angular detector can be implemented with, for example, integrated circuits (ICs) available from Monolithic Power Systems Inc. (MPS). The MPS ICs generally detect the absolute angular position of a permanent magnet, typically a diametrically magnetized cylinder on a rotating shaft. The MPS ICs can be tunable and can provide a robust solution. For example, the MPS ICs may achieve greater than about 9 bits of resolution over the 12.5° range of the pincer angle.

In some cases, the magnetic angular detector can be implemented with, for example, ICs available from Analog Devices Inc. (ADI). The ADI ICs can be an anisotropic magnetoresistive (AMR) sensor with integrated signal conditioning amplifiers and ADC drivers that can produce two analog outputs indicating the angular position of the surrounding magnetic field.

MPS ICs and ADI ICs are merely example magnetic angular detectors that realize the magnetic angular detection, and other magnetic angular detecting circuits can also be used as long as they can detect an angular movement of a magnet attached to or integrally formed with the wiper 370. In some cases, the magnet 352 may include rare earth magnets. Rare earth magnets generally decay at a rate of less than 1% per decade. In some cases, any magnet could be used for the magnet 352.

2. Inductive/Eddy Current Detector

This method uses the concept of inductive or eddy current that is induced at an inductive coil when a metallic target moves over the coil. In some cases, the metallic target may be disposed in or integrally formed with the wiper, and move in an arced or curved path over the inductive coil disposed inside or outside the wiper. In some cases, the metallic target may be attached to or integrally formed with the paddle, and move in an angled path with respect to the inductive coil. For the purpose of convenience, the description will be made for the metallic target which is attached to either the wiper or the paddle (instead of being integrally formed with the wiper or the paddle). The inductive/eddy current detector is different from the magnetic angular detector in that the former does not require the use of a magnet. This method is also inherently resilient to outside electro-magnetic interference, as no magnet is required.

A. Inductive/Eddy Current Sensor for Detecting Target in Wiper

Figure 12A:
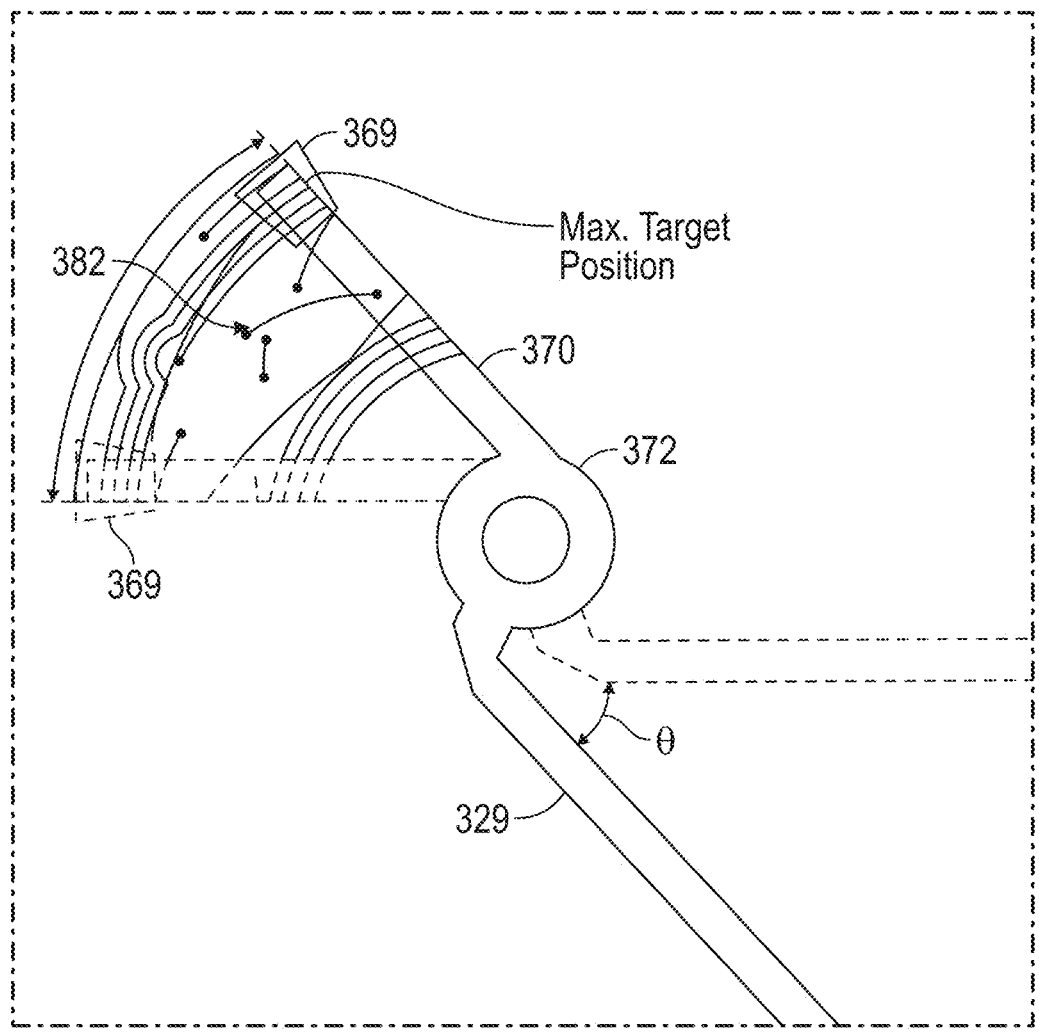
FIG. 12A illustrates a conceptual diagram showing a magnetic angular detection method for a metallic portion in a wiper according to some embodiments.

FIG. 12A illustrates a conceptual diagram showing an angular magnetic detection method for a metallic portion or target 369 disposed in the wiper 370 according to some embodiments. The first PCB 350 shown in FIG. 11B may include an inductive detector that can detect a metallic target (or metallic portion) moving in an arced path with respect to an inductive coil disposed in the first PCB 350. In some cases, the first PCB 350 may include both the magnetic angular detector and the inductive detector. In some cases, a separate PCB may be used to accommodate the inductive sensor.

The operation of an inductive detector for detecting a metallic target 369 at the wiper 370 is described with respect to FIG. 12A. The inductive detector may detect a curved or arced movement of the metallic target 369, when the paddle 329 moves laterally from side portion of the body 325. Referring to FIGS. 11A and 12A, the wiper 370 and the metallic target 369 move in a curved path between the two positions 370b and 370a over a curved PCB coil layout 382 of the inductive detector, as the paddle 329 moves in a curved direction opposite to the curved path of the wiper 370. The curved PCB coil layout 382 may be manufactured by bending a linear PCB coil layout into an arc track during PCB layout. The linear PCB track can be shaped to suit whatever path a metallic target takes.

The metallic target 369 disposed in the wiper 379 may move on substantially the same plane (or substantially parallel planes) as the plane on which the curved PCB coil layout 382 is positioned (for example, substantially coplanar). In some cases, to allow for different shapes of hand pieces, the metallic target 369 disposed in the wiper 379 may move on a different plan as the plan on which the curved PCB coil layout 382 is positioned. Therefore, the metallic target 369 can track the curved PCB coil layout 382, as the wiper 370 moves in the curved path. As the metallic target 369 moves over the curved PCB coil layout 382, electrical current is induced at the curved PCB coil layout 382. The metallic target 369 may have a trapezoidal shape as shown in FIG. 12A to more closely track the curved path over the curved PCB coil layout 382.

In some cases, the PCB coil layout 382 may include one transmitter coil and two receiver coils in different paths. The inductive sensor may demodulate and process secondary voltages received at the receiver coils, and obtain a signal representing the metallic target's position. The inductive sensor can be implemented with, for example, ICs available from Integrated Device Technology, Inc. (IDT). The IDT ICs can compare voltage values received at two receiver coils, combine this comparison with the knowledge of their different paths, and may cancel out certain mechanical tolerances (for example, even if the metal target were a bit off angle and it would not severely impact the result).

B. Inductive/Eddy Current Sensor for Detecting Target in Paddle

The pincer angle may be detected by inductively sensing a movement of a metallic target disposed in the paddle. In some cases, the movement of the metallic target in the paddle may be sensed by a linear coil inductive sensor. In some cases, the movement of the metallic target in the paddle may be sensed by a spiral-shaped coil inductive sensor.

a. Linear Coil Inductive Detector

Figure 12B:
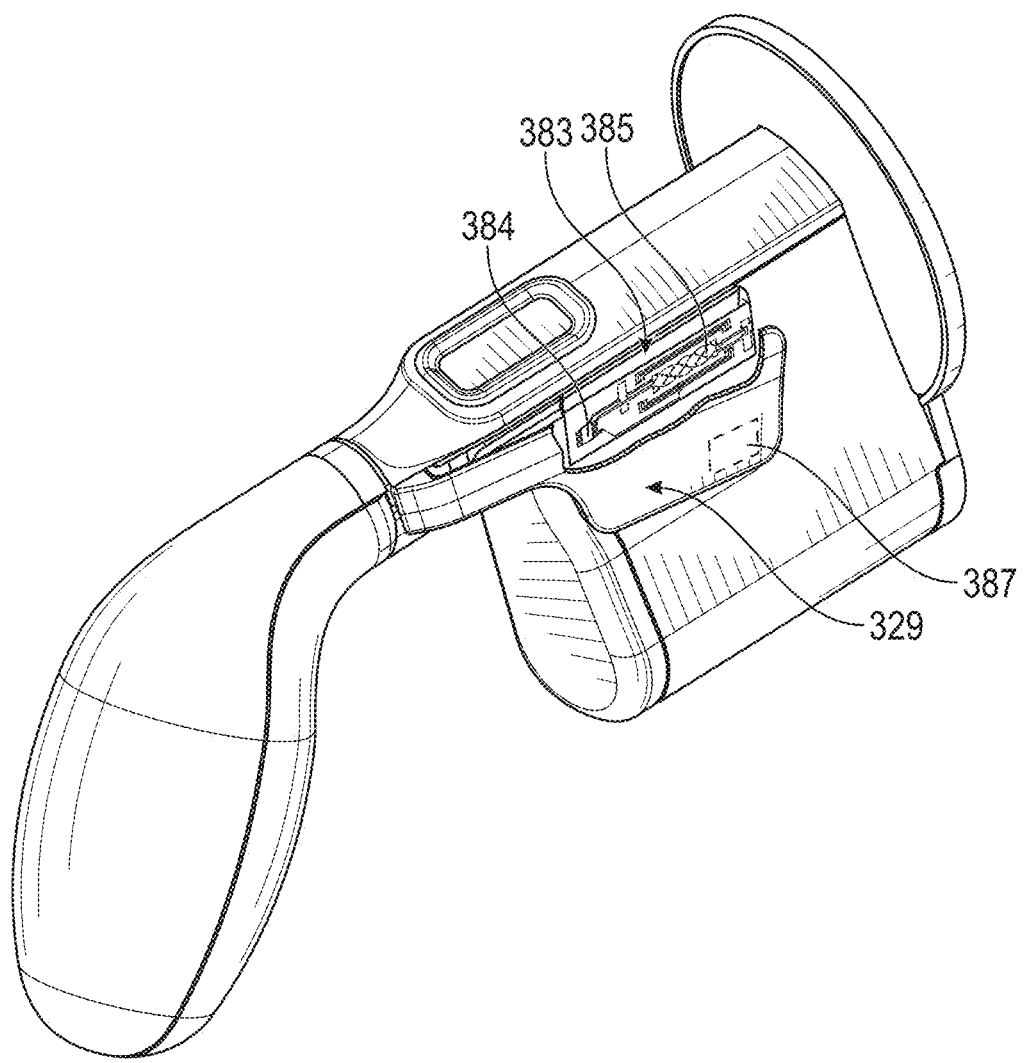
FIG. 12B illustrates a perspective view of a hand controller including a linear coil inductive detector for sensing movement of a metallic portion in the paddle according to some embodiments.
Figure 12C:
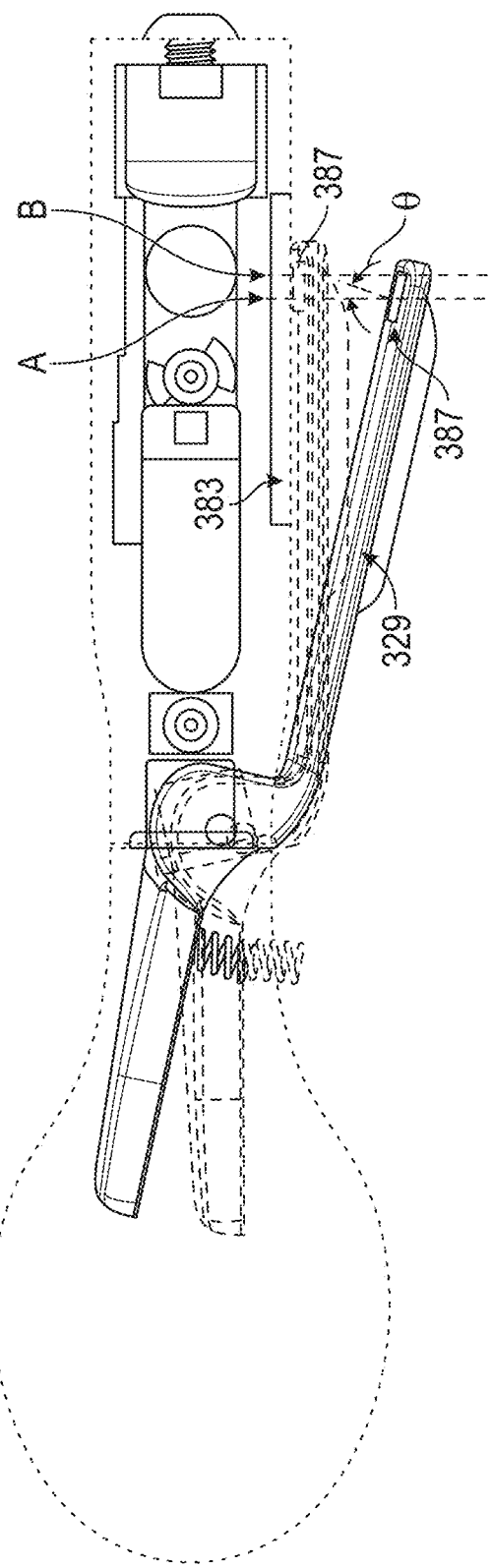
FIG. 12C illustrates a plan view of the hand controller including the linear coil inductive detector of FIG. 12B.
Figure 12D:
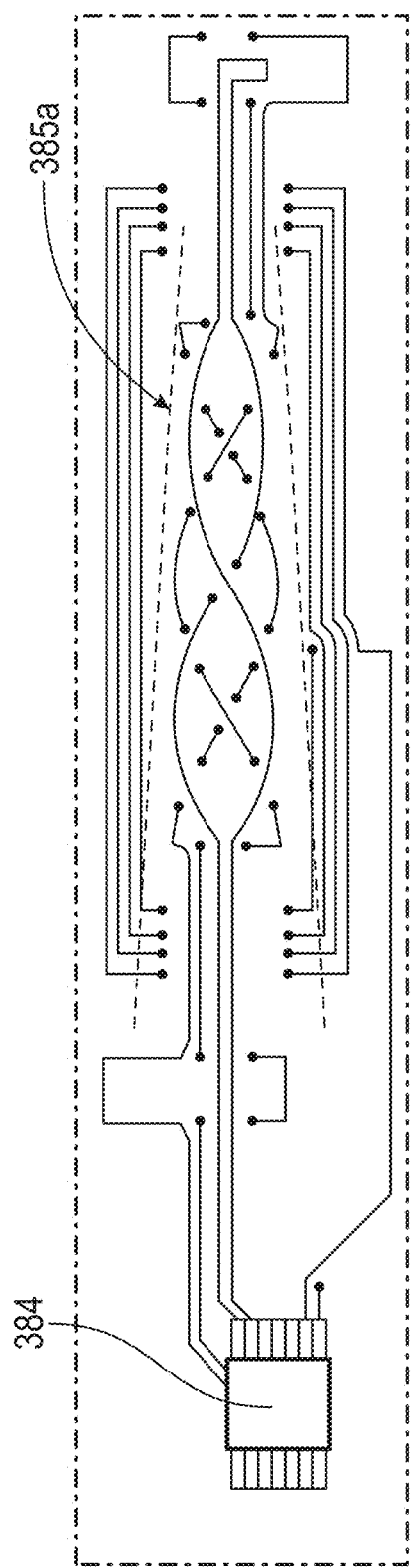
FIG. 12D illustrates a modified printed circuit board (PCB) coil layout for the linear inductive detector shown in FIGS. 12B and 12C according to some embodiments.
Figure 12E:
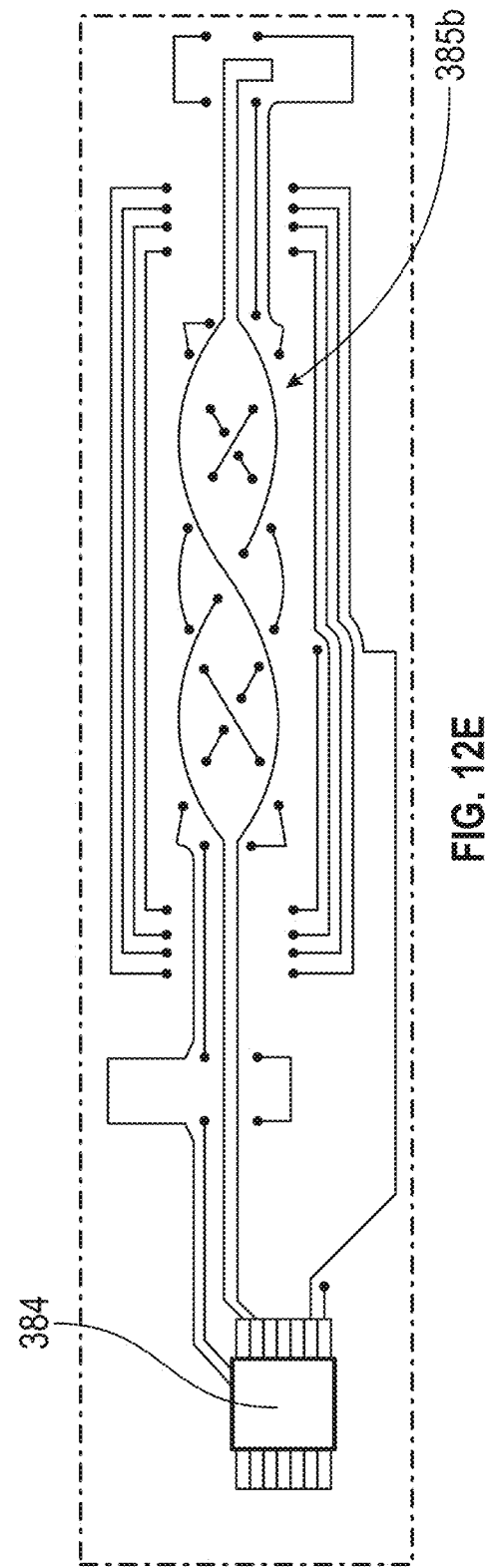
FIG. 12E illustrates a standard PCB coil layout for a linear coil inductive detector according to some embodiments.

FIG. 12B illustrates a perspective view of a handpiece including a linear coil inductive detector 383 for sensing the movement of a metallic target 387 disposed in the paddle 329 according to some embodiments. FIG. 12C illustrates a plan view of the handpiece including the linear coil inductive detector 383 of FIG. 12B. FIG. 12D illustrates a modified PCB coil layout 385a for the linear inductive detector 383 shown in FIGS. 12B and 12C according to some embodiments. FIG. 12E illustrates a standard PCB coil layout 385b for a linear coil inductive detector.

Referring to FIG. 12B, the linear coil inductive detector 383 may include a linear coil sensor 384 and a PCB coil layout 385. Referring to FIGS. 12B and 12C, the inductive detector 383 is disposed inside the handpiece so that the PCB coil layout 385 faces the metallic target 387 disposed in the paddle 329. In some cases, the inductive detector 383 or at least the PCB coil layout 385 of the detector 383 may be disposed inside the paddle 329. In such cases, the metallic target may be disposed inside the handpiece body to face the PCB coil in the paddle 329. Furthermore, when the PCB coil layout 385 is disposed inside the paddle 329, the linear coil sensor 384 may be disposed inside the body.

When the paddle 329 moves between the closed position 329a and the open position 329b (see, for example, FIG. 11A), it does not directly approach nor directly move away from the PCB coil layout 385. Instead, the paddle 329 moves with respect to the PCB coil layout 385 at an angle. Thus, the plane of the PCB coil layout facing the metallic target 387 would not be parallel to the plane of the metallic target 387. Thus, unlike the metallic target 369 disposed in the wiper 370 that moves in parallel with respect to the PCB coil 382, the PCB coil layout 385 and the metallic target 387 are not coplanar except that in the closed position of the paddle 329, the target 387 and the coil layout 385 would be coplanar.

The operation of the linear coil inductive detector 383 is described with respect to FIG. 12C. In FIG. 12C, the paddle and wiper in the dotted lines represent that the paddle 329 and the wiper 370 are in a closed position. The metallic target 387 forms a pincer angle (θ) in an open position. As the paddle 329 laterally moves from the open position (θ) to the closed position (generally 0°), the metallic target 387 (for example, a middle portion thereof) moves with respect to the PCB coil layout 385 from a position A to a position B on the PCB coil layout 385. Furthermore, as the paddle 329 laterally moves from the closed position to the open position (θ), the metallic target 387 moves with respect to the PCB coil layout 385 from the position B to the position A on the PCB coil layout 385. In some cases, the inductive sensor 384 may process secondary voltages received at the receiver coils on the PCB coil layout 385, and obtain a signal representing the position of the metallic target 387. In some cases, the inductive sensor 384 can be implemented with, for example, ICs available from IDT.

In some cases, the PCB coil layout may have a modified linear coil layout 385a shown in FIG. 12D. The non-coplanar nature of the metallic target 387 with respect to the PCB coil layout 385 may become more substantial as the pincer angle becomes greater, and may become less substantial or insignificant as the pincer angle approaches zero. The modified PCB coil layout 385a may adjust the change in output of the sensor 384 due at least to the change in proximity to the metallic target 387 so that the output may become substantially the same as the standard linear layout 385b shown in FIG. 12E. In some cases, an additional adjustment may be made by a further modification to the modified PCB coil layout 385a and/or by a processor in order to further compensate the non-coplanar nature of the movement of the metallic target 387. This additional adjustment by the processor may be made to the modified coil layout 385a or the standard coil layout 385b.

In some cases, the metallic target 387 may also have a modified shape in order to at least partially compensate the non-coplanar nature of the movement of the metallic target 387 with respect to the PCB coil layout 385. For example, the metallic target 387 may have a generally trapezoidal shape (not shown) that is generally inverse with respect to the modified PCB coil layout 385a shown in FIG. 12D. For example, the trapezoidal shape of the metallic target 387 may have the height of the left side smaller than the height of the right side, unlike the trapezoidal shape of the modified PCB coil layout 385a where the height of the right side is smaller than the height of the left side. In some cases, paddle 329 may be modified such that a curvature of paddle or at least the inside face of paddle (the side of the paddle facing the body of the handpiece) may be slightly curved as opposed to being linear (as shown in the drawings, see for example FIG. 4A). The metallic target 387 would also follow this curvature. In some cases, only the metallic target 387 would be modified to be curved. This curvature of the paddle, paddle face and/or the metallic target 387 would provide a different amount of area of the metallic target that would be substantially coplanar with the PCB coil layout 385 as the pincher is depressed (moved laterally). The curvature could compensate the non-coplanar nature of the movement of the metallic target 392 with respect to the PCB coil layout 385. The described modifications are merely examples, and other modifications to the PCB coil layout 385, the metallic target 387, positioning of the PCB coil layout, curvature of the PCB coil layout and/or the modification by a processor may also be made so that the metallic target may follow a substantially coplanar moving path with respect to a sensor coil or at least the output from the inductive sensor follows a more standardized output.

b. Spiral Coil Inductive Detector

Figure 13A:
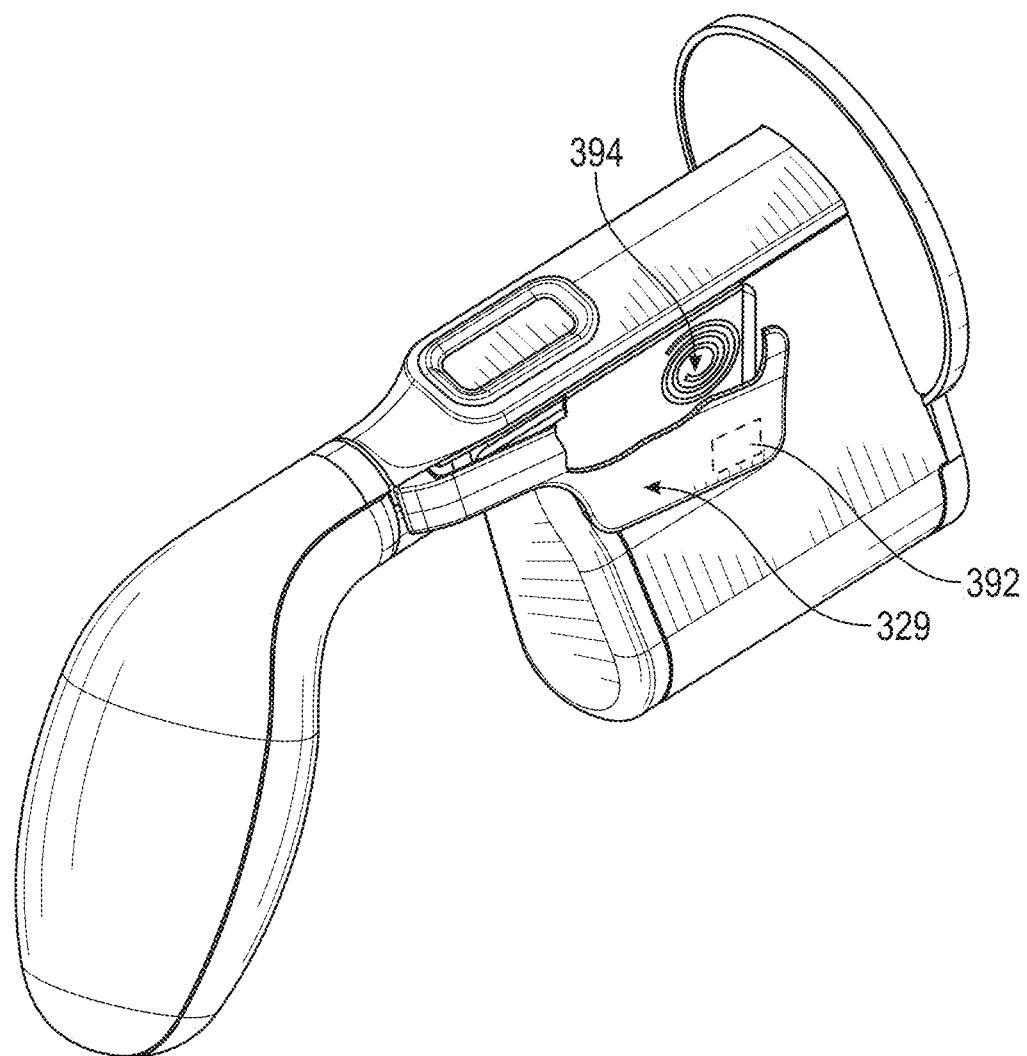
FIG. 13A illustrates a perspective view of a hand controller including a spiral coil inductive detector for sensing the movement of a metallic portion in the paddle according to some embodiments.
Figure 13B:
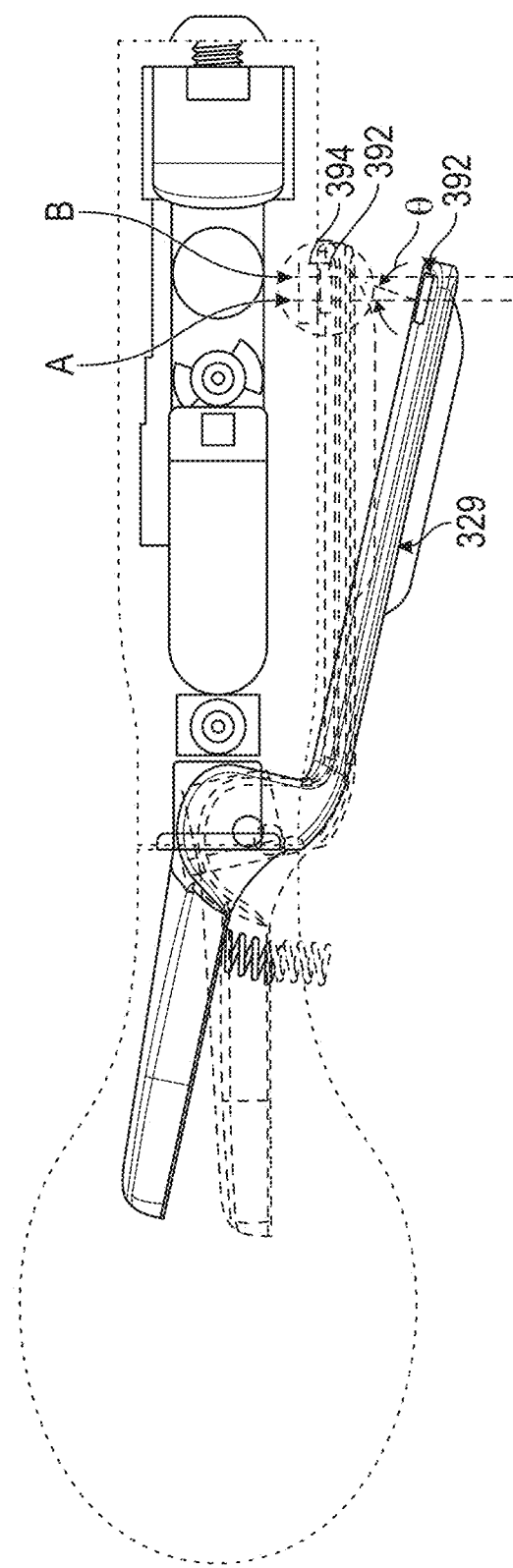
FIG. 13B illustrates a plan view of the hand controller including the spiral coil inductive detector of FIG. 13A according to some embodiments.
Figure 13C:
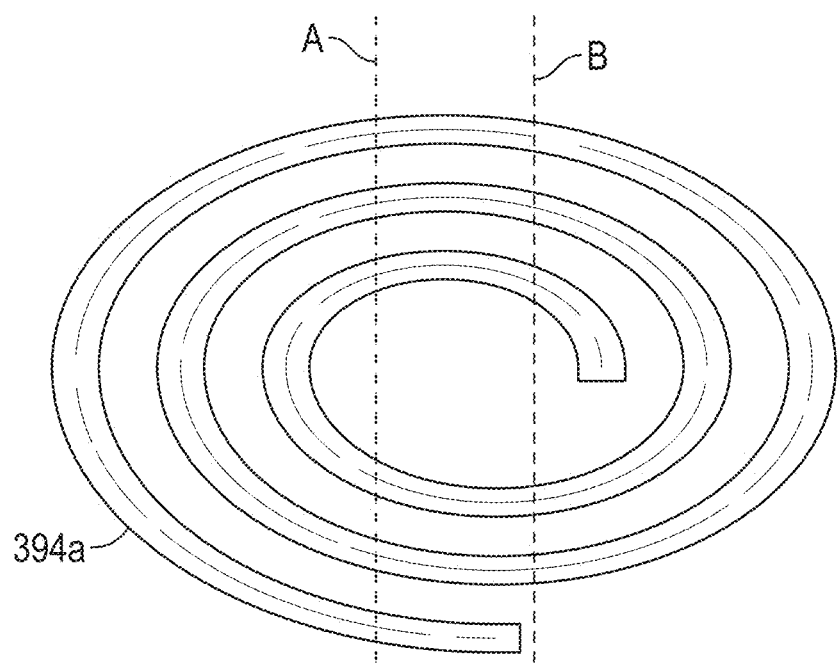
FIG. 13C illustrates a modified coil layout for the spiral inductive detector shown in FIGS. 13A and 13B according to some embodiments.
Figure 13D:
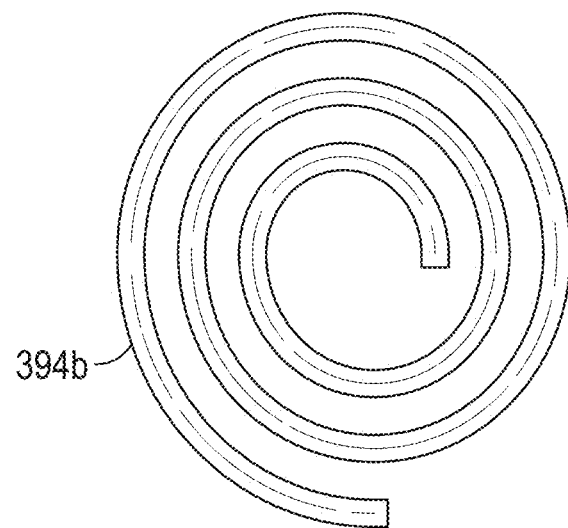
FIG. 13D illustrates a standard coil layout for a spiral coil inductive detector according to some embodiments.

FIG. 13A illustrates a perspective view of a handpiece including a spiral coil inductive detector 394 (sensor circuitry not shown; hereinafter to be interchangeably used with "spiral coil layout") for sensing the movement of a metallic portion or target 392 disposed in the paddle 329 according to some embodiments. FIG. 13B illustrates a plan view of the handpiece including the spiral coil inductive detector 394 of FIG. 13A. FIG. 13C illustrates a modified coil layout 394a for the spiral inductive detector 394 shown in FIGS. 13A and 13B according to some embodiments. FIG. 13D illustrates a standard coil layout 394b for a spiral coil inductive detector.

Referring to FIGS. 13A and 13B, the inductive detector 394 is disposed inside the handpiece body so as to face the metallic target 392 disposed in the paddle 329. In some cases, the spiral coil layout 394 may be disposed inside the paddle 329. In such cases, the metallic target may be disposed inside the handpiece body to face the coil layout in the paddle 329.

The operation of the linear coil inductive detector 383 is described with respect to FIG. 13B. Referring to FIG. 13B, as the paddle 329 laterally moves from the open position (θ) to the closed position (the paddle in the dotted lines shows that the paddle is positioned in the pincer angle being generally 0°), the metallic target 392 (for example, a middle portion thereof) moves with respect to the coil layout 394 from a position A to a position B on the coil layout 394. Furthermore, as the paddle 329 laterally moves from the closed position to the open position (θ), the metallic target 392 moves with respect to the coil layout 394 from the position B to the position A on the coil layout 394. The inductive sensor circuitry may process secondary voltages received at the receiver coils on the spiral coil layout 394, and obtain a signal representing the position of the metallic target 392.

As described herein with respect to FIGS. 12B-12E, the non-coplanar nature of the metallic target 392 with respect to the coil layout 394 may become more substantial as the pincer angle becomes greater, and may become less substantial or insignificant as the angle approaches zero. In some cases, the spiral coil layout may have a modified coil layout 394a shown in FIG. 13C. The modified coil layout 394a may have an elliptical shape. The modified coil layout 394a may adjust the change in output of the sensor due at least to the change in proximity to the metallic target 392 so that the output may become substantially the same as the standard linear layout 394b shown in FIG. 13D. In other cases, at least some portion on the right half of the spiral coil (for example, the right end portion of the coil) may be bent toward or away from the paddle 329 in order to additionally compensate the non-coplanar nature of the movement of the metallic target 392 with respect to the PCB coil layout 394. In some cases, the paddle 329 and/or the metallic target 392 may be curved similarly as described above with respect to the "Linear Coil Inductive Detector".

In some cases, an additional adjustment may be made by a further modification to the modified PCB coil layout 385a and/or by a processor in order to further compensate the non-coplanar nature of the movement of the metallic target 392. This additional adjustment by the processor may be made to the modified coil layout 394a or the standard coil layout 394b. In some cases, the spiral coil inductive sensor can be implemented with, for example, ICs available from Texas Instruments Inc. (TI).

In some cases, the metallic target 392 may also have a modified shape in order to at least partially compensate the non-coplanar nature of the movement of the metallic target 392 with respect to the PCB coil layout 394. For example, the metallic target 392 may have a generally elliptical shape (as opposed to a circular shape) similar to the spiral coil 394a. Furthermore, at least a portion of the metallic target 392 (for example, a right half) may be bent toward the coil 394 to compensate the non-coplanar nature of the movement of the metallic target 392 with respect to the PCB coil layout 394. The described modifications are merely examples, and other modifications to the PCB coil layout 394 and/or the metallic target 392 (including modification by a processor) may also be made so that the metallic target may follow a substantially coplanar moving path with respect to a sensor coil.

In some cases, the coil layout may instead be included on or inside the paddle 329 (not shown). In place of PCB traces to produce the coils used for inductive sensing, metal shapes on the inside walls of the paddle 329 or inside the paddle may be used. Laser direct structuring (LDS) may be utilized to produce the metals shapes as LDS is appropriate for extremely small and space constrained applications. The LDS metal may directly replace the PCB coil, but all of the described restrictions may apply (coplanar vs proximity, minimum inductance, etc.).

3. Proximity Sensor

The pincer angle can also be detected by a proximity sensor. The proximity sensor can measure the distance between a sensor coil and a metallic target, as opposed to measuring a coplanar (or substantially coplanar) travel of the metallic target. For example, the proximity sensor can directly detect the position of the paddle 329 with respect to the surface of the handpiece body facing the paddle 329. This method is inherently resilient to outside electro-magnetic interference and simplifies the mechanical design, by not requiring an external effector (magnet) and by detecting the paddle's movement directly. In some cases, the proximity sensor can be implemented with, for example, ICs available from Texas Instrument (TI).

Figure 14:
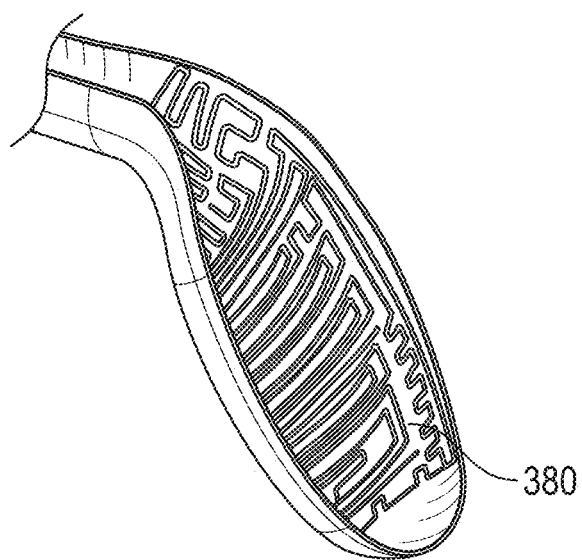
FIG. 14 illustrates a perspective view of a metal shaped PCB coil formed inside the wall of a handpiece according to some embodiments.

In some cases, the proximity sensor may be disposed inside the handpiece body to face the paddle 329. In some cases, as shown in FIG. 14, the proximity sensor can be formed by layering coils across multiple PCB layers. This design may be advantageous, since the sensor geometry is generally more flexible, and thus is useful when there is not much space like in a handpiece. Accordingly, the greater distance of the paddle makes the TI chip a better candidate. In some cases, the proximity sensor may be disposed inside the paddle 329 to face a side surface of the handpiece body.

In some cases, the proximity sensor can be implemented with, ICs available from IDT. In such cases, the IDT ICs may be positioned inside the handpiece body, and a metallic target would be in or on the paddle 329. As the paddle 329 is compressed, the metallic target would move toward the IDT ICs and the detected signal may generally become stronger as the paddle 329 approaches the handpiece body. This is a variation of the traditional use of the IDT ICs that usually just detect a linear travel (not proximity). It could detect proximity as the detected signal would change (become stronger) but the detected signal would not follow a linear path but rather a non-linear or log path. However, with the variables known, the signal could be determined. The TI sensor may be a better proximity sensor than the IDT sensor, as the TI chip may be configured to increase the effective coil length (for example, adding more PCB layers). Both of the TI and IDT sensors may require some minimum inductance. The inductance is generally proportional to the amount of a PCB coil on the sensor that is laid out.

In some cases, the coils used for inductive sensing can be implemented as PCB traces. In some cases, as shown in FIG. 14, the coils can be implemented as metal shapes 380 on the inside walls of the handpiece itself. This technique is referred to as laser direct structuring (LDS), and may be utilized for an extremely small and space constrained RF antenna. The choice of a TI or IDT sensor may depend on whether the tail or the paddle is used as a target. The TI product may need less internal processing. These more 'raw' values would make this implementation easier to iron out. The LDS metal may directly replace the PCB coil, but all of the described restrictions may apply (coplanar vs proximity, minimum inductance, etc.).

4. Compressing Spring

Figure 33:
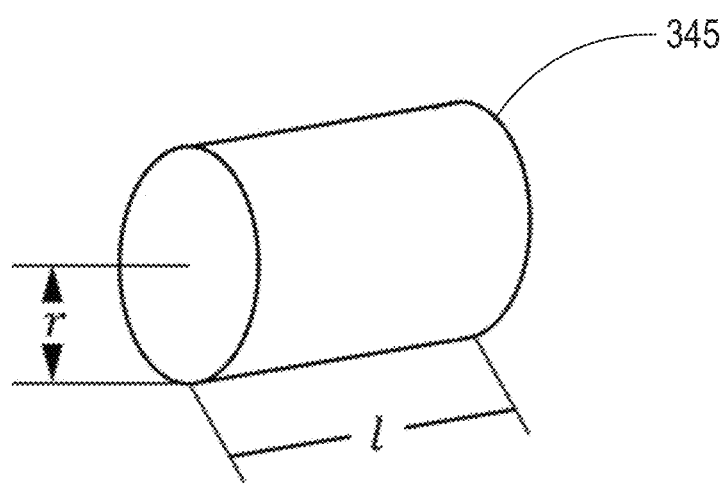
FIG. 33 illustrates a perspective view of an example coil to be used as a compression spring for pincer angle detection according to some embodiments.

The pincer angle may be obtained by directly detecting the compression of the spring 348 that provides resistance to the paddle 329 (see, for example, FIG. 11B). In this case, an inductor may be a charged coil of wire, and a spring may be a stiff coil of wire. If the spring were charged with an alternating current, it would behave like an inductor. Compression of the spring would lead to a linear change in inductance. Post processing may be used to linearize the output of an inductance sensor. In some case, the spring can have an explicit inductor to meet the minimum inductance. The spring method can be advantageous, as it is inherently linear. Referring to FIG. 33, the inductance of a coil (or spring) 345 is given by the equation below. When the spring 345 is compressed, its length changes (small l) so that it has a linear effect on the inductance. This can be described by the equation below.

$$\mathcal{L} = \frac{N^2 \mu A}{l}$$

$$\mu = \mu_r \mu_o$$

Where, $\mathcal{L}$=Inductance of coil in Henrys
N=Number of turns in wire coil (straight wire=1)
μ=Permeability of core material (absolute, not relative)
$\mu_r$=Relative permeability, dimensionless ($\mu_o$=1 for air)
$\mu_o$=1.26×10$^{-6}$T·m/At (permeability of free space)
A=Area of coil in square meters=$\pi r^2$
l=Average length of coil in meters Presence Detection As described herein, a handpiece controls the movement of a surgical instrument. Thus, it is desirable for a safety purpose to activate the handpiece when it is safe, for example, when it is grasped by or adjacent to an operator's hand. The presence detector can detect whether a user's hand is present on or within a certain distance of the handpiece. In some cases, such distance may be a few millimeters, a few centimeters, or a few inches. In some cases, the presence detector may detect an operator's hand contacting the handpiece.

In some cases, the presence detector can be a capacitive proximity sensor and can be disposed on a PCB on the center mount 342 (see, for example, FIG. 10). The presence detector can be implemented with two redundant sensors for additional safety purposes. The redundant sensors may charge the lower and upper housings 324 and 322 (formed of metal) and use them as their antenna or sense-element. In some cases, the presence detector can be a metallic coating or a metal shell underneath the hard plastic shell of the handpiece to effectively create a large capacitive proximity sensor. The presence detector can be implemented with, for example, ICs available from Microchip Technology Inc.

In some cases, instead of using a metal shell or coating, a wire, as shown in FIG. 14, may be formed throughout the length of the inside of the handpiece to effectively create an antenna. In such cases, coverage may be less uniform than on a primary path, but there may be potential manufacturing advantages. The presence detector may also detect a gloved hand and a double-gloved hand. The presence detector can calibrate the sensor to detect proximity even when a user is lightly touching the handpiece or not touching it all, for example, a few millimeters away. The presence detector may also be able to detect and differentiate between various materials, for example, whether a hand is within a desired proximity (directly coupled or within a tolerated distance), a gloved hand is within the desired proximity or whether a different unwanted object is within the desired proximity. This may be important to avoid unintended contact of the handpiece and to only allow presence to be detected when a hand (or gloved hand) of the operator is within the desired proximity. The advantage of this mode is that the handpiece does not clutch out or disengage from controlling the surgical system when a user moves the fingers or hand on the handgrip.

Input Control Interfaces

User or operator inputs may be provided to the robotic surgery system 100 in a number of different ways. For example, movement of the handpieces 122 and 124 can be used to provide a user input for controlling a tool such as a surgical instrument or a camera. As another example, the foot pedal 126 disposed at a lower portion of the workstation 102 may provide a user input used to perform a certain function such as instrument clutching.

Another user input (hereinafter to be interchangeably used with "additional user input" or "second user input") may be provided via the input control interface 326a disposed on an upper surface of the handpiece body. The input control interface 326a (see, for example, FIG. 3B) may be configured to control a number of functions for the robotic surgery system 100. The input control interface 326a may receive an input used to control a surgical instrument. The input control interface 326a may also receive another input used to zoom in or zoom out a camera. The input control interface 326a may further receive another input used to turn on and off an illuminator. The input control interface 326a may also be used to provide a user input that can be provided by other input mechanism such as the foot pedal 126. In this case, since the input control interface 326a is positioned in the handpiece grasped by an operator during operation, a user input may be more conveniently and/or more accurately provided than the foot pedal 126. The input control interface may be implemented by a mechanical switch, a button, a lever, a wheel, a trackpad or a capacitive touch surface. For the purpose of convenience, shared input control, gesture control and handpiece feedback control below will be described using a trackpad or a touch capacitive surface.

1. Trackpad

In some cases, the second PCB 326 (see, for example, FIG. 10) can include a trackpad 326a as an input control interface. The trackpad 326a may be disposed on the upper surface of the handpiece 122. The trackpad 326a can be used to receive an additional user input such as camera control or instrument clutch where instrument control is disengaged. The trackpad 326a can also be used for direct gesture recognition with a variety of gestures (hereinafter to be interchangeably used with "tool functions"). For example, the trackpad 326a can detect swipe of an operator's finger thereon in either direction, swipe and hold in either direction, tap, tap and hold, multiple taps, or multiple taps and hold. In some cases, the trackpad 326a may be sized to receive an input by a fingertip of an average operator's finger (for example, index finger or thumb).

Figure 15:
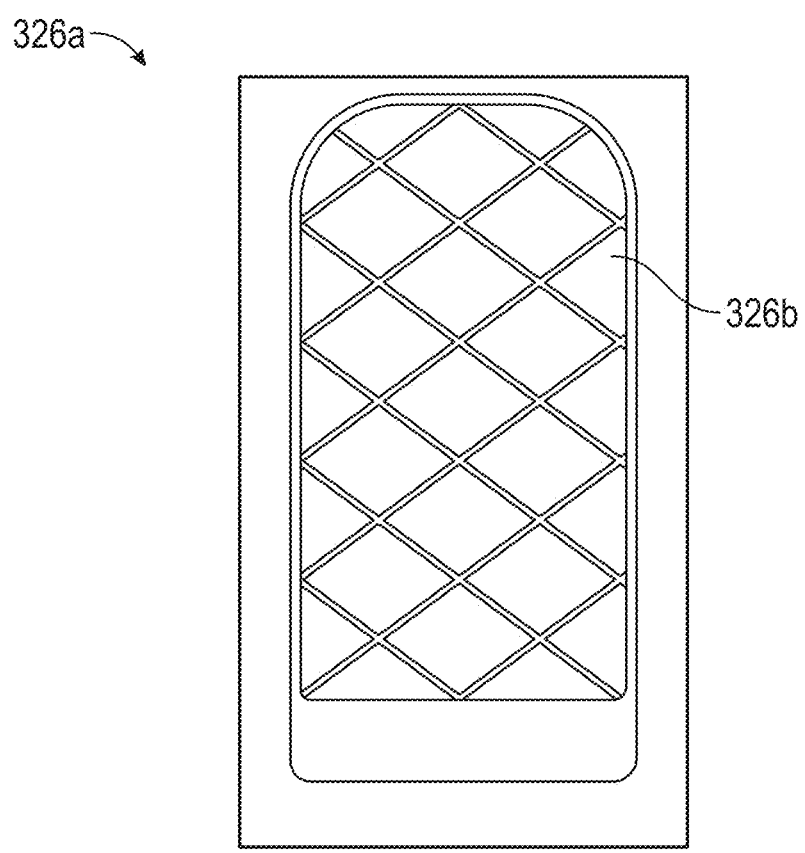
FIG. 15 illustrates a plan view of an example trackpad of a hand controller according to some embodiments.

The trackpad 326a (including a trackpad driver) can be implemented with, for example, ICs available from Azoteq of South Africa. The Azoteq ICs may be configured to provide data over Inter-Integrated Circuit (I2C), which can allow the workstation to interpret the gestures. In some cases, as shown in FIG. 15, the trackpad 326a can use PCB traces placed in a grid pattern 326b as sensing elements.

2. Capacitive Touch Surface

Figure 16A:
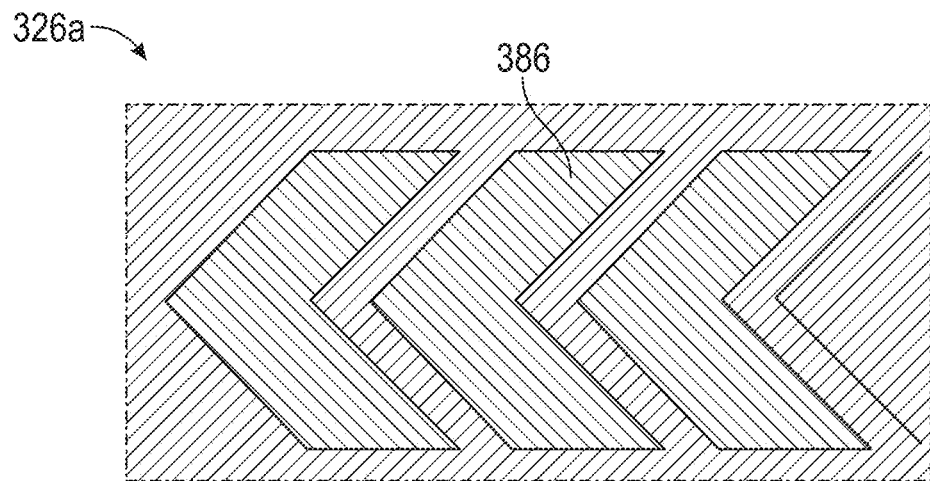
FIG. 16A illustrates a plan view of a capacitive touch surface having multiple 'V' shaped capacitive buttons according to some embodiments.
Figure 16B:
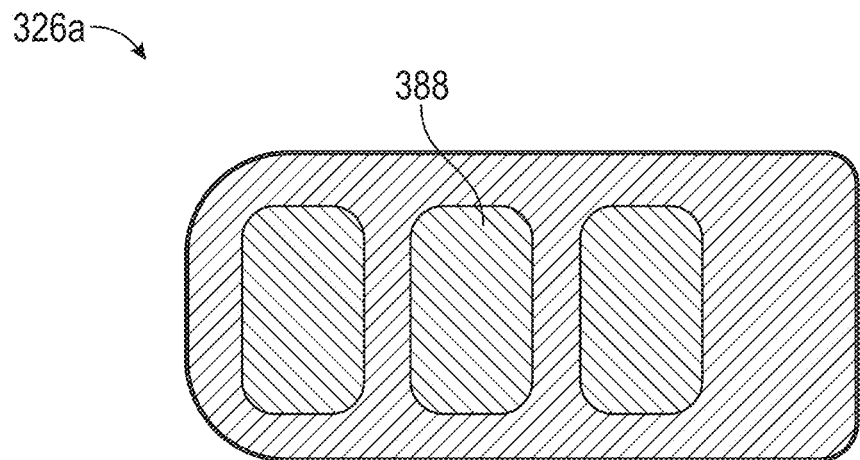
FIG. 16B illustrates a plan view of a capacitive touch surface having multiple rectangular capacitive buttons according to some embodiments.
Figure 17A:
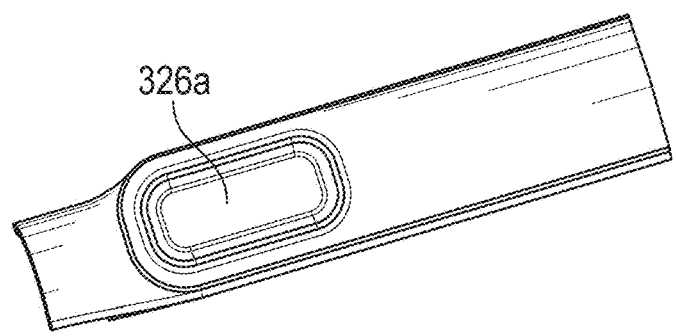
FIG. 17A illustrates a closed-up view of the trackpad according to some embodiments.

In some cases, the second PCB 326 can include a capacitive touch surface 326a instead of or in addition to the trackpad (for example, one trackpad and one capacitive touch surface in different locations). FIG. 17A shows an example capacitive touch surface. Referring to FIG. 17A, the capacitive touch surface 326a may be smooth and glossy. The capacitive touch surface 326a may be made by, for example, pad printing. The capacitive touch surface 326a can be a capacitive touch IC to directly create a capacitive slide element. In some cases, as shown in FIGS. 16A and 16B, three or four capacitive touch elements 386 and 388 (for example, as individual capacitive buttons) can be provided. Although FIGS. 16A and 16B show chevron (or 'V' shapes) and rectangular shapes, the capacitive touch elements 386 and 388 may have other shapes such as line, square, circle, oval or other polygonal shapes. Furthermore, the number of capacitive touch elements may be less than three or more than four depending on the requirement of the touch input surface 326a. In some cases, the capacitive touch surface 326a may be sized to receive an input by a fingertip of an average operator's finger (for example, index finger or thumb).

The capacitive touch surface (including a capacitive touch surface driver) can be implemented with, for example, ICs available from Microchip. In this Microchip device, multiple capacitive touch elements can be read by a series of digital logic implemented as a complex programmable logic device (CPLD) (conceptually similar to a field-programmable gate array (FPGA)) that is programmed only once to recognize the desired gestures. The Microchip device can be configured to provide data over I2C, which can allow the workstation to interpret the gestures.

Figure 17B:
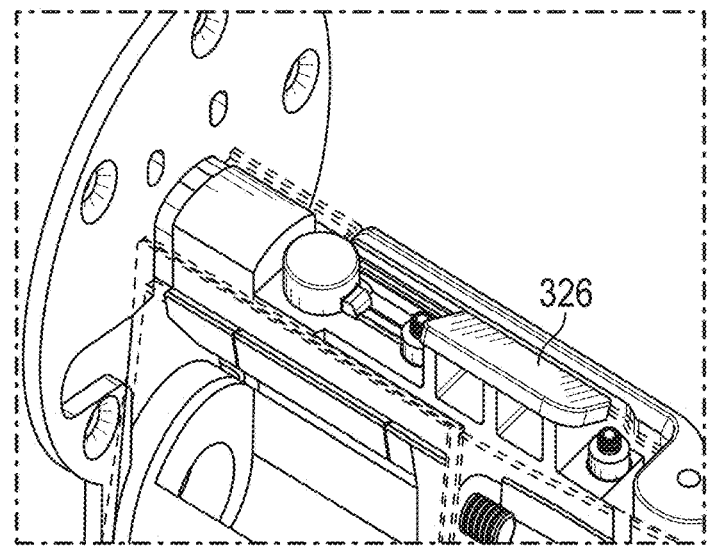
FIG. 17B illustrates an example location of a capacitive gesture recognition circuitry according to some embodiments.
Figure 17C:
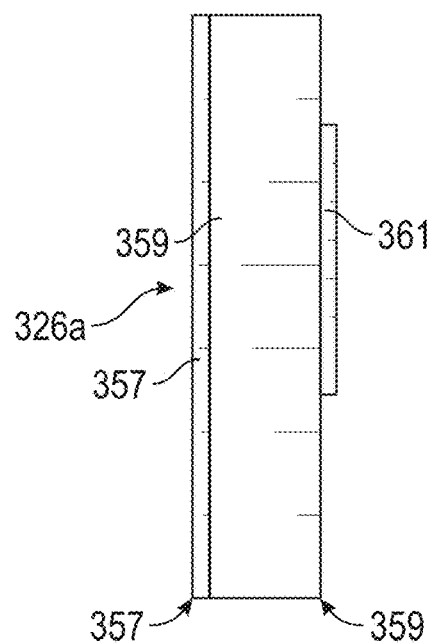
FIG. 17C illustrates a cross-sectional view of a capacitive gesture recognition PCB according to some embodiments.

In some cases, as shown in FIGS. 17B and 17C, the capacitive touch driver circuitry can be placed directly underneath the gesture area. FIG. 17C shows a cross-sectional view of the second PCB 326 that includes a capacitive touch surface 326a and its drive circuitry. The second PCB 326 may include a capacitive touch IC 359 and an adhesive 357 on which the capacitive touch surface 326a is attached. Other circuit components 361 may also be disposed below the capacitive touch IC 359.

In some cases, the second PCB 326 can include a capacitive button (not shown) that can toggle between two states, for example, between instrument and camera modes. The capacitive button can use in single or double-click (or multiple-click) mode. For the input button/switch, a capacitive slider may be used for clutch control from a handpiece, although a single cap button could be acceptable with pressure sensitive input (flex). The capacitive slider may be controlled by a microprocessor. The use of a microprocessor may be beneficial as being inherently more tunable or customizable. The same microprocessor can be used to control presence detection. The microprocessor may also be able to drive the haptic engines.

3. Force Sensitive Resistor

The touch input interface 326a may be implemented by a force sensitive resistor. The force sensitive resistor may be incorporated underneath the touch area, and can be made more robust and user friendly. If a click gesture is required, a capacitive element in addition to the pressing element can be triggered. This button can make a capacitive touch button feel like a real button.

Shared Input Control

In some cases, in order to minimize the number of input controls required to cause movement of various aspects of a robotic surgical system, certain input controls may be shared. This may reduce overall system clutter, such as inadvertent control and/or cognitive overload.

In some cases, the same trackpad 326a can be used to perform functions of two or more input controls. When an input control is used to control a first feature/function (for example, instrument clutch), a second feature/function (for example, camera control) may be disabled. In some cases, the second feature/function and first feature/function may be operated mutually exclusively and separately at all times. That is, the same input control interface can be used to control two or more different devices such as a camera and a clutch at different times.

Figure 18:
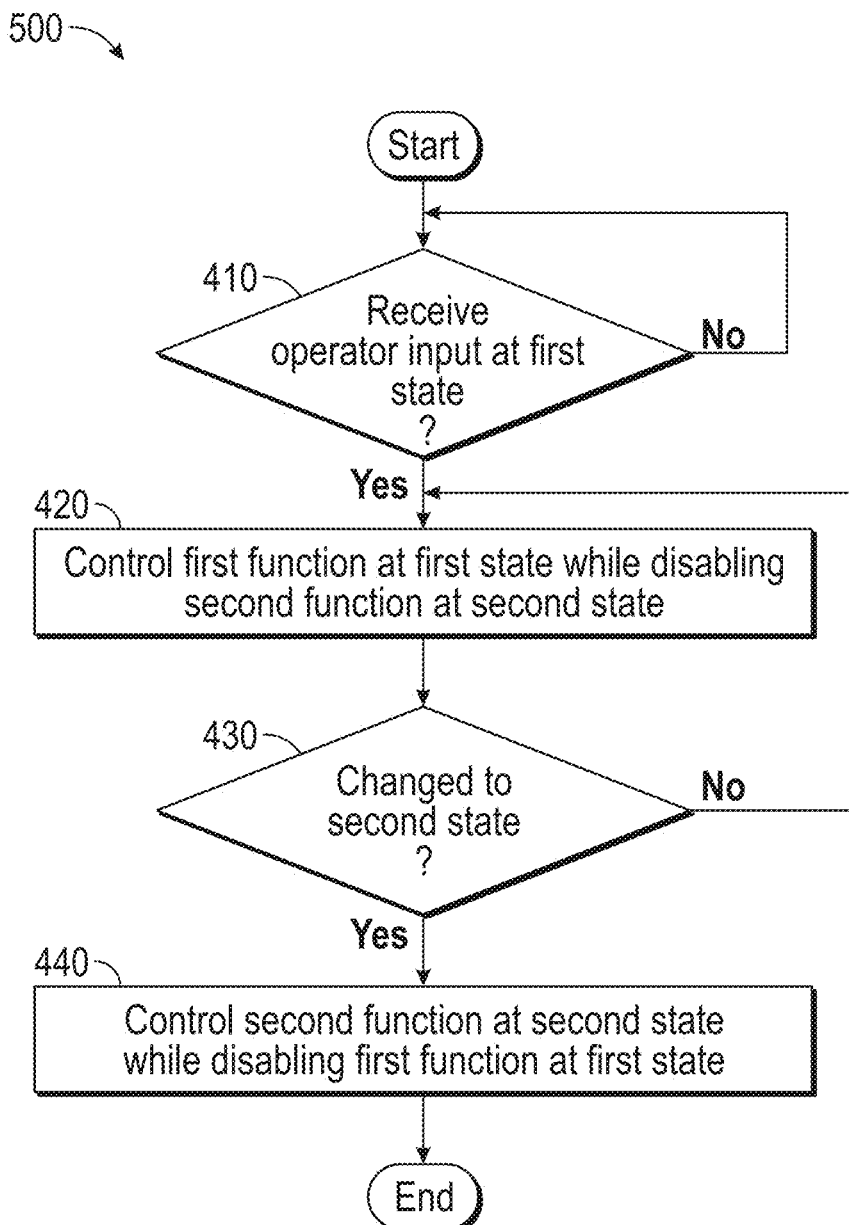
FIG. 18 illustrates a flowchart for a shared input control process according to some embodiments.

FIG. 18 illustrates a flowchart for a shared input control process 500 according to some embodiments. Referring to FIG. 18, the shared input control process 500 for a handpiece will be described.

Although the process 500 is described herein with reference to a particular order, in various implementations, states herein may be performed in a different order, or omitted, and additional states may be added. The process 500 may be performed by a processor (not shown). This also applies to the processes 600-900 shown in FIGS. 19, 21, 22 and 26.

In state 410, it is determined whether an operator input has been received at a first state or mode. The operator input can be received through the input control interface 326a (see, for example, FIG. 3B). The first state or mode may be a first device operation state or mode, for example, a camera control operation mode or an instrument clutch mode.

The input control interface 326a may be a trackpad or a capacitive touch surface as described herein. The trackpad may recognize at least one of the following types of operator inputs: swipe from a first side of the trackpad to a second side of the trackpad different from the first side, tap, swipe and hold, tap and hold, multiple taps, or multiple taps and hold, or a combination thereof. The processor may perform different functions based on the swipe, the swipe and hold, the tap, the tap and hold, the multiple taps, and the multiple taps and hold. The capacitive touch surface may include at least one capacitive button that can sense a single-click or a double-click (or multiple-click), and the processor may perform different functions based on the single-click or multiple-click. The description of this paragraph applies to a camera control process 600 shown in FIG. 20 and an instrument clutch process 700 shown in FIG. 22.

If it is determined in state 410 that the operator input has not been received at the first state, the state 410 may repeat. If it is determined in state 410 that an operator input has been received at the first state or mode, the processor may control a first function at the first state while the second function is disabled at a second state (state 420). For example, the processor may control enabling and disabling a camera control function in a camera control mode while an instrument control by the handpieces 122/124 is disabled so that the surgical instrument(s) would not move even if the handpieces 122/124 are moved.

In state 430, it is determined whether the first state has been changed to the second state or another different state. The first state can be changed to the second state or another different state by actuating the input control interface 326. For example, a camera control operation mode can be changed to an instrument clutch operation mode. If it is determined in state 430 that the first state has not been changed to the second state, the states 420 and 430 may repeat.

If it is determined in state 430 that the first state has been changed to the second state, the processor may control the second function at the second state while the first function is disabled. For example, the processor may control enabling and disabling an instrument clutch control function in the instrument clutch mode while the camera operation is disabled (state 440) so that the camera would not move even if the handpieces 122/124 are moved.

1. Camera Control

Figure 19A:
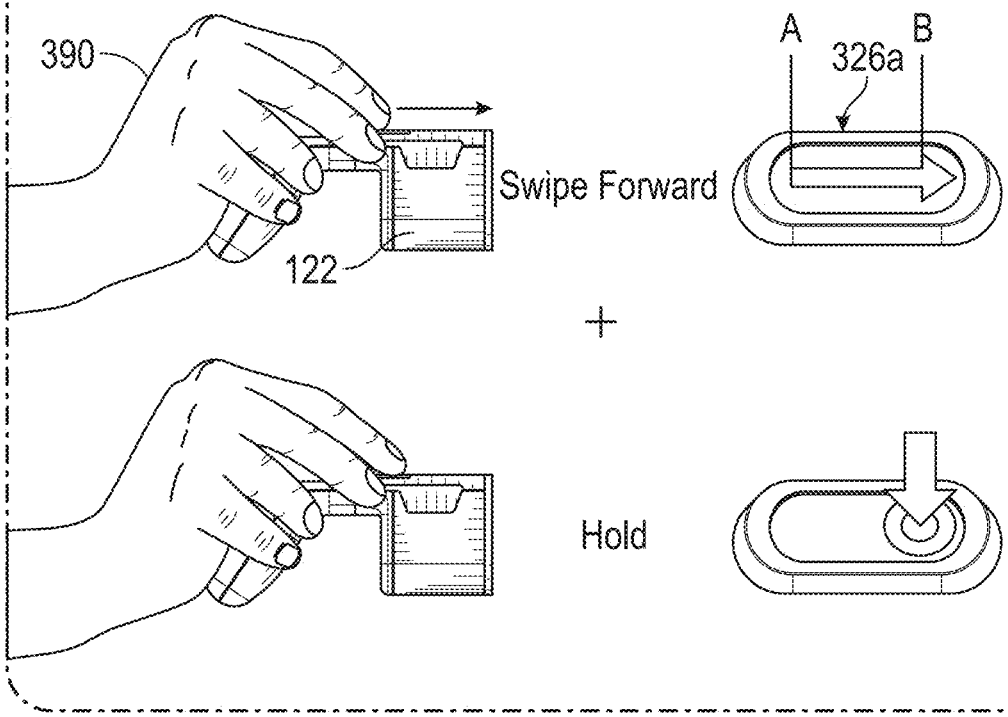
FIGS. 19A and 19B illustrate conceptual diagrams showing a camera control operation according to some embodiments.
Figure 19B:
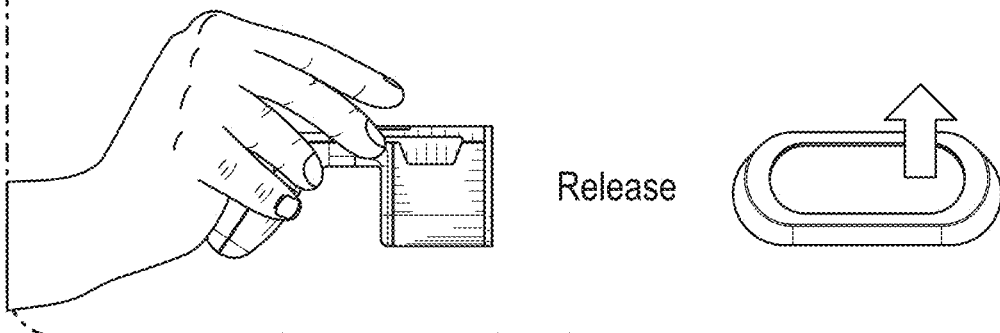
Figure 20:
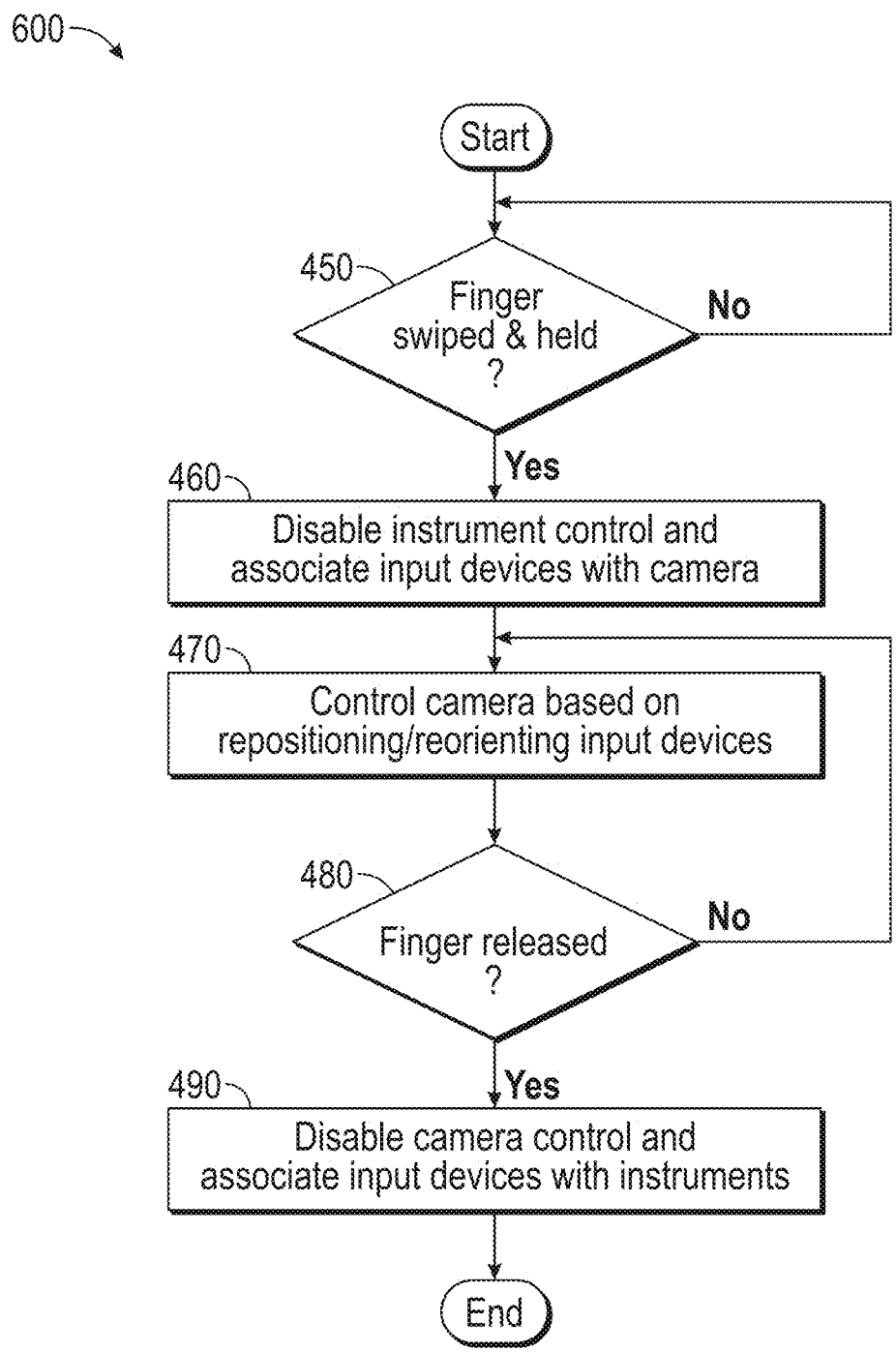
FIG. 20 illustrates a flowchart for a camera control process shown in FIGS. 19A and 19B according to some embodiments.

FIGS. 19A and 19B illustrate conceptual diagrams showing a camera control operation according to some embodiments. FIG. 20 illustrates a flowchart for a camera control process 600 shown in FIGS. 19A and 19B according to some embodiments.

Referring to FIG. 20, it is determined whether an operator's finger has been swiped forward and held on the input control interface 326*a* of the handpiece 122 (state 450). In some cases, as shown in FIG. 19A, swiping of the operator's finger 390 from a point A to a point B on the input control interface 326*a* can be determined by: i) detecting a contact of the operator's finger 390 on the point A; ii) detecting that the finger 390 has remained in contact with the input control interface 326*a* and moved to the point B; and iii) detecting that the finger 390 remains at the point B. If it is determined in state 450 that the operator's finger has not been swiped and held, the state 450 may repeat.

If it is determined in state 450 that the operator's finger 390 has been swiped forward and held on the input control interface 326*a*, an association of the input devices 132/112 with the surgical instruments becomes disabled, the instruments become disabled, and at least one of the input devices 132/112 becomes associated with a camera (state 460). That is, the camera control operation is turned on as shown in FIG. 19A.

In state 470, the camera is controlled by repositioning and/or reorienting at least one of the input devices 132/112. Since the instruments have been disassociated from the input devices 132/112, repositioning and/or reorienting the input devices 132/112 would have no impact on the surgical instruments (disabled). In some cases, there may be only one camera at the surgery site, and only one of the input devices 132/112 may control the camera. In these cases, movement of the other input device may have no impact on the camera. In some cases, both of the input devices 132/112 may be used to move the camera by either locking the relative movement of each of the input device 132/112 to each other or averaging the movement of the input devices.

In state 480, it is determined whether the operator's finger has been released from the point B of the input control interface 326*a*, as shown in FIG. 19B. If it is determined in state 480 that the operator's finger has not been released, the states 470 and 480 may repeat.

If it is determined in state 480 that the operator's finger 390 has been released from the point B, an association of the input devices 132/112 with the camera becomes disabled, the camera becomes disabled, and at least one of the input devices 132/112 becomes associated with the surgical instruments (state 490). That is, the camera control operation is turned off as shown in FIG. 19B. In some cases, control of the instruments may occur automatically upon the camera turning-off or upon another subsequent intervening event such as tapping the foot pedal 126.

The described operator inputs (swiping forward and held/release) and corresponding controls (turning on and off the camera control) are merely examples, and many other combinations of input types by the input control interface and corresponding controls are possible. For example, operator inputs such as tap, tap and hold, multiple taps, multiple taps and hold, swiping backward, swiping backward and hold, multiple swiping (forward or backward), multiple swiping (forward or backward) and hold, or combinations thereof can be used to turn on or turn off the camera control operation. Furthermore, operator inputs may be received via other input interfaces such as a mechanical switch or button, a lever, self-centering wheel, or other non-trackpad or non-touch capacitive surface, as long as the same input control interface can share input controls for multiple functions associated with one or more surgical devices. The description of this paragraphs applies to the instrument clutch operation procedure below.

2. Instrument Clutch

Figure 22:
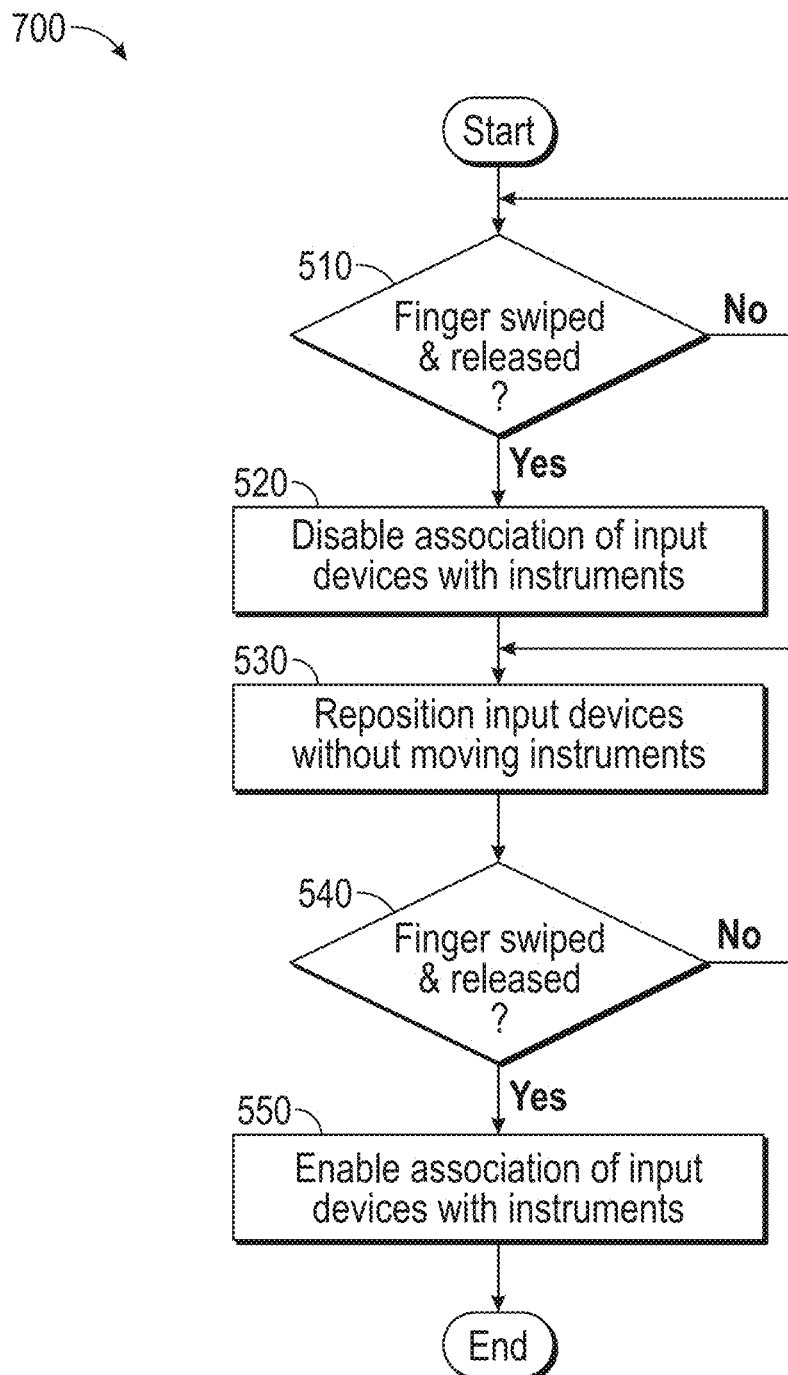
FIG. 22 illustrates a flowchart for an instrument clutch process shown in FIGS. 21A and 21B according to some embodiments.

FIGS. 21A and 21B illustrate conceptual diagrams showing an instrument clutch operation according to some embodiments. FIG. 22 illustrates a flowchart for an instrument clutch process 700 shown in FIGS. 21A and 21B according to some embodiments.

During operation of an input device, an operator frequently will reach the physical limits of repositioning the input device based on the mechanical limits of the device itself or the operator's arms. Thus, instrument clutching is advantageous when repositioning the input devices to enable a greater workspace. To allow the operator to "reset" or "re-center" their workspace, the operator would clutch to release association of the input device with a controlled slave instrument. Upon clutching, the input device may be repositioned while the instruments remain fixed. Upon unclutching, the association would be reestablished. Any errors introduced upon re-association such as orientation misalignment between the input device orientation and that of the instrument end-effector may be corrected by methods described in U.S. Patent Publication No. 2018/0271607 and U.S. Patent Publication No. 2018/0367777, which are assigned to the assignee of the present application and the disclosures of which are incorporated by reference in their entirety.

Referring to FIG. 22, it is determined whether an operator's finger 390 has been swiped backward on the input control interface 326*a* and released therefrom (state 510). In some cases, as shown in FIG. 21A, swiping of the operator's finger 390 from a point B to a point A on the input control interface 326*a* can be determined by: i) detecting a contact of the operator's finger 390 on the point B; ii) detecting that the finger 390 has remained in contact with the input control interface 326*a* and moved to the point A; and iii) detecting that the finger 390 has been released from the point A. If it is determined in state 510 that the operator's finger has been swiped backward and released, the state 510 may repeat.

If it is determined in state 510 that the operator's finger 390 has been swiped backward and released from the point A on the input control interface 326*a*, an association of the input devices 132/112 with the surgical instruments becomes disabled and the instruments become disabled (state 520).

In state 530, the input devices 132/112 are repositioned without moving the instruments. Since the surgical instruments have been disassociated from the input devices 132/

112 in state 520, the movement of the input devices 132/112 would have no impact on the instruments.

In state 540, it is determined whether an operator's finger 390 has been swiped backward again on the input control interface 326 of the handpiece 122 and released therefrom (state 510). This can be determined in the same way as described with respect to state 510. If it is determined in state 540 that the operator's finger has not been swiped backward and released, the states 530 and 540 may repeat.

If it is determined in state 540 that the operator's finger 390 has been swiped backward and released again from the point A on the input control interface 326, an association of the input devices 132/112 with the surgical instruments is re-enabled (state 550). See also FIG. 20B. Since the surgical instruments have been associated with the input devices 132/112, the movement of the input devices 132/112 will move the instruments.

In some cases, control of the instrument may occur automatically upon de-clutching or upon another subsequent intervening event such as tapping the foot pedal 126.

Gesture Controls (Tool Function Controls)

Gesture controls (hereinafter to be interchangeably used with "tool function controls") using a trackpad 326a (see, for example, FIG. 10) or another secondary control interface can be used to cause the system to function in various ways including causing the system to perform pre-set routines and functions. For example, swiping of the finger from one side to the other on the trackpad 326a may cause the surgical instrument to become locked in the state it is presently in (for example, one or more jaws of the instrument fixed in that position). This may be useful for situations where the user desires the surgical instrument to continue to grasp whatever it is grasping while the user repositions the input device. In other examples, certain gestures may cause the system to perform a pre-set routine such as certain surgery routines. Such gestures and resultant "auto" features may help reduce user fatigue.

Figure 23:
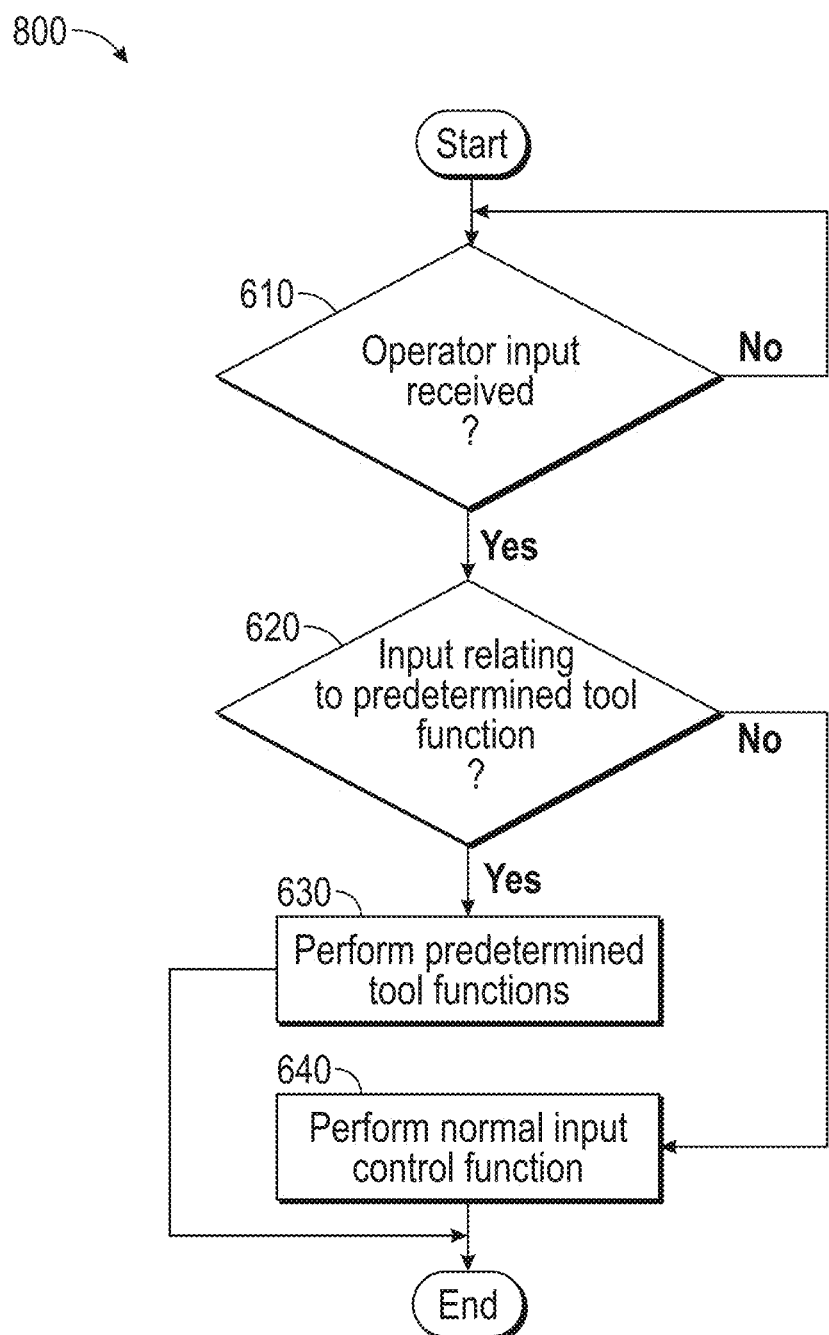
FIG. 23 illustrates a flowchart for a gesture control process according to some embodiments.

FIG. 23 illustrates a flowchart for the gesture control process 800 according to some embodiments. The gesture control process 800 may be performed by a processor (not shown). Referring to FIG. 23, the gesture control process 800 will be described.

In state 610, it is determined whether an operator input has been received. The operator input can be received via the input control interface 306a or 326a (see, for example, FIGS. 3A and 3B). If it is determined in state 610 that the operator input has not been received, the state 610 may repeat.

If it is determined in state 610 that an operator input has been received, it is determined whether the received operator input relates to one or more of a plurality of gestures or tool functions (state 620). The predetermined gestures or tool functions may include a predetermined surgery routine such as suturing (partial or complete suturing), cutting, grasping or moving in a predetermined direction. The suturing may include complete suturing and partial suturing. The predetermined surgery routine may also include moving the surgical tool in a predetermined direction. The predetermined direction may include a linear direction, a curved direction, a clockwise direction, a counterclockwise direction, semi-circular direction, or a circular direction. In some cases, the predetermined direction may be based on the pattern of the swipe/gesture itself (for example, a curved gesture may result in a movement in a curved direction). The tool functions may also include causing a lens of a camera to be washed, causing the camera to zoom in and out, causing the camera to pan, or causing the camera to tilt.

When the input control interface 326a is a trackpad, the trackpad may sense swiping of an operator's finger from a first point on the trackpad to a second point on the trackpad different from the first point, and the processor may control the surgical tool to remain adjacent to a current surgery position. For example, the processor may control the surgical tool to become locked in the current surgery position. The predetermined tool functions corresponding with the operator inputs may be stored in a memory being in data communication with the processor.

If it is determined in state 620 that the operator input relates to the predetermined tool functions, the processor may perform the predetermined tool functions (state 630). If it is determined in state 620 that the operator input does not relate to the predetermined tool functions, the processor may perform normal input control functions that are not associated with the predetermined tool functions (state 640).

Handpiece Feedback Control

Figure 25A:
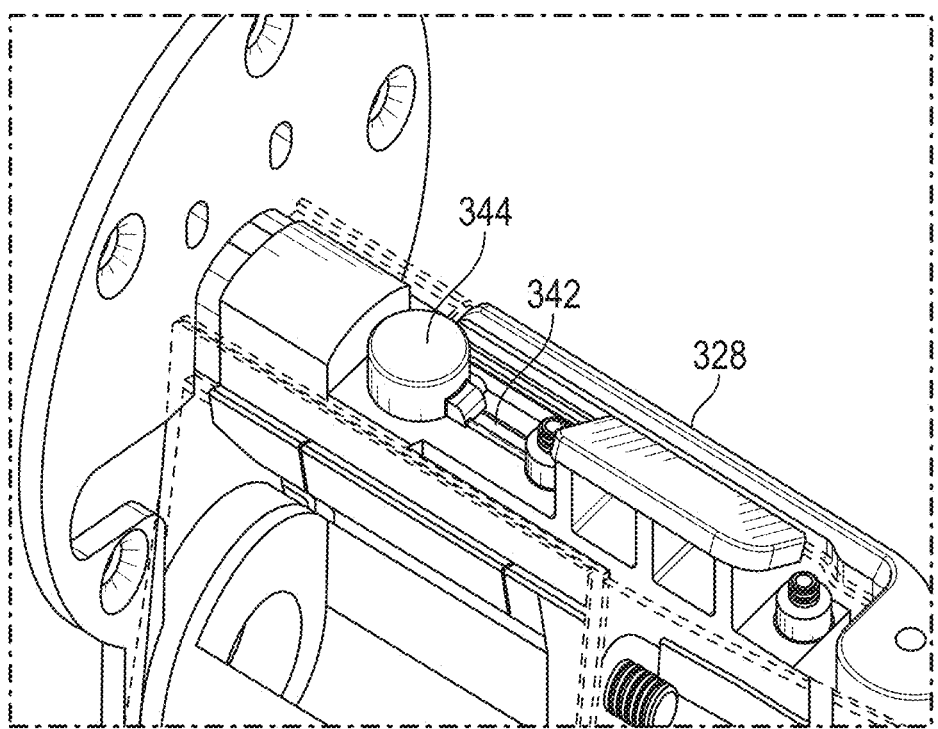
FIG. 25A illustrates an example location of a haptic feedback device according to some embodiments.

When an operator operates the input devices, the handpiece may provide a feedback to the operator. In some cases, the feedback may be provided when the operator switches a function from a first mode to a second mode different from the first mode. The feedback may include a haptic feedback, a visual feedback, an audio feedback, a tactile feedback or a force feedback, or a combination thereof. This feedback function may be useful to an operator or user since they can be notified when a function is switched between different modes. This may enhance safety, as the operator can be assured by the feedback that their input has been properly received by the system, and thus he or she is in a certain operation mode that is intended. The feedback device may be located in a portion of the handpiece that would contact the palm of the user to facilitate a better or more significant feel of the feedback. Types of actuation provided by the feedback device may be different for each function, for example, to allow the user to determine which function they have enabled based on feedback alone. Types of feedback may be configurable by the user. Users may want to enable the change based on personal preference especially in view of signals/patterns they are familiar with in a non-surgery environment, for example, car, phone or tablet, etc. In some cases, a driver or controller of the feedback device may be located outside the handpiece, for example, somewhere in the workstation 102, whereas an actuator of the feedback device may be located in the handpiece, as long as an operator may be provided a feedback by the handpiece upon a function change. In some cases, multiple feedback devices may be included in the handpiece at different locations to make it easier for the user to better recognize the feedback and/or distinguish the various types of feedback. For example, a first feedback device may be included in the portion of the handpiece that would contact the palm while a second feedback device may be included in a portion of the handpiece near a location contacted by the user's thumb or proximate the distal portion of the handpiece (as shown in FIG. 25A near 344).

Figure 24:
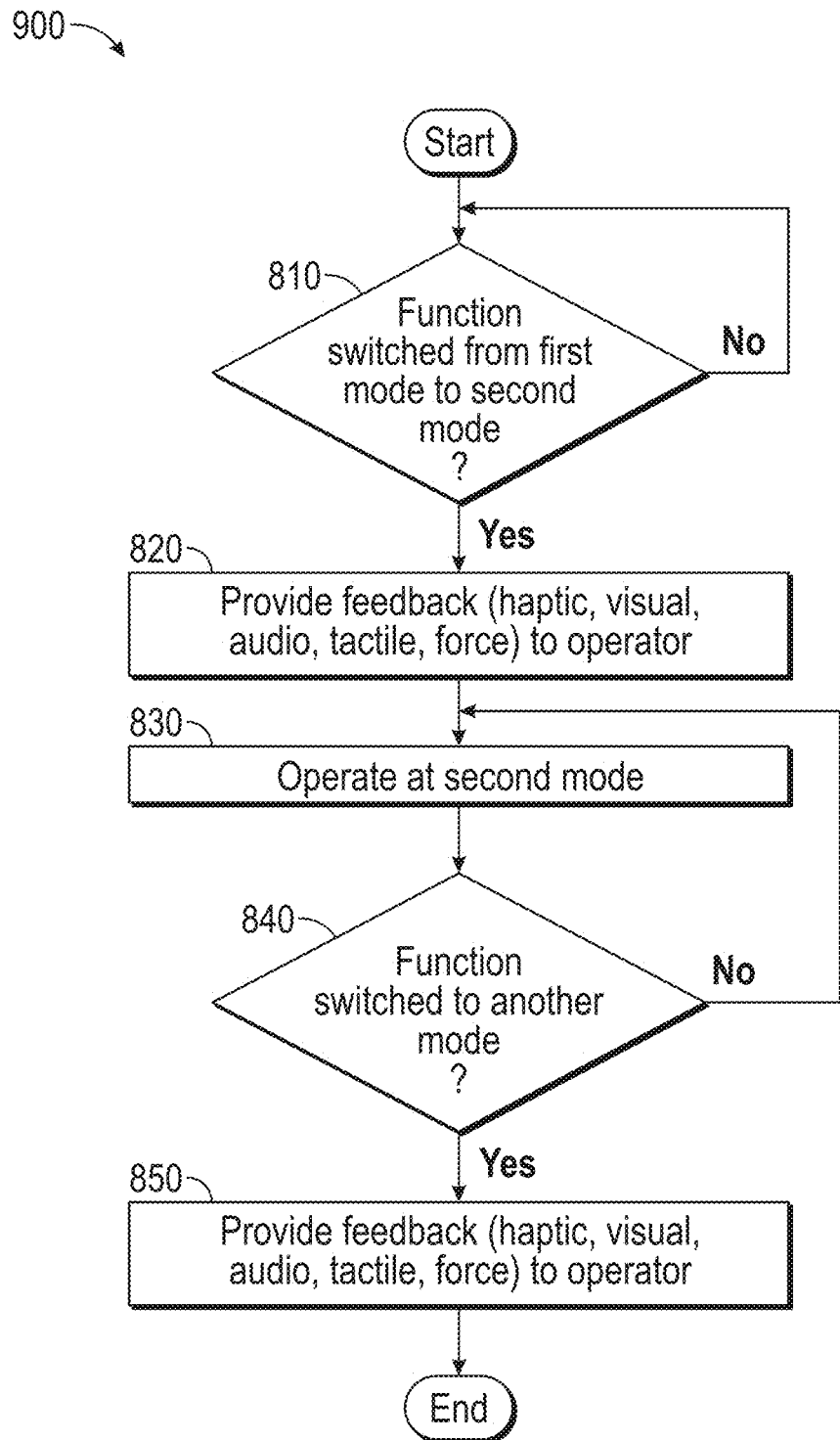
FIG. 24 illustrates a flowchart for a hand controller feedback control process according to some embodiments.

FIG. 24 illustrates a flowchart for a handpiece feedback control process 900 according to some embodiments. The process 900 may be performed by a processor or controller. Referring to FIG. 24, the handpiece feedback control process 900 will be described.

In state 810, it is determined whether a function has been switched from a first mode to a second mode. During operation, an operator may switch a function between modes. In some cases, the function switching may be sensed by the input control interface 326a. The function may include controlling a camera that images a surgery site, instrument clutching to reposition the hand grip apparatus, pre-set surgery routines, or other operation to control the surgical tool. In some cases, when the function is controlling the camera, the first mode may be enabling the camera control and the second mode may be disabling the camera control. In some cases, when the function is instrument clutching, the first mode may be enabling instrument clutching and the second mode may be disabling the instrument clutching. The function switching may originate in the hand grip apparatus 122/124 or the foot pedal 126 of the robotic surgery system 100. A function switch can originate in the handpiece and/or the foot pedal 126. If it is determined in state 810 that the function switching has not occurred, the state 810 may repeat.

If it is determined in state 810 that the function has been switched from the first mode to the second mode, the processor may provide a feedback to an operator (state 820). The feedback may include haptic, visual, audio, tactile, force or any other feedback, or a combination thereof, that can notify the operator about the mode change. After the feedback is provided, the handpiece may operate at the second (different) mode (state 830). For example, when an association of the camera with handpieces is re-enabled, the operator may continue to control the camera with the use of at least one of the handpieces.

In state 840, it is determined again whether a function has been switched from the second mode to another mode (such as the first mode or third mode). If it is determined in state 840 that the function has not been switched from the second mode to another mode, the states 830 and 840 may repeat. If it is determined in state 840 that the function has been switched from the first mode to the other mode, the processor may provide a feedback to the operator (state 850). The processor may perform the states 840 and 850 substantially the same way as with states 810 and 820.

1. Haptic Feedback

The handpiece feedback device can include a haptic feedback device. In some cases, the haptic feedback device may include a haptic actuator and a haptic driver. The haptic actuator may include a motor or actuator available from Texas Instruments. The haptic actuator may provide a haptic feedback in the form of vibration. The haptic driver (processor or controller) may drive the haptic actuator to provide a vibrational feedback when a robotic surgery function is switched from a first mode to a second mode.

The vibrational feedback may have a variety of different vibration patterns. For example, the vibration can have different strength levels, different durations, directions or intervals (if multiple vibrations involved). Furthermore, different types or patterns of vibration may be used for different mode switching and may be user configurable. Alternatively, the same vibration can be used for all mode switching.

In some cases, the haptic driver may be implemented with, for example, ICs available from Texas Instruments. The TI ICs may be I2C controlled and can be triggered by the workstation.

Figure 25B:
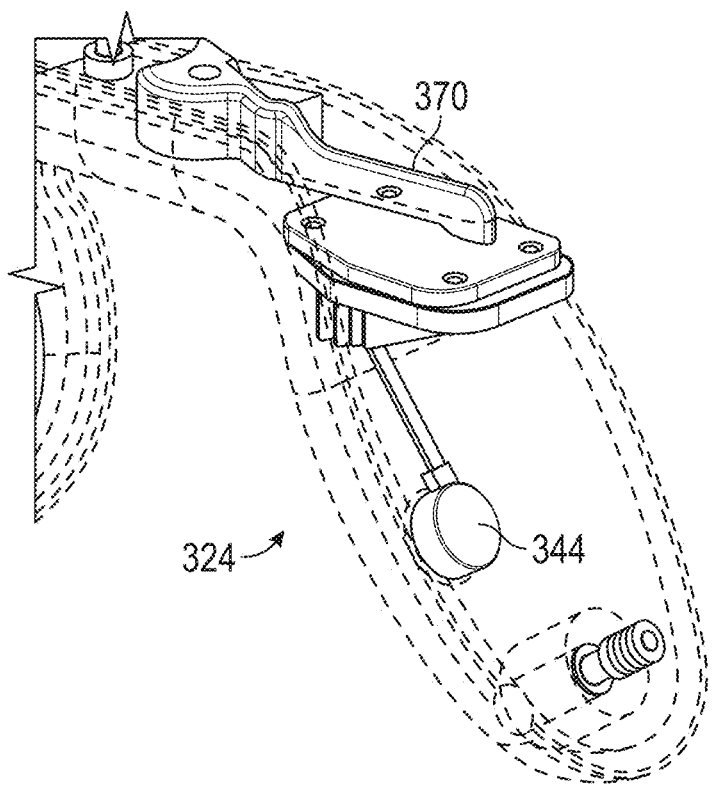
FIG. 25B illustrates another example location of a haptic feedback device according to some embodiments.

In some cases, as shown in FIG. 25A, the haptic feedback device 344 can be mounted directly in front of the gesture area, for example, on the center mount 342 of the handpiece. In some cases, as shown in FIG. 25B, the haptic feedback device 344 can be mounted in the lower handle/grip element (for example, inside the lower region of the upper and lower housings 324 and 322). However, the haptic feedback device 344 can be mounted in any other region in the handpiece, as long as it can provide a haptic feedback, when the user switches from one mode to another. In some cases, the haptic actuator may be provided inside the handpiece, and the haptic driver may be positioned outside the handpiece, for example, somewhere in the workstation 102 where the haptic driver can remotely control the haptic actuator. In some cases, multiple haptic actuators may be provided inside the handpiece, for example as shown in both FIGS. 25A and 25B at 344.

2. Visual Feedback

The handpiece feedback device can include a visual feedback device. The visual feedback device may include a light source and a controller (not shown). The controller may sense whether a function is switched between different modes and control the light source to emit light based on the sensed function switching. The light source may be any light emitter or generator such as an LED. The light source may be disposed around the input control interface 326a. However, the light source can be disposed in any other location in the handpiece as long as light emitted by the light source can be recognized by an operator. The light source can emit light in a single color or multiple colors. The light source can emit light having a particular shape. The different shapes and/or colors of light may be emitted according to different modes of the function to be switched and may be user configurable.

3. Audio Feedback

The handpiece feedback device can include an audio feedback device. The audio feedback device may include a speaker and a controller (not shown). The controller may sense whether a function is switched between different modes and control the speaker to make sound based on the sensed function switching. The speaker may be disposed around the input control interface 326a. However, the speaker can be disposed in any other location inside or outside the handpiece as long as sound can be heard by an operator. The sound can have a variety of patterns, in terms of types of sound, volume levels, sound duration or interval (if multiple types of sound involved). The different types of sound may be output according to different modes of the function to be switched and may be user configurable.

4. Tactile Feedback

The handpiece feedback device can include a tactile feedback device configured to provide a tactile feedback in response to the function switching. The tactile feedback may include a variety of types of feeling that an operator may have on a portion of the handpiece. The portion of the handpiece may be the input control interface 326a or any other location in the handpiece where an operator can recognize a tactile feedback. The tactile feedback may include one or more of: a bump, a beak, a grove, a lip, or a texture difference (for example, course finish to smooth finish in the input control interface 326a). The different types of tactile feedback may be provided according to different modes of the function to be switched and may be user configurable.

5. Force Feedback

The handpiece feedback device can include a force feedback device configured to provide a tactile feedback in response to the function switching. The force feedback may include a variety of types of force that an operator may sense on a portion of the handpiece. The portion of the handpiece may be the input control interface 326a or any other location in the handpiece where an operator can recognize a force feedback. The force feedback may include a self-centering wheel.

Handpiece System Block Diagram

Figure 26:
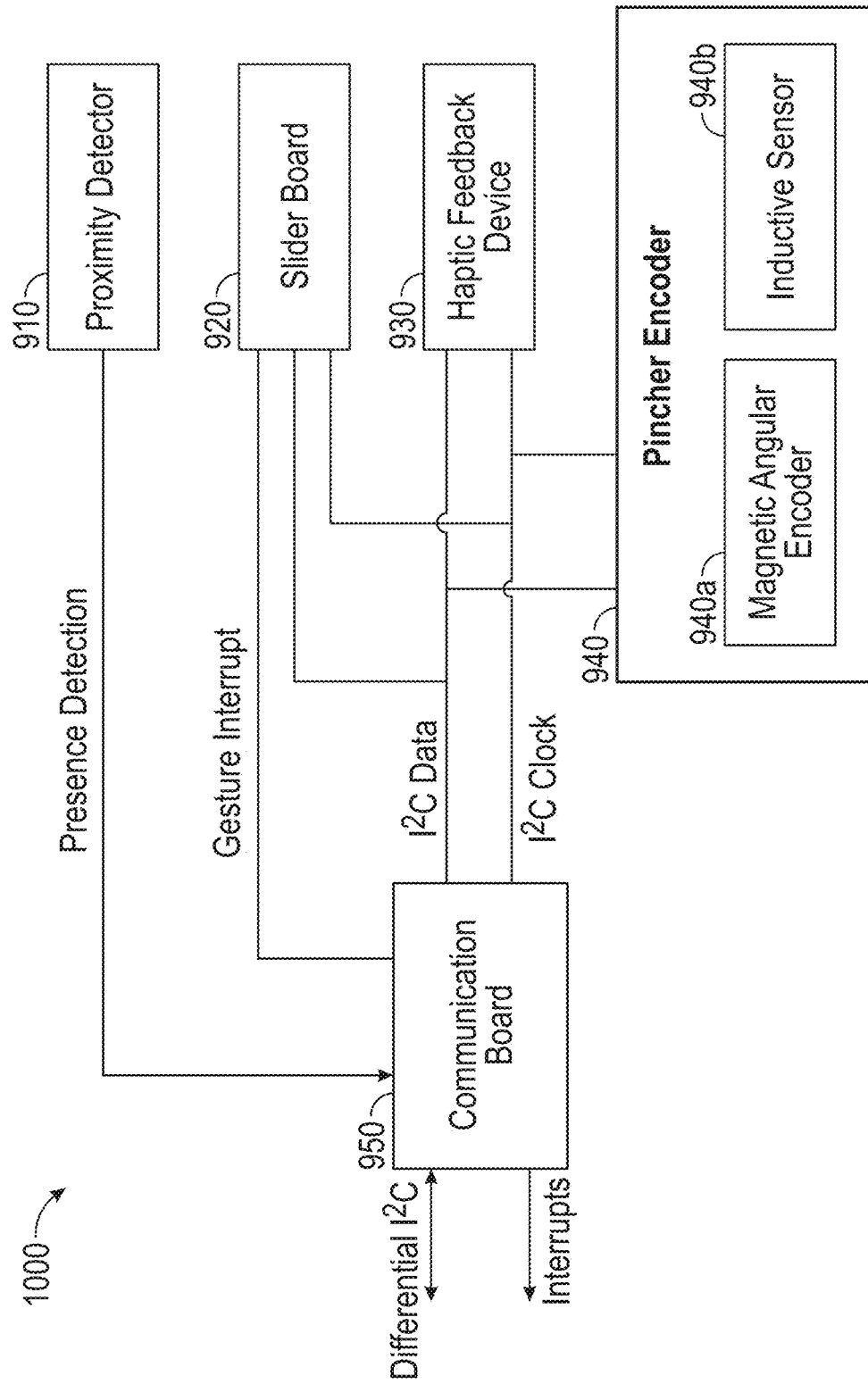
FIG. 26 illustrates a block diagram of a hand controller according to some embodiments.

FIG. 26 illustrates a block diagram of a handpiece 1000 according to some embodiments. Referring to FIG. 26, the handpiece 1000 includes a proximity detector 910, a slider board 920, a haptic feedback device 930, a pincher encoder 940 including a magnetic angular encoder 940a and/or an inductive sensor 940b, and a communication board 950. Although a number of separate components are illustrated in FIG. 26, those of skill in the art will recognize that one or more of the components may be combined or commonly implemented. For example, the proximity detector 910, the magnetic angular encoder 940 and/or the inductive sensor 950 may be implemented in a single PCB, for example, the first PCB 350 or the second PCB 326 described with respect to FIG. 10. Further, at least one of the components illustrated in FIG. 26 may be implemented using a plurality of separate elements or may be omitted. As another example, all of the components 910-950 may be implemented in a single PCB. Another processor or controller, disposed either inside or outside the handpiece 1000, may also be used to control one or more of the components 910-950.

In some cases, all of the components 910-950 may be disposed inside the handpiece 900. In some cases, at least one of the components 910-950 may be disposed outside the handpiece 900, for example, somewhere in the robotic surgery system 100 such as in the workstation 102 (see, for example, FIG. 1). Although FIG. 26 shows that all of the components 910-950 communicate data with each other via a wired network, at least one of the components 910-950 may wirelessly communicate data with one or more of the remaining components.

The proximity detector or presence detector 910 may detect whether a user's hand is present within a certain distance of the handpiece 900. The proximity detector 910 may provide a detected result to the communication board 950 so that a corresponding control (for example, activating or deactivating the handpiece) may be subsequently performed based on the detected result. The presence detector 910 may provide a general purpose output such as simple digital high's and low's to the communication board 950. The proximity detector 910 can be implemented with, for example, a capacitive proximity detector available from Microchip as described herein.

The slider board 920 may be used to drive the input control interface 326a such as a trackpad or capacitive touch surface described herein. The slider board 920 may provide a sensed result to the communication board 950 so that a corresponding control (for example, gesture control, shared input control, additional input control) may be subsequently performed based on the sensed result. The slider board 920 may be implemented with, for example, the ICs available from Microchip as described herein.

The haptic feedback device 930 may provide a haptic feedback to an operator, when the operator switches a function from a first mode to a second mode different from the first mode as described herein. Although not shown in FIG. 26, at least one of other feedback devices (visual feedback device, audio feedback device, tactile feedback device or force feedback device) may also be included in the handpiece 1000. The haptic feedback device 930 may provide a haptic feedback to an operator via the communication board 950. The haptic feedback device 930 can be implemented with, for example, the ICs available from Texas Instruments as described herein.

The pincher encoder (or pincher angle detector) 940 may magnetically or inductively detect a pincer angle and provide the detected result to the communication board 950 so that a corresponding control (for example, control of jaw movement of a surgical instrument) may be subsequently performed based on the detected result. The pincher encoder 940 may include the magnetic angular detector 940a and/or the inductive sensor 940b.

The magnetic angular detector 940a may detect an angular movement of a magnetic target attached to or integrally formed with the wiper 370 shown in FIGS. 10-11B. The magnetic angular detector 940a may be implemented with, for example, the MPS ICs or ADI ICs as discussed herein.

The inductive sensor 940b may detect a pincer angle by inductively sensing a movement of a metallic target formed in the wiper 370 or the paddle 329. The inductive sensor 940b may be implemented with, for example, the TI ICs or IDT ICs as discussed herein.

The communication board 950 may be used to communicate data with the components 910-940, or devices external to the handpiece 1000. The communication board 950 may be implemented with, for example, ICs available from NXP Semiconductors. The NXP ICs may convert all data to a differential I2C format. The slider board 920 and the pincher encoder 940 may use a shared I2C bus for communication with the communication board 950. However, the present disclosure is not limited to the I2C protocol, and other communication protocols such as serial peripheral interface (SPI) or System Management Bus (SMBus) could also be used. Furthermore, simple quadrature encoding could be used for the pincher encoder 940.

Handpiece Ergonomic Features

As discussed herein, during operation, an operator grasps a handpiece with his/her hand and moves the handpiece such that the instrument mimics the movement of the handpiece. For example, the operator may push toward and pull the handpiece from input devices, move upward, downwards, leftwards, rightwards or diagonal wise, or rotate the handpiece about a longitudinal axis thereof. Furthermore, the operator opens and closes the paddle 329 to control an open and close movement of the instrument. Moreover, during operation, an operator generally spends a substantial amount of time (for example, half an hour to few hours) in operating the handpiece. Thus, it is desirable that the handpiece is designed or structured to be user friendly, safe, ergonomic, reduce user fatigue and/or improve operation efficiency. In some cases, the handpiece may have multiple ergonomic features. For example, several components of the handpiece (for example, palm grip, neck portion, paddle, slanted top, ridge, pivot joint, cutout, etc.) may be ergonomically shaped and/or sized.

1. Palm Grip

Figure 27:
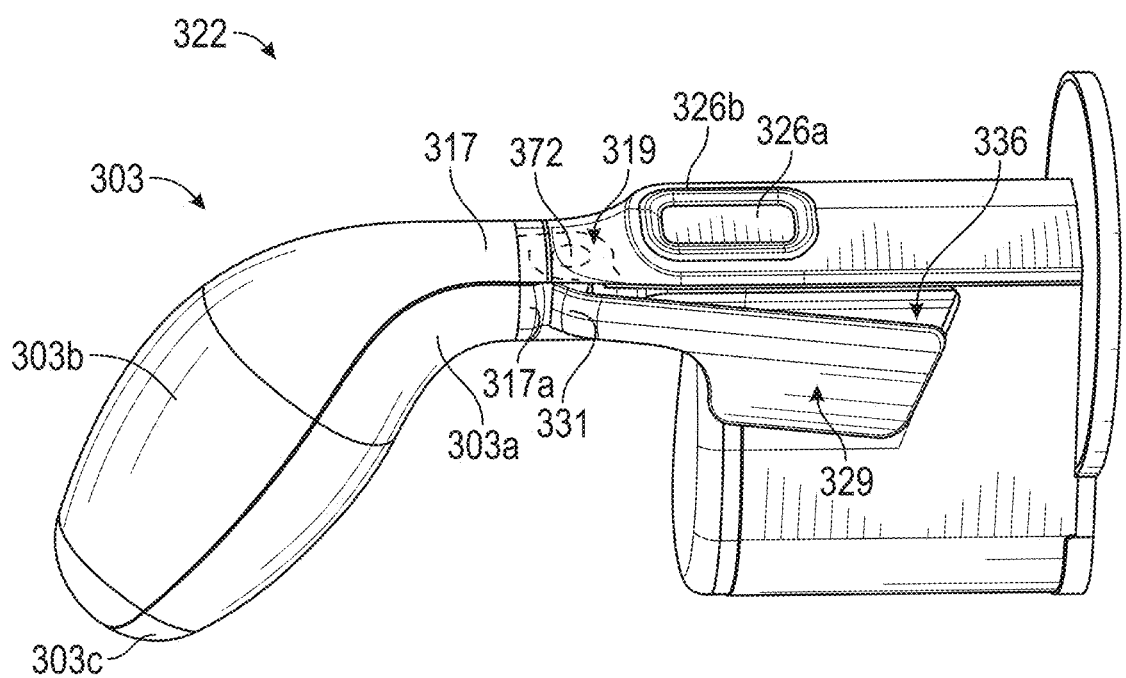
FIG. 27 illustrates a perspective view of a right side hand controller showing palm grip ergonomic features according to some embodiments.
Figure 28:
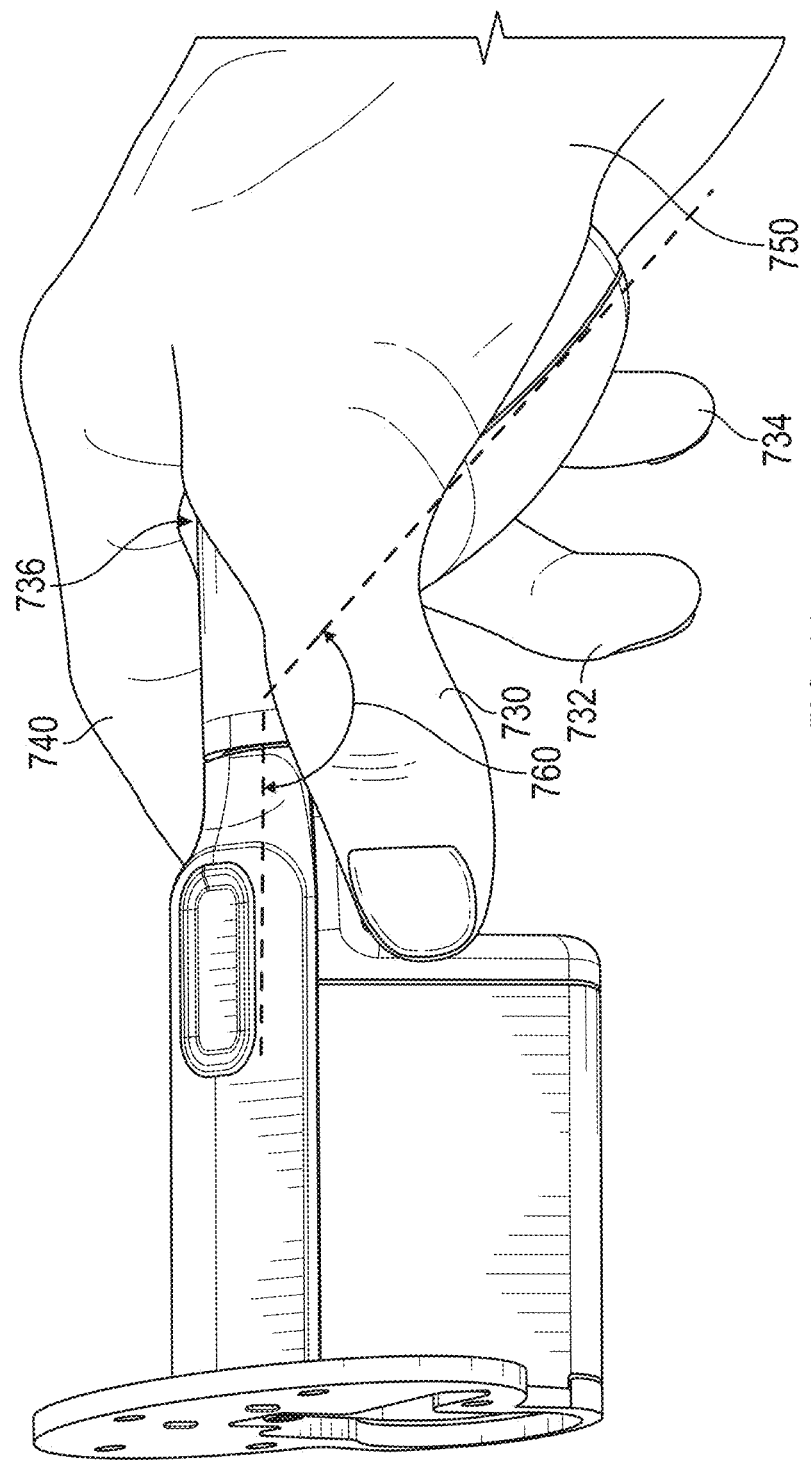
FIG. 28 illustrates a perspective view of the right side hand controller of FIG. 27 grasped by a user's right hand according to some embodiments.

FIG. 27 illustrates a perspective view of a right side handpiece 122 showing palm grip ergonomic features according to some embodiments. FIG. 28 illustrates a perspective view of the right side handpiece 122 of FIG. 27 grasped by a user's right hand according to some embodiments. Referring to FIG. 27, the handpiece 122 includes a palm grip 303. The palm grip (hereinafter to be interchangeably used with a "handle") 303 is a region of the handpiece 122 that is grasped and/or supported by the operator's palm 750 (see, for example, FIG. 28). In some cases, the palm grip 303 may be sufficiently long to permit a substantial portion of an average operator's palm to be rested on. This design may be advantageous over a linear handle or a curved but relative shorter handle, in that an operator may be able to more securely and comfortably grasp the handpiece 122 using the longer and ergonomically shaped palm grip 303. Furthermore, due to a longer/larger dimension and ergonomic design, the palm grip 303 may have a larger contact surface area where an operator's palm can rest.

The palm grip 303 may include an upper grip (or upper portion) 303a, a middle grip (or middle portion) 303b and a lower grip (or lower portion) 303c. The upper grip 303a may extend from the neck portion 317 toward the proximal end. The middle grip 303b may downwardly extend at a first angle from the upper grip 303a. The lower grip 303c may downwardly extend at a second angle from the middle grip 303b. The first and second angles may be the same as or different from each other depending on the embodiment. The upper and lower grips 303a and 303c may have a narrower diameter or width than that of the middle grip 303b so that the palm grip 303 as a whole has a substantially 'egg' shape. The width or diameter of the upper grip 303a may be larger than that of the neck portion 317. The upper grip 303a may be shaped and sized to permit at least a portion of an average operator's finger (for example, thumb or index finger) to be comfortably rested or supported. The middle grip 303b may have an external surface that is curved to correspond to a curvature of at least part of an average operator's palm.

In some cases, as shown in FIG. 28, the palm grip 303 may form an obtuse angle 760 with the neck portion 317. The obtuse angle 760 may correspond to the anatomy of an average operator's hand. The obtuse angle 760 may be substantially similar to an angle of a natural curvature of an average operator's hand when gripping the handpiece 122 as shown in FIG. 28. In these cases, an operator's thumb 730 and index finger 740 may be positioned on a region of the handpiece 122 (for example, the index finger 740 on or near the paddle 329 and the thumb 730 on opposite side of the index finger 740) substantially parallel to a longitudinal axis of the handpiece 122. Furthermore, the palm 750 may be positioned on the palm grip 303 such that the angle between the thumb 730/index finger 740 and the palm 750 may be substantially similar to the obtuse angle defined between the neck portion 317 and the palm grip 303. The slanted angle of the palm grip 303 may provide a maximum contact with the palm 750 while providing comfort to the operator. The operator's middle finger 736 may be positioned on a downward extension 764 of the paddle 329 (see, for example, FIG. 29), and the other two fingers 732 and 734 may be rested on a portion of the palm grip 303.

Thus, the ergonomically shaped palm grip design may provide comfort and convenience while reducing user fatigue and improving operation efficiency.

2. Neck Portion

In some cases, as shown in FIG. 27, the handpiece 122 may also include a neck portion 317 positioned between the upper grip 303a and the pivot joint 372 (see also FIG. 11A). The neck portion 317 may have a reduced cross sectional extent with respect to the upper grip 303a. The neck portion 317 may permit an operator's fingers (for example, thumb 730 or index finger 740) to be comfortably rested thereon.

Since the neck portion 317 is positioned between the upper grip 303a and the pivot joint 372, the neck portion 317 may not horizontally overlap the paddle 329. This may be advantageous, as it can permit an operator's finger to be rested thereon without the finger touching the paddle 329. The palm grip 303 and the neck portion 317 together may allow an operator to comfortably grasp the handpiece 122 while resting one or more of his/her fingers without interfering with the paddle operation.

In some cases, as shown in FIG. 27, the neck portion 317 may include a protruding side surface 317a that outwardly protrudes from a side thereof. Although FIG. 27 shows only one protruding side surface 317a, the neck portion 317 may include another protruding surface on the opposite side. The protruding surface 317a alone or in combination with a convexed tail end 331 (to be described with respect to FIG. 29 below) of the paddle 329 may enable operators to more easily roll (rotate) the handpiece 122 about a longitudinal axis of the handpiece 122, by turning the protruding side surface 317a and/or the convexed tail end 331 with their fingertip(s), without the need of rotating their wrists. In another case, during this handgrip rotating procedure, the operators may merely loosely grasp the palm grip 303.

In some cases, the protruding surface 317a of the neck portion 317 may be adjacent to or contact the convexed tail end 331. The protruding surface 317a may have a curvature substantially the same as or similar to that of the curvature of the convexed tail end 331. The combination of the protruding surface 317a and the convexed tail end 331 having the same or similar curvature may allow operators to more easily roll (rotate) the handpiece 122 by turning the combined elements 317a and 331, as the operator would have a larger convexed area to turn.

Thus, the ergonomic features of the neck portion may provide comfort and convenience while reducing user fatigue and improving operation efficiency.

3. Paddle

Figure 29:
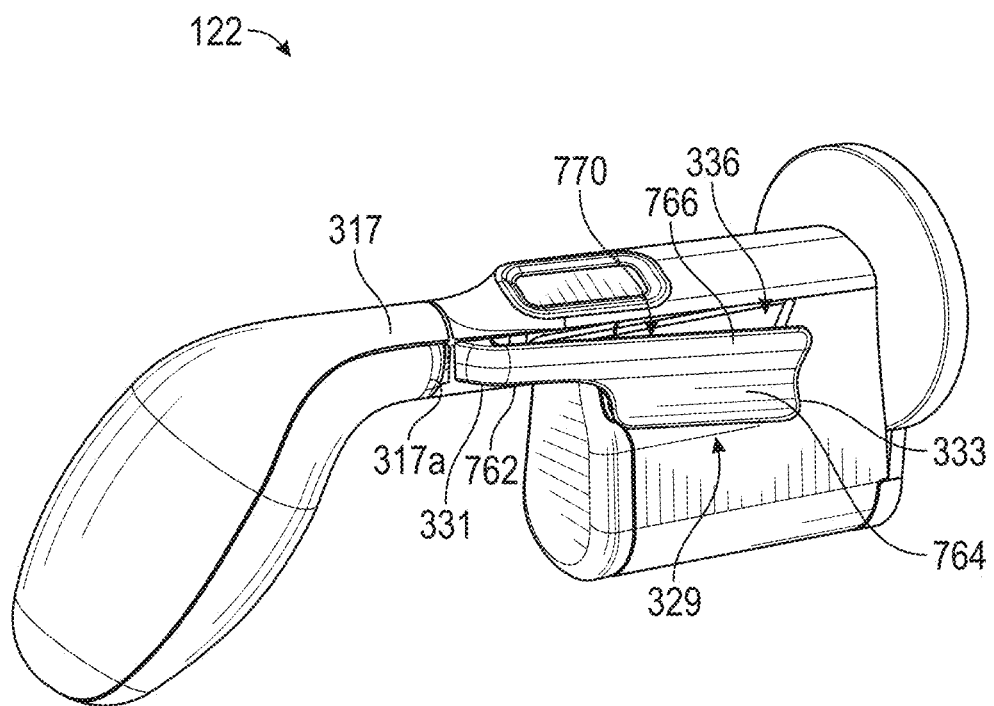
FIG. 29 illustrates a perspective view of a right side hand controller showing paddle ergonomic features according to some embodiments.
Figure 30:
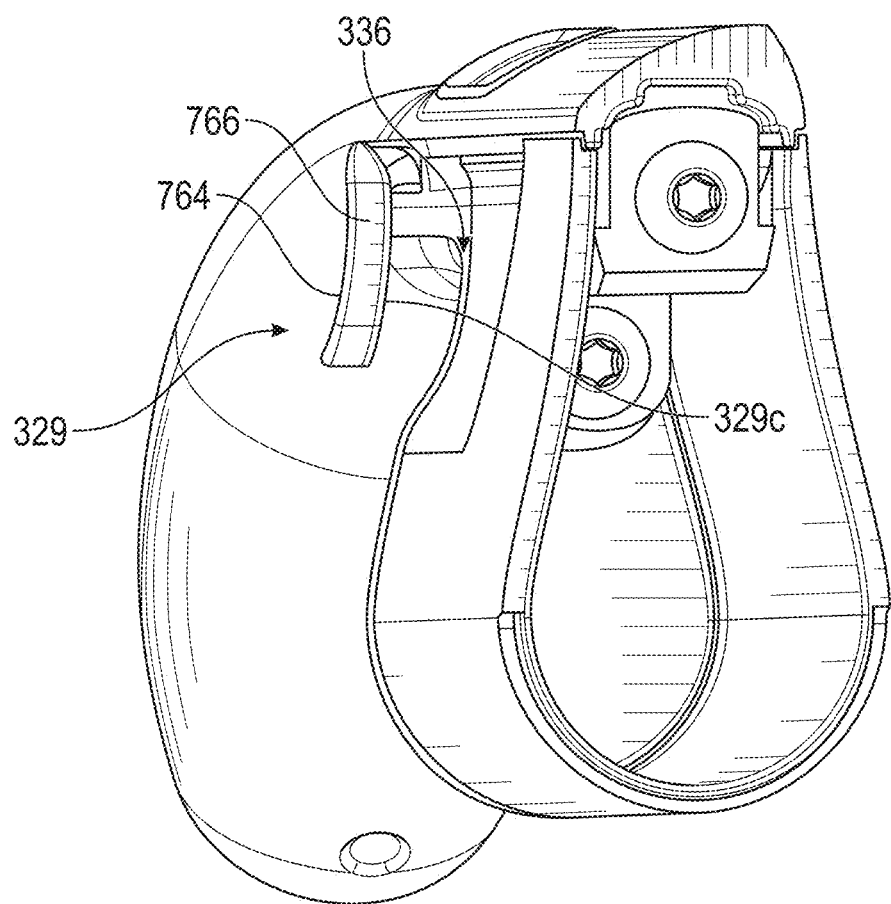
FIG. 30 illustrates a closed-up perspective view of a paddle of the right side hand controller of FIG. 29 according to some embodiments.
Figure 31:
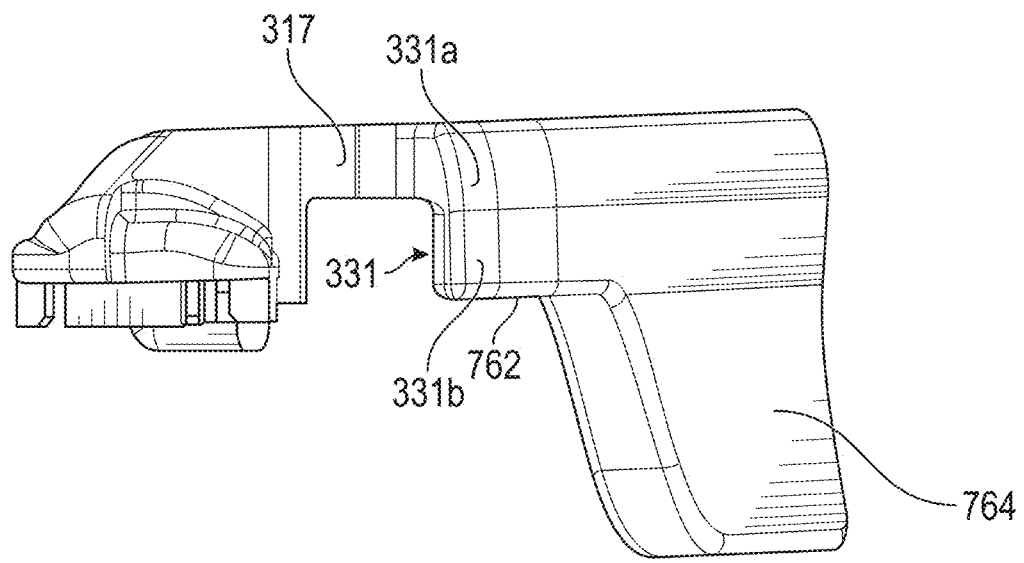
FIG. 31 illustrates a closed-up left side view of the paddle of FIG. 30 according to some embodiments.

FIG. 29 illustrates a perspective view of a right side handpiece 122 showing paddle ergonomic features according to some embodiments. FIG. 30 illustrates a closed-up perspective view of a paddle 329 of the right side handpiece 122 of FIG. 29 according to some embodiments (with irrelevant elements removed). FIG. 31 illustrates a close-up left side view of the paddle 329 of FIG. 30 according to some embodiments.

Referring to FIG. 29, the paddle 329 includes a tail end 331 and a paddle end 333. The paddle 329 may also include an upper portion 770 and a downward extension 764. The upper portion 770 includes a tail region 762 and a paddle region 766. The tail region 762 may include the tail end 331 and a non-tail end region adjacent to the tail end 331. The downward extension 764 downwardly extends from the paddle region 766. In some cases, as shown in FIG. 29, left and right ends of the downward extension 764 may be sized such that the upper side of the downward extension 764 has a width slightly greater than that of the lower side thereof. The tail region 762 may be sized to receive distal phalanges of an average operator's finger (for example, index finger) when grasped by the hand of the operator. The downward extension 764 may have a height greater than that of the tail region 762 where the height is measured in a direction substantially perpendicular to a longitudinal axis of the handpiece body. The downward extension 764 may be sized to accommodate at least two fingers of the operator such as index and middle fingers.

In some cases, an outer surface of the tail region 762 may be at least partially outwardly curved. For example, the outer surface may be at least partially convexed, crowned, arced or semi-circular. For example, an outer surface of the tail end 331 may be at least partially convexed. The convexed tail region 762 alone or in combination with the protruding side surface 317a of the neck portion 317 may enable operators to more easily roll (rotate) the handpiece 122 about a longitudinal axis of the handpiece 122, by turning at least one of the two protruding elements 762 and 317a with their fingertip(s), without the need of rotating their wrists, or by merely loosely grasping the palm grip 303.

In some cases, as shown in FIG. 31, the tail end 331 may be fully convexed. For example, an outer surface of the tail end 331 may have a substantially convexed lens shape. In some cases, as shown in FIG. 31, the tail end 331 may be partially convexed. In these cases, the tail end 331 may include an upper convexed portion 331a and a lower substantially flat portion 331b. In some cases, the lower portion 331b may be convexed and the upper portion 331a may be substantially flat. The remaining portion of the tail region 762 may be substantially flat, convexed or less convexed than the tail end 331.

In some cases, instead of or in addition to the outwardly curved surface, the tail end 331 may include one or more individual protrusions spaced apart (not shown). In some cases, the entire tail region 762 may be convexed. The paddle region 766 may be substantially flat or less convexed (in terms of curvature) than the tail region 762. In some cases, the tail region 762 may include other shape or structure as long as it can permit operators to more easily rotate the handpiece 122 with an operator's fingertip(s).

The downward extension 764 may be at least partially concaved or inwardly curved (opposite curve of the curvature described herein for the tail end 331). The concaved portion 764 may allow an operator to grab the paddle 329 or rest his or her fingers thereon. In some cases, as shown in FIGS. 29 and 30, the entirety of the downward extension 764 may be concaved. In some cases, the downward extension 764 may be partially concaved.

Thus, the ergonomic features (convexed tail region and concaved downward extension) of the paddle 329 may provide comfort and convenience while reducing user fatigue and improving operation efficiency.

4. Slanted Top

Figure 32:
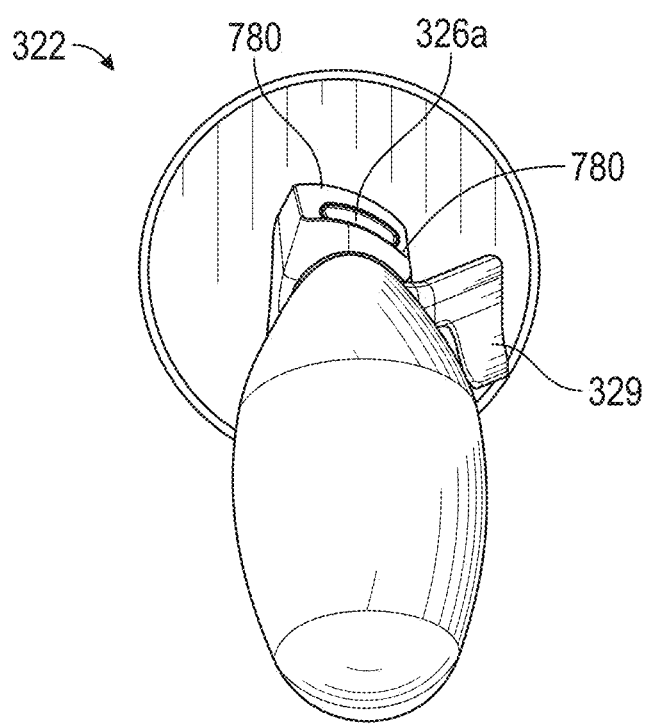
FIG. 32 illustrates a rear view of a right side hand controller showing another example ergonomic features according to some embodiments.

FIG. 32 illustrates a rear view of a right side handpiece 122 showing additional handpiece ergonomic features according to some embodiments. In some cases, as shown in FIG. 32, the handpiece 122 may include a slanted top surface 780 that is slanted toward a side surface of the body where an operator's index finger is configured to be positioned when the handpiece is grasped by the hand of the operator. For example, for a right side handpiece having a paddle disposed on the right side of the body (see, for example, FIG. 32), the slanted top surface 780 may be slanted toward the paddle 329 or the cutout 336. As another example, for a right side handpiece having a paddle disposed on the left side of the body (not shown), the slanted top surface may be slanted toward a side of the body on the opposite side of the paddle. As another example, for a left side handpiece having a paddle disposed on the left side of the body (see, for example, FIG. 3A), the slanted top surface may be slanted toward the paddle or the cutout. As another example, for a left side handpiece having a paddle disposed on the right side of the body (see, for example, FIG. 6A), the slanted top surface may be slanted toward a side of the body on the opposite side of the paddle. As another example, for a handpiece having paddles disposed on both the left and right sides of the body (see, for example, FIG. 9), the top surface may be relative flat or have side (or edge portions) that curve toward each of the left and right sides of the body. The curvature of the top surface may be a convex curvature.

The slanted top surface 780 may be advantageous in that an operator can easily move his or her index finger between the input control interface 326a and the paddle 329, as the input control interface 326a is closer to the paddle 329, compared to a non-slanted handpiece top. Thus, the slanted top 780 may provide convenience while improving operation efficiency.

5. Ridge around Input Control Interface

In some cases, as shown in FIG. 27, the handpiece 122 may include a ridge 326b around the input control interface 326a. The ridge 326b surrounds the input control interface 326a and is upwardly protruded or raised from an edge of the input control interface 326a. The ridge 326b may help an operator recognize the location of the input touch interface 326a during operation without necessarily having to look at the handpiece 122. Although FIG. 27 shows that the ridge 326b fully surrounds the input control interface 326a, the ridge 326b may be formed to only partially surround the input control interface 326a. In some cases, the ridge 326b may include a plurality of individual protrusions spaced apart along the edge of the input control interface 326a. In some cases, the ridge 326b may have other shapes that can provide a tactile feedback to an operator regarding the position of the input touch interface 326a. Thus, the ridge 326b may also provide convenience while improving operation efficiency and accuracy.

6. Sloped Region

In some cases, as shown in FIG. 27, the handpiece 122 may include a sloped region 319 between the neck portion 317 and the ridge 326b of the input control interface 326a. Since there is a height difference between the neck portion 317 and the ridge 326b, the two elements 317 and 326a are connected via the sloped region 319. The sloped region 319 may be downwardly curved or linear. In some cases, the sloped region 319 alone may be used for an operator to rest his or her finger thereon. In some cases, the sloped portion 319 and the neck portion 317 together may be used to accommodate an operator's finger (for example, thumb or index finger) for resting. Thus, the sloped region 319 may provide more comfort, thereby reducing user fatigue.

7. Pivot Joint and Paddle Movement Mechanism

Referring to FIG. 11A and FIG. 27, the pivot joint 327 is disposed inside the handpiece body (see also FIG. 11A). Since there is no pivot joint disposed outside the handpiece body, an operator may be prevented from being finger-pinched by a pivot joint and/or a portion of the outside of the handpiece body. In addition to enhancing user safety, the handpiece 122 may appear aesthetically better and neater by not placing the pivot joint outside or near the side of the handpiece body. Furthermore, in combination with the wiper 370 (see, for example, FIG. 11A), the pivot joint 372 may more securely fix the paddle 329 to the handpiece body.

Referring back to FIG. 11A, the paddle 329 and the wiper 370 are connected to and arranged in a substantially spaced apart and parallel relationship with each other (see arrows 371 in FIG. 11A). Having the paddle 329 and the wiper 370 on opposite sides of the pivot joint 372 but spaced apart allows for compactness of the handpieces. Otherwise, if they were inline, the wiper 370 would need to extend farther towards the proximal end in order to have enough spacing to detect a change in angle (using the angular detection sensor or curved coil layout if using an inductive detector described herein). This may also allow the paddle 329 to extend out and away from the body to provide a comfortable grip for the user.

In some cases, as shown in FIG. 11A, the paddle 329 may have a central longitudinal axis 371 that does not intersect the pivot joint 372. Furthermore, the pivot joint 372 may be disposed inside the body to be closer to a longitudinal axis 373 of the body than the longitudinal axis 371 of the paddle 329. This structure allows substantially the entirety of the paddle 329 to be disposed outside the body. Furthermore, the longitudinal axis 371 of the paddle 329 can be substantially parallel to the longitudinal axis 373 of the body in its closed position. The full closure and parallel arrangement of the paddle 329 may be beneficial in that the instrument can be fully closed based on the movement of the paddle 329. Moreover, the described structure also allows an inner surface of the paddle 329 to gently land on a side surface of the body that faces the paddle 329. This can prevent the paddle from colliding or otherwise having an undesirable physical impact on the paddle 329 when it is closed.

In some cases, as shown in FIG. 11A, the tail end of the paddle 329 may include a region 375 that is angled, slanted or curved toward the pivot joint 372. The angled region 375 may be used to conveniently open and close the paddle 329. The angled region 375 may be convexed to conveniently roll the handpiece without using the palm grip 303 as described herein.

With the ergonomic structure of the pivot joint 372 and the paddle 329 along with the wiper 370, no mechanical paddle movement detection mechanism, such as a rod that converts a rotational paddle movement into a linear movement, is required. Thus, the handpiece can be more efficiently manufactured and/or the pincer angle detection can be more accurately or efficiently made. Furthermore, the handpiece may be more safely operated by a user.

8. Cutout

In some cases, as shown in FIG. 27, the handpiece 122 may also include a cutout 336 formed in the side surface of the body that faces the paddle 329. The cutout 336 may be shaped to accommodate the paddle 329. For example, as shown in FIG. 30, the inner surface 329c of the paddle 329 may be inwardly curved, and the cutout 336 may be correspondingly shaped to accommodate the curved inner surface 329c of the paddle 329. As described herein, the longitudinal axis 371 of the paddle 329 can be substantially parallel to the longitudinal axis 373 of the body in its closed position. The cutout 336 may more easily enable the parallel arrangement between the axes 371 and 373 of the paddle 329 and the body by accommodating the paddle 329 therein.

OTHER VARIATIONS

Those skilled in the art will appreciate that, in some embodiments, additional components and/or steps can be utilized, and disclosed components and/or steps can be combined or omitted. For example, although some embodiments are described in connection with a robotic surgery system, the disclosure is not so limited. Systems, devices, and methods described herein can be applicable to medical procedures in general, among other uses. As another example, certain components can be illustrated and/or described as being circular or cylindrical. In some implementations, the components can be additionally or alternatively include non-circular portions, such as portions having straight lines. As yet another example, any of the actuators described herein can include one or more motors, such as electrical motors. As yet another example, in addition to or instead of controlling tilt and/or pan of a camera, roll (or spin) can be controlled. For example, one or more actuators can be provided for controlling the spin.

The foregoing description details certain embodiments of the systems, devices, and methods disclosed herein. It will be appreciated, however, that no matter how detailed the foregoing appears in text, the systems, devices, and methods can be practiced in many ways. The use of particular terminology when describing certain features or aspects of the disclosure should not be taken to imply that the terminology is being redefined herein to be restricted to including any specific characteristics of the features or aspects of the technology with which that terminology is associated.

It will be appreciated by those skilled in the art that various modifications and changes can be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures can be combined, interchanged, or excluded from other embodiments.

With respect to the use of substantially any plural and/or singular terms herein, those having skill in the art can translate from the plural to the singular and/or from the singular to the plural as is appropriate to the context and/or application. The various singular/plural permutations can be expressly set forth herein for sake of clarity.

Directional terms used herein (for example, top, bottom, side, up, down, inward, outward, etc.) are generally used with reference to the orientation or perspective shown in the figures and are not intended to be limiting. For example, positioning "above" described herein can refer to positioning below or on one of sides. Thus, features described as being "above" may be included below, on one of sides, or the like.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations).

The term "comprising" as used herein is synonymous with "including," "containing," or "characterized by," and is inclusive or open-ended and does not exclude additional, unrecited elements or method steps.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function and/or achieves a desired result. For example, the terms "approximately", "about", "generally," and "substantially" may refer to an amount that is within less than 10% of, within less than 5% of, within less than 1% of, within less than 0.1% of, and/or within less than 0.01% of the stated amount.

It will be further understood by those within the art that any disjunctive word and/or phrase presenting two or more alternative terms, whether in the description, claims, or drawings, can be understood to contemplate the possibilities of including one of the terms, either of the terms, or both terms. For example, the phrase "A or B" will be understood to include the possibilities of "A" or "B" or "A and B." Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the embodiments of the invention.

The various illustrative blocks, modules, and circuits described in connection with the embodiments disclosed herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm and functions described in connection with the embodiments disclosed herein may be embodied directly in hardware, in a software module executed by a processor, or in a combination of the two. If implemented in software, the functions may be stored on or transmitted over as one or more instructions or code on a tangible, non-transitory computer-readable medium. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD ROM, or any other form of storage medium known in the art. A storage medium is coupled to the processor such that the processor can read information from, and write information to, the storage medium. In the alternative, the storage medium may be integral to the processor. Disk and disc, as used herein, includes compact disc (CD), laser disc, optical disc, digital versatile disc (DVD), floppy disk and blu ray disc where disks usually reproduce data magnetically, while discs reproduce data optically with lasers. Combinations of the above should also be included within the scope of computer readable media. The processor and the storage medium may reside in an ASIC. The ASIC may reside in a user terminal. In the alternative, the processor and the storage medium may reside as discrete components in a user terminal.

The above description discloses embodiments of systems, apparatuses, devices, methods, and materials of the present disclosure. This disclosure is susceptible to modifications in the components, parts, elements, steps, and materials, as well as alterations in the fabrication methods and equipment. Such modifications will become apparent to those skilled in the art from a consideration of this disclosure or practice of the disclosure. Consequently, it is not intended that the disclosure be limited to the specific embodiments disclosed herein, but that it cover all modifications and alternatives coming within the scope and spirit of the subject matter embodied in the following claims.

What is claimed is:

1. A hand controller apparatus for controlling one or more tools in a robotic surgery system, the apparatus comprising:
    a body including a proximal portion and a distal portion extending to a distally located interface end configured to be coupled to an input apparatus configured to control a surgical tool, the proximal portion extending at an angle relative to the distal portion, the proximal portion configured to support at least a portion of a palm of a user's hand thereon;
    a lever having a tail end pivotally coupled to a lateral side of the distal portion of the body and extending along the body and away from a proximal end of the distal portion to a paddle end of the lever, the lever being laterally moveable relative to the lateral side of the body, the lever having a planar outer surface configured to support at least a portion of a finger of the user's hand thereon, wherein the lever is pivotally coupled to the distal portion via a pivot joint proximate the proximal end of the distal portion of the body; and
    an input control interface on an upper surface of the distal portion of the body and configured to receive an input from one or more fingers of the user's hand, the input control interface located closer to the tail end than the paddle end of the lever.

2. The apparatus of claim 1, wherein the tail end includes an inner surface facing the body and an outer surface opposing the inner surface, wherein at least part of the outer surface of the tail end is outwardly curved, and wherein the at least part of the outer surface of the tail end includes a substantially convex shape.

3. The apparatus of claim 1, wherein the proximal portion has a contoured surface configured to support at least a portion of the palm of the user's hand.

4. The apparatus of claim 3, wherein the contoured surface is a convex surface.

5. A hand controller apparatus for controlling one or more tools in a robotic surgery system, the apparatus comprising:
a body including a proximal portion and a distal portion extending to a distally located interface end configured to be coupled to an input apparatus configured to control a surgical tool, the proximal portion extending at an obtuse angle relative to the distal portion, the proximal portion configured to support at least a portion of a palm of a user's hand thereon;
a lever having a tail end pivotally coupled to a lateral side of the distal portion of the body and extending along the body and away from a proximal end of the distal portion to a paddle end of the lever, the lever being laterally moveable relative to the lateral side of the body, the lever having a planar outer surface configured to support at least a portion of a finger of the user's hand thereon, wherein the lever is pivotally coupled to the distal portion via a pivot joint proximate the proximal end of the body; and
an input control interface on an upper surface of the distal portion of the body and configured to receive an input from one or more fingers of the user's hand, the input control interface having a greater length than width, the input control interface located closer to the tail end than the paddle end of the lever.

6. The apparatus of claim 5, wherein the input control interface is generally rectangular.

7. The apparatus of claim 5, wherein the distal portion has at least one side surface that extends toward the distally located interface and is defined by a plane.

8. The apparatus of claim 5, wherein the tail end includes an inner surface facing the body and an outer surface opposing the inner surface, wherein at least part of the outer surface of the tail end is outwardly curved, and wherein the at least part of the outer surface of the tail end includes a substantially convex shape.

9. The apparatus of claim 5, wherein the proximal portion has a contoured surface configured to support at least a portion of the palm of the user's hand.

10. The apparatus of claim 9, wherein the contoured surface is a convex surface.

11. A hand controller apparatus for controlling one or more tools in a robotic surgery system, the apparatus comprising:
a body including a proximal portion and a distal portion extending to a distally located interface end configured to be coupled to an input apparatus configured to control a surgical tool, the distal portion having a medial side that extends toward the distally located interface and is defined by a plane, the distal portion also having a lateral side that has a recess along at least a portion of the length of the distal portion, the proximal portion extending at an obtuse angle relative to the distal portion, the proximal portion configured to support at least a portion of a palm of a user's hand thereon;
a lever pivotally coupled to the lateral side of the distal portion of the body and extending along the body and away from a proximal end of the distal portion, the lever being laterally moveable relative to the lateral side and configured to extend at least partially into the recess when fully depressed, the lever having a planar outer surface configured to support at least a portion of a finger of the user's hand thereon, wherein the lever is pivotally coupled to the distal portion via a pivot joint proximate the proximal end of the distal portion;
an input control interface on an upper surface of the distal portion of the body and configured to receive an input from one or more fingers of the user's hand; and
a lateral movement detector configured to magnetically or inductively detect a lateral movement of the lever, wherein detection of the lateral movement causes the input apparatus to control movement of the surgical tool based on the detected lateral movement of the lever, wherein the lateral movement detector comprises a magnetic angular sensor configured to detect an angle formed between the lever and the side surface of the body or an inductive sensor configured to detect a non-linear movement of a metallic portion disposed in or integrally formed with the lever.

12. The apparatus of claim 11, wherein the input control interface having a greater length than width.

13. The apparatus of claim 12, wherein the input control interface is generally rectangular.

14. The apparatus of claim 11, wherein the lever includes a tail region adjacent to the proximal end of the distal portion, wherein the tail region includes an inner surface facing the body and an outer surface opposing the inner surface, wherein at least part of the outer surface of the tail region is outwardly curved, and wherein the at least part of the outer surface of the tail region includes a substantially convex shape.

15. The apparatus of claim 11, wherein the proximal portion has a contoured surface configured to support at least a portion of the palm of the user's hand.

16. The apparatus of claim 15, wherein the contoured surface is a convex surface.

17. The apparatus of claim 11, further comprising a feedback device supported by the body and configured to provide feedback to a user in response to a change in a function of the hand controller apparatus from a first mode to a second mode, the first mode being different from the first mode, wherein the function comprises at least one: controlling a camera that images a surgical site, instrument clutching to reposition the hand controller apparatus, a pre-set surgery routine, or an operation to control the surgical tool, and wherein the change from the first mode to the second mode is configured to occur within the same function.

18. The apparatus of claim 17, wherein the feedback device is configured to provide a haptic feedback, a tactile feedback, a force feedback, a visual feedback or an audio feedback in response to the change in the function.

19. The apparatus of claim 11, wherein the input control interface is formed on a surface of the body and configured to sense the input from the one or more fingers of the user's hand, a processor configured to control a function of the one or more tools in response to the sensed input.

20. The apparatus of claim 19, wherein the input control interface comprises a trackpad or a capacitive touch surface configured to sense at least one of: swiping from a first side of the trackpad to a second side of the trackpad different from the first side, tapping, swiping and holding, tapping and holding, multiple tapping, or multiple tapping and holding.

* * * * *

UNITED STATES PATENT AND TRADEMARK OFFICE
CERTIFICATE OF CORRECTION

| | |
|---|---|
| PATENT NO. | : 11,446,102 B2 |
| APPLICATION NO. | : 17/643357 |
| DATED | : September 20, 2022 |
| INVENTOR(S) | : Duke et al. |

It is certified that error appears in the above-identified patent and that said Letters Patent is hereby corrected as shown below:

On the Title Page

On Page 2, Column 2, (Other Publications), Line 25: Delete "intuitivesurgcal" and insert -- intuitivesurgical --.

In the Claims

Column 50, Lines 40-41, Claim 17: Delete "from the first mode" and insert -- from the second mode --.

Signed and Sealed this
Sixteenth Day of May, 2023

Katherine Kelly Vidal
*Director of the United States Patent and Trademark Office*